(12) United States Patent
Holman et al.

(10) Patent No.: US 11,492,356 B2
(45) Date of Patent: Nov. 8, 2022

(54) CAVITAND COMPOSITIONS AND METHODS OF USE THEREOF

(71) Applicant: Georgetown University, Washington, DC (US)

(72) Inventors: Kevin Travis Holman, McLean, VA (US); Christopher Kane, Arlington, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 16/565,981

(22) Filed: Sep. 10, 2019

(65) Prior Publication Data

US 2020/0071338 A1 Mar. 5, 2020

Related U.S. Application Data

(62) Division of application No. 14/387,317, filed as application No. PCT/US2013/033612 on Mar. 22, 2013, now Pat. No. 10,435,413.

(60) Provisional application No. 61/799,037, filed on Mar. 15, 2013, provisional application No. 61/765,600, filed on Feb. 15, 2013, provisional application No. 61/614,967, filed on Mar. 23, 2012.

(51) Int. Cl.
| | | |
|---|---|---|
| *C01B 23/00* | (2006.01) | |
| *C07F 7/18* | (2006.01) | |
| *B01J 20/28* | (2006.01) | |
| *B01J 20/22* | (2006.01) | |
| *C07D 493/22* | (2006.01) | |
| *C07C 41/36* | (2006.01) | |
| *C07C 17/389* | (2006.01) | |
| *C07C 7/20* | (2006.01) | |
| *C10L 3/10* | (2006.01) | |
| *B01D 53/02* | (2006.01) | |

(52) U.S. Cl.
CPC .......... *C07D 493/22* (2013.01); *B01D 53/02* (2013.01); *B01J 20/22* (2013.01); *B01J 20/226* (2013.01); *B01J 20/28095* (2013.01); *C01B 23/0089* (2013.01); *C07C 7/20* (2013.01); *C07C 17/389* (2013.01); *C07C 41/36* (2013.01); *C07F 7/1804* (2013.01); *C10L 3/10* (2013.01); *B01D 2253/20* (2013.01); *B01D 2253/204* (2013.01); *B01D 2256/18* (2013.01); *B01D 2257/11* (2013.01); *B01D 2257/2062* (2013.01); *B01D 2257/2064* (2013.01); *B01D 2257/2066* (2013.01); *B01D 2257/504* (2013.01); *B01D 2257/704* (2013.01); *B01D 2257/7022* (2013.01); *B01D 2257/7025* (2013.01); *Y02P 20/151* (2015.11)

(58) Field of Classification Search
CPC ......... C07C 41/36; C07C 17/389; C07C 7/20; C07C 43/043; C07C 19/043; C07C 19/03; C10L 3/10; B01D 2257/2064; B01D 2257/704; B01D 2257/504; B01D 2257/2062; B01D 2257/2066; B01D 2257/7022; B01D 2257/7025; B01D 2256/18; B01D 53/02; B01D 2253/20; B01D 2253/204; C07D 453/22; C07F 7/1804; B01J 20/226; B01J 20/22; Y02P 20/151; C01B 23/0089; Y02C 20/20; Y02C 20/40

See application file for complete search history.

(56) References Cited

U.S. PATENT DOCUMENTS

2010/0047709 A1 2/2010 Echigo et al.

OTHER PUBLICATIONS

Cram et al., 1985, J. Am. Chem. Soc., 107 (8), 2574.*
Cram et al. abstract, caplus an 1985:204025.*
Guerrero et al., "From mononuclear to polynuclear macrocyclic or macroacyclic complexes," *Coordination Chemical Reviews*, vol. 139, pp. 17-243, Feb. 1995.
Hartmann et al., "Chemical sensors with receptors: influence of different structures of cavitands on the detection of solvent vapours," *GIT Labor-Fachzeitschrift*, 41(12): 1168-1171, 1997.
Hill et al., "Substituent effects on xenon binding affinity and solution behavior of water-solublecryptophanes," *J. Am. Chem. Soc.*, 131(8): 3069-3077, Mar. 4, 2009.
International Search Report issued for International Application No. PCT/US2013/033612 dated Jan. 14, 2014.
Jain et al., "Chemistry of calix [4] resorcinarenes," *Russian Chemical Reviews*, 80(1): 75-102, Jan. 2011.
Kane et al., "Many simple molecular cavitands are intrinsically porous (zero-dimensional pore) materials," *Chemistry of Materials*, 27(21): 7337-7354, Oct. 1, 2015.
Klimova et al., "Synthesis of novel supramolecular complexes from fullerene C60 and two new cavitands," *Fullerenes, Nanotubes, and Carbon Nanostructures*, 12(1-2): 175-179, Aug. 2004.
Lara-Ochoa et al., "A new tubular arrangement of a dimethylsilyl bridged calix[4]resorcinarene," *Supramolecular Chemistry*, 11(4): 263-273, Jan. 1999.

(Continued)

Primary Examiner — Sun Jae Yoo
(74) Attorney, Agent, or Firm — Klarquist Sparkman, LLP

(57) ABSTRACT

Cavitand compositions that comprise void spaces are disclosed. The void spaces may be empty, which means that voids are free of guest molecules or atoms, or the void spaces may comprise guest molecules or atoms that are normally in their gas phase at standard temperature and pressure. These cavitands may be useful for industrial applications, such as the separation or storage of gasses. Novel cavitand compounds are also disclosed.

15 Claims, 19 Drawing Sheets

(56) References Cited

OTHER PUBLICATIONS

Liu et al., "High-definition self-assemblies driven by the hydrophobic effect: synthesis and properties of a supramolecular-nanocapsule," *Chem. Commun. (Camb.)*, No. 32, 2709-3716, Jun. 6, 2008.

Misztal et al., "Design and synthesis of a cavitand pillar for MOFs," *Supramolecular Chemistry*, 26(3-4): 151-156, Sep. 9, 2013.

Naumann et al., "Expanding cavitand chemistry: the preparation and characterization of cavitands with n≥4," *Eur. J. Chem.*, 7(8): 1637-1645, Apr. 17, 2001.

Nguyen et al., "Guest binding drives reversible atropisomerism in cavitand hosts," *Chem. Eur. J.*, 15(24): 5892-5895, Jun. 8, 2009.

Vincenti et al., "Gas-phase interactions of calixarene- and resocinarene cavitands with molecular guests studied by mass spectrometry," *International Journal of Mass Spectrometry*, 214(1): 23-26, Feb. 15, 2002.

Yebeutchou et al., "Highly selective monomethylation of primary amines through host-guest product sequestration," 131(7): 2452-2453, Jan. 29, 2009.

Zhu et al., "Anion binding to resocinarene-based cavitands: the importance of C-H--anion interactions," *Angewandte Chemie*, International Edition, 47(4): 788-792, Jan. 8, 2008.

\* cited by examiner empty MeHSiMe$_2$    CH$_2$Cl$_2$@MeHSiMe$_2$

R = H, Me, NO$_2$
R' = H, Me, Et, i-Bu, Ph
Y = CH$_2$, SiMe$_2$

R • R' • Y • 2 = #*compounds*
3 • 5 • 2 • 2 = 60 rccc rctt

CAVITAND COMPOSITIONS AND METHODS OF USE THEREOF

CROSS REFERENCE TO RELATED APPLICATIONS

This application is a divisional of U.S. application Ser. No. 14/387,317, filed Sep. 23, 2014, which is the U.S. National Stage of International Application No. PCT/US2013/033612, filed Mar. 22, 2013, which was published in English under PCT Article 21(2), which in turn claims the benefit of priority of U.S. Provisional Application No. 61/614,967, filed Mar. 23, 2012; U.S. Provisional Application No. 61/765,600, filed Feb. 15, 2013; and U.S. Provisional Application No. 61/799,037, filed Mar. 15, 2013, which are incorporated herein in their entirety.

Any foregoing applications and all documents cited therein or during their prosecution ("application cited documents") and all documents cited or referenced in the application's cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention Citation or identification of any document in this application is not an admission that such document is available as prior art to the present invention.

BACKGROUND

The industrial importance and broad applicability of microporous materials (See Rouquerol, J. et al., *Pure & Appl. Chem.* 66, 1739-1758 (2004).) has long motivated the search for new crystalline materials exhibiting porosity or inclusion behavior. Inorganic zeolites, activated carbons and aluminum phosphates ($AlPO_4$) play vital roles in commercial applications (separations, catalysis, ion exchange) but are limited in their synthetic variability. (See Wilson et al., *J. Am. Chem. Soc.* 104, 1146-1147 (1982)).

For decades, however, it has been recognized that microporous molecule based materials may be particularly advantageous as the power of molecular/organic synthetic chemistry can be brought to bear on materials-oriented synthesis. Werner clathrates (see Powell, H. M., *J. Chem. Soc.* 61-73 (1948); Allison, S. A. & Barrer, R. M., *J. Chem. Soc. A* 1717-1723 (1969)), Dianin's compound (see Dianin, A. P., *J. Russ. Phys. Chem. Soc.* 36, 1310-1319 (1914); Barrer, R. M.; Shanson, V. H., *J. Chem. Soc. Chem. Commun.* 1976, 333-334), TPP (see Allcock, H. R., *J. Am. Chem. Soc.* 86, 2591-2595 (1964); Allcock, H. R., et al., *Inorg. Chem.* 25, 41-47 (1986)) and hydrogen-bonded 3D networks (see Brunet, P., et al., *J. Am. Chem. Soc.* 119, 2737-2738 (1997)) to name a few, are notable examples of discrete molecule microporous materials and have been integral in establishing the contemporary field of "crystal engineering". (See Desiraju, G. R., *Angew. Chem. Int. Ed.* 46, 8342-8356 (2007)).

The confluence of interest in the crystal engineering of molecular materials, porous inorganic materials, and metal-ligand self-assembly culminated in Robson's elucidation of the importance of crystalline coordination polymers (CPs) (see Robson, R., *Dalton Trans.* 5113-5131 (2008)) and metal-organic frameworks (MOFs) (see MacGillivray, L. *Metal-Organic Frameworks: Design and Application*, John Wiley & Sons, Hoboken, N.J., (2010); Long, J. R. & Yaghi, O. M. *Chem. Soc. Rev.* 2009, 38, 1201-1507). It also has expanded to the development of covalent organic frameworks (COFs) (Cote, A. P., et al., Porous, Crystalline, Covalent Organic Frameworks. *Science* 310, 1166-1170 (2005)) and polymers of intrinsic microporosity (PIMs) (McKeown, N. B. & Budd, P. M. Polymers of Intrinsic Microporosity (PIMs), *Encyclopaedia of Polymer Science and Technology*, John Wiley & Sons, Hoboken, N.J., (2002)) among other scaffolds.

Discrete organic molecular cages (see Tozawa, T., et al., *Nat. Mater.* 8, 973-978 (2009)) that are incapable of close-packing have established the importance of intrinsically porous molecules (Holst, J. R., et al., *Nat. Chem.* 2, 915-920 (2010)) that have applicability in selective gas separations and sorption. Also, materials that exhibit "porosity without pores" (Barbour, L. J., *Chem. Commun.* 1163-1168 (2006)), possess molecule-sized voids, but no molecular scale channels leading to these spaces, so permeability is based upon the ability of the small molecules to diffuse through a barrier; thus by definition, these materials are not formally porous, e.g., calix[4]arenes.

Calix[n]arenes (Gutsche, D. C., *Calixarenes: An Introduction (Monographs in Supramolecular Chemistry* (Royal Society of Chemistry, London, 2008)) are a class of macrocycles that have, for decades now, received attention related to their concave, bowl-like shape, which offers a cavity for the complexation of small molecules. So calix[n]arenes and their derivatives exhibit a high propensity to form inclusion compounds in the solid state due to both stabilizing host-guest interactions, and they have the general inability to form close packed structures in pure form. (Atwood, J. L., *Science* 296, 2367-2369 (2002)). Numerous studies on p-tert-butylcalix[4]arene helped to elucidate the nature of these materials towards gas adsorption as the t-butyl groups provide an obstacle to efficient packing. (Atwood, J. L., *Science* 298, 1000-1002 (2002)). The remarkable gas inclusion properties of these materials has prompted the study of calix[4]resorcinarenes, and more specifically, cavitand derivatives.

Calix[4]resorcinarenes (Hogberg, A. G. D., *J. Am. Chem. Soc.* 102, 6046-6050 (1980)), synthesized by an acid-catalyzed condensation of resorcinols and aldehydes, maintain their bowl-like shape through hydrogen bonding and can be further reacted to yield cavitands via intramolecular linking of the phenolic groups. (Cram, D. J., *Science* 219, 1177-1183 (1983)). The propensity for cavitands to incorporate a guest unit in their cavity in the solid-state is virtually guaranteed: of the 110 cavitand crystal structures reported in the Cambridge Structural Database (CSD), none contain void space in their packing.

But cavitand crystal structures containing void spaces in crystal packing could provide useful compositions for industrial applications, such as, separations, catalysis, ion exchange. It is an object of this invention to produce cavitand crystal structures with void spaces that are suitable for industrial use.

SUMMARY OF THE INVENTION

The present invention relates to crystalline compositions of cavitands, cavitand compounds, and methods of using cavitands and cavitand compositions for certain industrial applications. Crystalline cavitand compositions of this invention may have characteristics, such as crystalline packing, that have not been observed in other cavitand compositions. Additionally, the crystalline cavitand compositions may comprise void spaces within the crystalline compositions.

Without limitation, a void space maybe a pore or cavity within the crystalline cavitand composition. The void spaces within the crystalline composition may be empty, i.e., free of any molecules or atoms. The void spaces within the crystalline composition may also comprise gas molecules or atoms, where a gas is defined as an atom or molecule that is normally in its gas phase at standard temperature and pressure conditions.

In an embodiment, the present invention relates to compositions comprising a compound of formula (I):

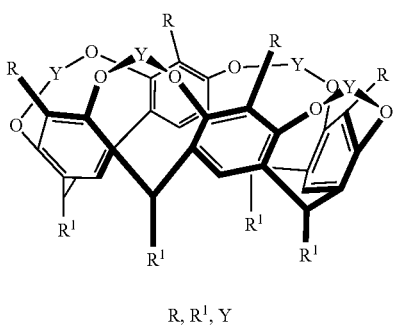

$R, R^1, Y$ and/or stereoisomers thereof; wherein
R is H, $C_1$-$C_6$ alkyl, halo, or $NO_2$;
$R^1$ is H, $C_1$-$C_6$ alkyl, Ph, ($C_1$-$C_6$ alkyl)$_x$Ph, (C(halo)$_3$)$_x$Ph, or (halo)$_x$Ph;
Y is —$CH_2$—, C($C_1$-$C_6$ alkyl)$_2$, or Si($C_1$-$C_6$ alkyl)$_2$; and
x is an integer from 1-3;
wherein the composition is in a crystalline form that comprises void spaces of at least 15 Å$^3$; and
wherein the void spaces are free of other atoms and molecules.

In an embodiment of the composition, for the compound of formula (I):
R is H, $CH_3$, Br, or $NO_2$;
$R^1$ is H, $CH_3$, $CH_2CH_3$, i-Bu, Ph, 4-$CH_3$Ph, 4-$CF_3$Ph, 3,5-($CF_3$)$_2$Ph, or 3,5-$F_2$Ph; and
Y is —$CH_2$—, —Si($CH_3$)$_2$—, —Si($CH_3CH_2$)$_2$—, or —Si(i-Pr)$_2$—.

In another embodiment of the composition, for the compound of formula (I):
R is H;
$R^1$ is H, $CH_3$, i-Bu, Ph, 4-$CF_3$Ph, 3,5-($CF_3$)$_2$Ph, or 3,5-$F_2$Ph; and
Y is —$CH_2$—, —Si($CH_3$)$_2$—, —Si($CH_3CH_2$)$_2$—, or —Si(i-Pr)$_2$—;
wherein $R^1$ is not $CH_3$ when Y is —$CH_2$—, —Si($CH_3$)$_2$—, or Si($CH_3CH_2$)$_2$; and
wherein $R^1$ is not Ph when Y is —$CH_2$—.

In another embodiment of the composition, for the compound of formula (I):
R is $CH_3$;
$R^1$ is H, $CH_3$, $CH_2CH_3$, i-Bu, 3,5-($CF_3$)$_2$Ph; and
Y is —$CH_2$—, —Si($CH_3$)$_2$—, Si($CH_2CH_3$)$_2$, or —Si(i-Pr)$_2$—;

wherein for $R^1$ is not H when Y is —$CH_2$—, —Si($CH_3$)$_2$—; and
wherein $R^1$ is not $CH_3$ when Y is —$CH_2$—.

In another embodiment of the composition, for the compound of formula (I):
R is $NO_2$;
$R^1$ is H or $CH_3$; and
Y is —$CH_2$—.

In another embodiment of the composition, for the compound of formula (I):
R is H, $CH_3$, or Br;
$R^1$ is H, $CH_3$, $CH_2CH_3$, Ph, or 4-$CH_3$Ph; and
Y is —$CH_2$—, —Si($CH_3$)$_2$—, or Si($CH_2CH_3$)$_2$.

In another embodiment of the composition, the compound of formula (I) is a compound of formula (Ia):

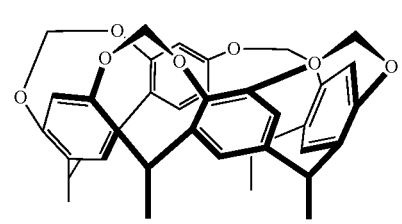

H, Me, $CH_2$ and/or stereoisomers thereof.

In another embodiment of the composition, the compound of formula (I) has a structure of formula (Ib):

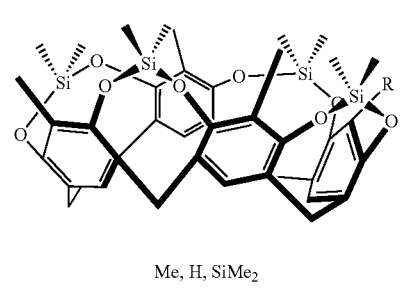

Me, H, SiMe$_2$ and/or stereoisomers thereof.

In other embodiments of the composition, the compound of formula (I) is selected from the following (R, $R^1$, Y):
(H, $CH_3$, $CH_2$); (H, i-Bu, $CH_2$); (H, 4-$CF_3$Ph, $CH_2$); (H, 3,5-$F_2$Ph, $CH_2$); ($CH_3$, 3,5-($CF_3$)$_2$Ph, $CH_2$); ($CH_3$, $CH_3CH_2$, $CH_2$); ($CH_3$, i-Bu, $CH_2$); ($NO_2$, H, $CH_2$); (H, H, Si($CH_3$)$_2$); (H, i-Bu, Si($CH_3$)$_2$); ($CH_3$, $CH_3$, Si($CH_3$)$_2$); ($CH_3$, $CH_3CH_2$, Si($CH_3$)$_2$); ($CH_3$, H, Si($CH_3CH_2$)$_2$); ($CH_3$, $CH_3$, Si($CH_3CH_2$)$_2$); (H, H, Si(i-Pr)$_2$); (H, $CH_3$, Si(i-Pr)$_2$); ($CH_3$, H, Si(i-Pr)$_2$); and ($CH_3$, $CH_3$, Si(i-Pr)$_2$).

The present invention also relates to cavitand compounds. In a specific embodiment, a cavitand compound has a structure of formula (II).

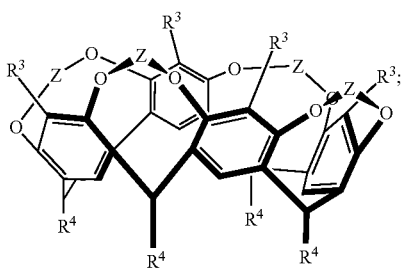

(II)

and stereoisomers thereof; wherein
$R^3$ is H, $CH_3$, or $NO_2$;
$R^4$ is H, $CH_3$, i-Bu, Ph, 4-$CF_3$Ph, 3,5-$(CF_3)_2$Ph or 3,5-$F_2$Ph;
Z is —$CH_2$—, —$Si(CH_3)_2$—, —$Si(CH_3CH_2)_2$—, or —$Si(i-Pr)_2$—.

An embodiment of formula (II), is a compound of formula (IIa):

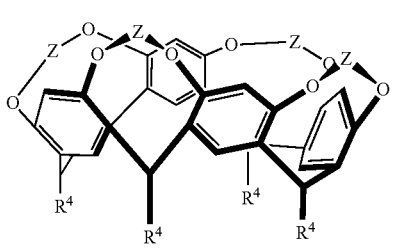

(IIa)

and/or stereoisomers thereof, wherein
$R^4$ is H, $CH_3$, i-Bu, Ph, 4-$CF_3$Ph, 3,5-$(CF_3)_2$Ph, or 3,5-$F_2$Ph; and
Z is —$CH_2$—, —$Si(CH_3)_2$—, —$Si(CH_3CH_2)_2$—, or —$Si(i-Pr)_2$—;
wherein $R^4$ is not $CH_3$ when Z is —$CH_2$—, —$Si(CH_3)_2$—, or $Si(CH_3CH_2)_2$; and
wherein $R^4$ is not Ph when Z is —$CH_2$—.

In an embodiment, the compound of formula (IIa) is selected from the following ($R^4$, Z):
($CH_3$, $CH_2$); (i-Bu, $CH_2$); (4-$CF_3$Ph, $CH_2$); (3,5-$F_2$Ph, $CH_2$); (H, $Si(CH_3)_2$); (i-Bu, $Si(CH_3)_2$); (H, $Si(i-Pr)_2$); (3,5-$(CF_3)_2$Ph, $CH_2$); and ($CH_3$, $Si(i-Pr)_2$).

An embodiment of formula (II), is a compound of formula (IIb):

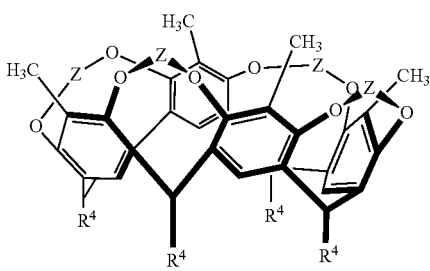

(IIb)

and/or stereoisomers thereof; wherein
$R^4$ is H, $CH_3$, $CH_2CH_3$, i-Bu, or 3,5-$(CF_3)_2$Ph; and
Z is —$CH_2$—, —$Si(CH_3)_2$—, $Si(CH_2CH_3)_2$, or —$Si(i-Pr)_2$—;

wherein $R^4$ is not H when Z is —$CH_2$— or —$Si(CH_3)_2$—; and
wherein $R^4$ is not $CH_3$ when Z is —$CH_2$—.

In an embodiment, the compound of formula (IIb) is selected from the following ($R^4$, Z):
(3,5-$(CF_3)_2$Ph, $CH_2$); ($CH_3CH_2$, $CH_2$); (i-Bu, $CH_2$); ($CH_3$, $Si(CH_3)_2$); ($CH_3CH_2$, $Si(CH_3)_2$); (H, $Si(CH_3CH_2)_2$); ($CH_3$, $Si(CH_3CH_2)_2$); (H, $Si(i-Pr)_2$); and ($CH_3$, $Si(i-Pr)_2$).

An embodiment of formula (II), is a compound of formula (IIc):

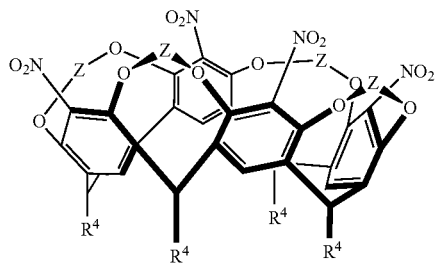

(IIc)

and/or stereoisomers thereof; wherein
$R^4$ is H, $C_1$-$C_6$ alkyl, Ph, ($C_1$-$C_6$ alkyl)$_x$Ph, (C(halo)$_3$)$_x$Ph, or (halo)$_x$Ph; and
Z is —$CH_2$—, C($C_1$-$C_6$ alkyl)$_2$, or Si($C_1$-$C_6$ alkyl)$_2$;
wherein x is an integer from 1-3.

In an embodiment, for the compound formula (IIc) $R^4$ is H or $CH_3$ and Z is $CH_2$. In another embodiment, $R^4$ is H and Z is $CH_2$.

The present invention also encompasses cavitand compositions comprising compounds of formulas (I) and/or (II) that further comprise gas guest molecules that may be complexed in the void spaces of the cavitand to form host-guest complexes.

The present invention also relates to compositions comprising a compound of formula (I):

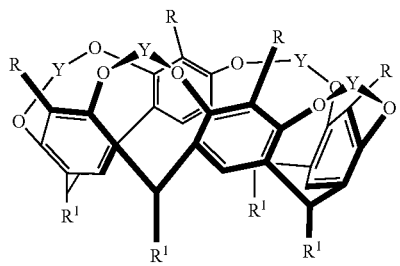

(I)

R, $R^1$, Y and/or stereoisomers thereof; wherein:
R is H, $C_1$-$C_6$ alkyl, halo, or $NO_2$;
$R^1$ is H, $C_1$-$C_6$ alkyl, Ph, ($C_1$-$C_6$ alkyl)$_x$Ph, (C(halo)$_3$)$_x$Ph, or (halo)$_x$Ph;
Y is —$CH_2$—, C($C_1$-$C_6$ alkyl)$_2$, or Si($C_1$-$C_6$ alkyl)$_2$; and
x is an integer from 1-3;
wherein the composition is a host-guest complex, where at least some of the void spaces of the composition comprise one or more guest gas molecules or atoms.

In certain embodiments, the guest gas is selected from one or more of acetylene, argon, krypton, xenon, carbon dioxide, methane, ethylene, ethane, propyne, propene, propane, fluoromethane, chloromethane, chloroethane, dimethylether, freons, gaseous fluorocarbons, methanethiol, oxygen, nitrogen, and bromomethane.

In certain embodiments, the guest gas is selected from one or more $C_1$ hydrocarbon gasses, $C_2$ hydrocarbon gasses, and $C_3$ hydrocarbon gasses.

In certain embodiments, the guest gas is a noble gas. In certain embodiments, the guest gas is argon, krypton, or xenon.

The compounds and compositions of the invention may be characterized by their ability to selectively complex gas molecules. This property is useful for gas separations, wherein two or more gasses may need to be separated in, for example, an industrial process.

Certain compositions of the invention are capable of forming a host-guest complex with one or more guest gas molecules within its void spaces; wherein the guest gas is selected from one or more $C_1$ hydrocarbon gasses, $C_2$ hydrocarbon gasses, and $C_3$ hydrocarbon gasses.

In an embodiment, the composition is characterized by forming a host-guest complex with one or more $C_1$ hydrocarbon gases selectively over one or more $C_2$ hydrocarbon gasses and/or $C_3$ hydrocarbon gases. In another embodiment, the composition is characterized by forming a host-guest complex with one or more $C_2$ hydrocarbon gases selectively over one or more $C_1$ hydrocarbon gasses and/or $C_3$ hydrocarbon gases. In another embodiment, the composition is characterized by forming a host-guest complex with one or more $C_3$ hydrocarbon gases selectively over one or more $C_1$ hydrocarbon gasses and/or $C_2$ hydrocarbon gasses.

In certain embodiments, the $C_1$ hydrocarbon gas is methane, the $C_2$ hydrocarbon gas is selected from one or more of ethane, ethylene, and acetylene; and the $C_3$ hydrocarbon gas is selected from one or more of propane, propene, and propyne.

In an embodiment, the composition is capable of forming a host-guest complex with one or more guest gas molecules within its void spaces, wherein the one or more guest gas molecule(s) is/are selected from $CH_3Cl$ and $CH_3CH_2Cl$, and wherein the composition is characterized by selectively forming a host-guest complex with $CH_3Cl$ over $CH_3CH_2Cl$ or $CH_3CH_2Cl$ over $CH_3Cl$.

In another embodiment, the composition is capable of forming a host-guest complex with guest gas molecules within its void spaces, wherein the one or more guest gas molecule(s) is/are selected from $CH_3Cl$ and $CH_3OCH_3$, and wherein the composition is characterized by selectively forming a host-guest complex with $CH_3Cl$ over $CH_3OCH_3$ or $CH_3OCH_3$ over $CH_3Cl$.

In another embodiment, the composition is capable of forming a host-guest complex with guest gas molecules within its void spaces, wherein the one or more guest gas molecule(s) is/are selected from the Ar, Xe, and Kr, and wherein the composition is characterized by selectively forming a host-guest complex with one of Ar, Xe, or Kr over the others.

In certain embodiments, the cavitand-gas, host-guest complex compositions may also be used for the confinement of gases at ambient temperatures that are at least the boiling points of the gases. In an embodiment, the ambient temperature is at least 10° C. greater than the boiling point of the gas. In another embodiment, the ambient temperature is room temperature or about 20° C. The property of gas confinement has particular utility for the separation of gases as well as the confinement and storage of gasses. In a particular embodiment, the confined and or separated gasses may be radioactive gasses. In an embodiment, the radioactive gas may be a radioactive isotope of xenon (Xe) and/or krypton (Kr).

The present invention also encompasses methods of using cavitands of the invention and cavitand compositions of the invention for industrial purposes, including, but not limited gas separations. In an embodiment, compositions comprising the cavitands of the invention may be used to separate one or more gasses from other gasses. In another embodiment, compositions comprising the cavitands of the invention may be used to separate one or more gasses from a solution.

The methods of the present invention are generally useful for the separation and confinement of gasses. In an embodiment, the present invention includes a method for gas separation comprising:
  (i) exposing a sample comprising two or more gasses to a composition of formula (I); and
  (ii) selectively forming a host-guest complex between the composition of formula (I) and one or more of the gasses from the sample.

In an embodiment, the two or more gasses are selected from acetylene, argon, krypton, xenon, carbon dioxide, methane, ethylene, ethane, propyne, propene, propane, fluoromethane, chloromethane, chloroethane, dimethylether, freons, gaseous fluorocarbons, methanethiol, oxygen, nitrogen, and bromomethane.

In an embodiment, the present invention relates to methods for the separation of hydrocarbon gasses. As a non-limiting illustration, hydrocarbon gasses may be separated on the basis of length, i.e., number of carbon atoms, structure, i.e., straight chained versus branched, or saturation, i.e., the separation of alkanes, alkenes, and/or alkynes. In an embodiment, compositions of the invention are capable of doing separations of hydrocarbons including, but not limited to, $C_1$ hydrocarbons, $C_2$ hydrocarbons, and $C_3$ hydrocarbons.

In an embodiment, the method comprises separating propane and propene. In another embodiment, the method comprises separating ethylene and ethane.

In another embodiment, the invention relates to the separation of gases containing functional groups. For example, the compositions of the invention may be used to separate haloalkanes or ethers that are normally in their gas phase at standard temperature and pressure. In an embodiment, the compositions are capable of separating dimethyl ether from chloromethane and/or chloroethane. In another embodiment, the compositions are capable of separating chloromethane and chloroethane.

The present invention also relates to a method of gas storage comprising:
  (i) exposing a sample comprising one or more gasses to an empty crystalline cavitand composition of the invention, and
  (ii) forming a host-guest complex between the composition and one or more gasses from (i) the gas;
      wherein the complex is capable of retaining at least 95% of the gas at an ambient temperature that is at least 10° C. greater than the boiling point of the gas.

In an embodiment, the ambient temperature is at least 10° C. greater than the boiling point of the gas. In another embodiment, the ambient temperature is room temperature or 20° C. The property of gas confinement has particular utility for the separation of gases as well as the storage of gasses, for example for toxic or dangerous gasses. In a particular embodiment, the confined and or separated gasses may be radioactive gasses. In an embodiment, the radioactive gas may be a radioactive isotope of xenon (Xe) and/or krypton (Kr).

In an embodiment, the present invention also relates to a process for making crystalline cavitand compositions, wherein the compositions comprise voids that are free of solvent molecules. In another embodiment, the present invention relates to a process for making crystalline cavitand compositions, wherein the compositions comprise voids that are free of any guest molecules, i.e., empty cavitand crystals. In another embodiment, the present invention relates to a process for making crystalline cavitand compositions, wherein the compositions comprise voids containing guest molecules or atoms within the voids, wherein the guest molecules are molecules or atoms that are in gas phase at standard temperature and pressure.

In an embodiment, a process for making empty cavitand compositions of the invention comprises:
  (i) forming a crystalline cavitand composition;
  (ii) heating the crystals in order to eliminate any molecules that are in the void spaces of the crystalline cavitand compositions; and
  (iii) verifying that the void spaces of the composition are free of other molecules and atoms by analytical techniques known in the art.

In an embodiment, the analytical technique for verifying that void spaces are free of molecules is known in the art. In particular embodiments, the analytical technique is x-ray crystallography or thermogravimetric analysis (TGA).

It is further noted that the invention does not intend to encompass within the scope of the invention any previously disclosed product or composition, process of making the product or composition, or method of using the product or composition, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

These and other embodiments are disclosed or are apparent from and encompassed by the following Detailed Description.

DETAILED DESCRIPTION

Figure 1:
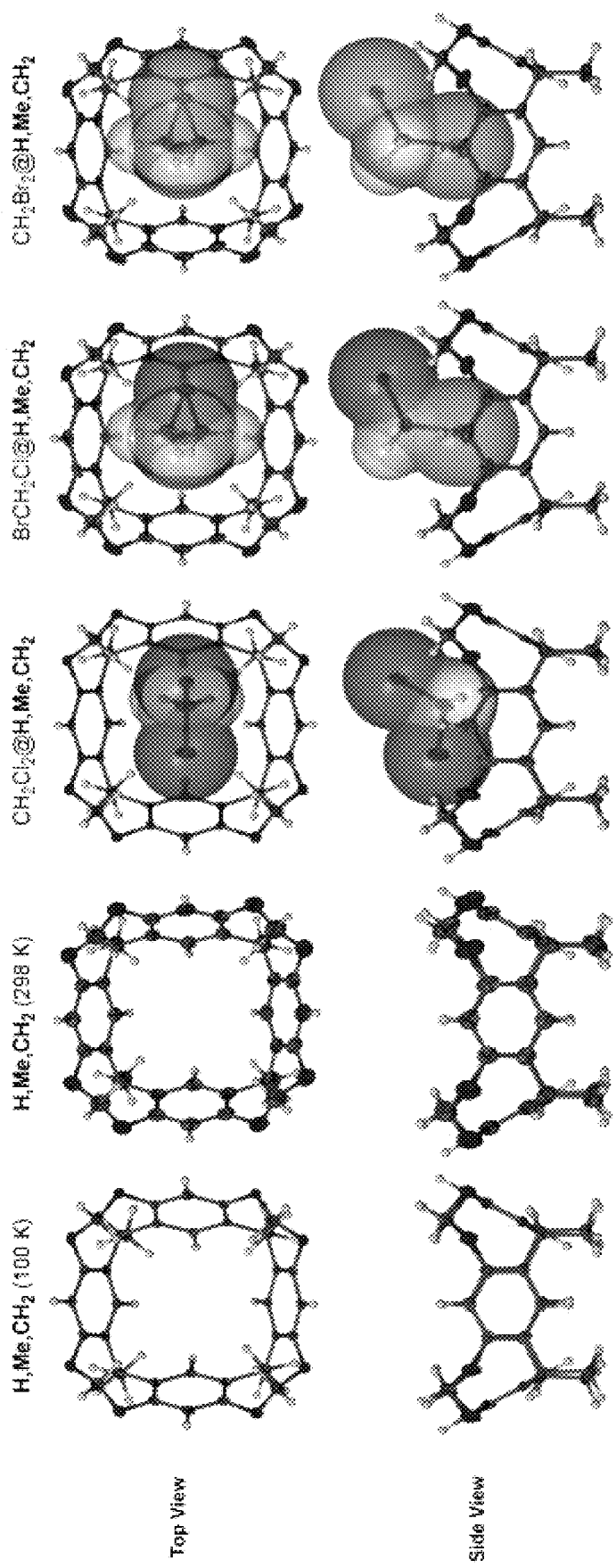
FIG. 1: Thermal ellipsoid plots of (left to right) empty formula (Ia) (@100 K), formula (Ia) (at 298 K), $CH_2Cl_2$@formula (Ia), $BrCH_2Cl$@formula (Ia), and $CH_2Br_2$@formula (Ia) at 50% probability level.

The cavitand compositions described herein, provide for crystalline structures that contain void spaces. These void spaces are capable of the selective uptake of certain chemical compounds, but not others. The cavitand compositions of the present invention open up cavitand chemistry for new industrial applications, such as gas separations, where there is demand for new efficient methods.

In an embodiment, the present invention relates to compositions comprising a compound of formula (I):

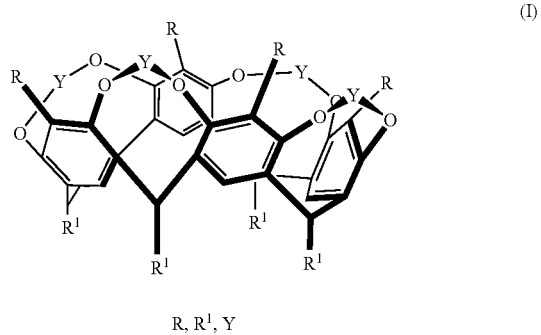

R, R$^1$, Y and/or stereoisomers thereof; wherein
R is H, C$_1$-C$_6$ alkyl, halo, or NO$_2$;
R$^1$ is H, C$_1$-C$_6$ alkyl, Ph, (C$_1$-C$_6$ alkyl)$_x$Ph, (C(halo)$_3$)$_x$Ph, or (halo)$_x$Ph;
Y is —CH$_2$—, C(C$_1$-C$_6$ alkyl)$_2$, or Si(C$_1$-C$_6$ alkyl)$_2$; and
x is an integer from 1-3;
wherein the composition is in a crystalline form that comprises void spaces of at least 15 Å$^3$; and
wherein the void spaces are free of other atoms and molecules.

Cavitands of formula (I), as described herein, may also be referred to by the R, R$^1$, and Y groups as R,R$^1$,Y. For example, a cavitand of formula (I), wherein R is H, R$^1$ is CH$_3$, and Y is CH$_2$ could alternately be referred to as H,Me,CH$_2$, or similar equivalents.

The void spaces of the crystalline compositions can vary in size. In an embodiment, the void space is greater than 15 Å$^3$. In an embodiment, the void space is greater than 20 Å$^3$. In an embodiment, the void space is greater than 25 Å$^3$.

In another embodiment, the void space is greater than 50 Å$^3$. In certain embodiments the void space can range from about 15 Å$^3$ to about 500 Å$^3$, 15 Å$^3$ to about 400 Å$^3$, 15 Å$^3$ to about 300 Å$^3$, 15 Å$^3$ to about 200 Å$^3$, 15 Å$^3$ to about 100 Å$^3$, 15 Å$^3$ to about 50 Å$^3$, or 15 Å$^3$ to about 25 Å$^3$.

In other embodiments, the void space can range from about 20 Å$^3$ to about 500 Å$^3$, 20 Å$^3$ to about 400 Å$^3$, 20 Å$^3$ to about 300 Å$^3$, 20 Å$^3$ to about 200 Å$^3$, 20 Å$^3$ to about 100 Å$^3$, 20 Å$^3$ to about 50 Å$^3$, or 20 Å$^3$ to about 25 Å$^3$.

In other embodiments, the void space can range from about 25 Å$^3$ to about 500 Å$^3$, 25 Å$^3$ to about 400 Å$^3$, 25 Å$^3$ to about 300 Å$^3$, 25 Å$^3$ to about 200 Å$^3$, 25 Å$^3$ to about 100 Å$^3$, or 25 Å$^3$ to about 50 Å$^3$.

In other embodiments, the void space can range from about 50 Å$^3$ to about 500 Å$^3$, 50 Å$^3$ to about 400 Å$^3$, 50 Å$^3$ to about 300 Å$^3$, 50 Å$^3$ to about 200 Å$^3$, or 50 Å$^3$ to about 100 Å$^3$.

In order to determine whether the void spaces of compositions of the invention are free of other atoms or molecules, analytical techniques such as thermogravimetric analysis (TGA) or x-ray crystallography may be used. For TGA, the composition is considered empty if there is no mass loss upon heating up to the sublimation temperature of the composition.

No mass loss in the context of TGA for compositions of the present invention is intended to include no more than about 20%, 15%, 10%, 5%, 3%, 2%, 1%, 0.5%, 0.2%, 0.1%, or no detectable mass loss.

In certain embodiments of the present invention, the TGA of cavitand compositions yields a weight loss of from about 0% to about 20%; about 0% to about 15%, about 0% to about 10%, about 0% to about 5%, about 0% to about 2%, about 0% to about 1%, about 0% to about 0.5%, about 0% to about 0.2%, or about 0% to about 0.1% of the composition up to the compositions sublimation temperature.

In an embodiment, the present invention relates to compositions comprising a compound of formula (I), as described above, but where at least some of the void spaces of the composition comprise one or more guest gas molecules. The guest molecules contained within the void spaces are typically in a gas phase at standard temperature and pressure. The resultant complexes may be described as, for example, host-guest complexes, cavitand-guest complexes, or cavitand-gas complexes. In certain embodiments, the ratio of gas to cavitand is from about 0.1 to 2.0, 0.1 to 1.0, 0.1 to 0.8, 0.1 to 0.5, 0.1 to 0.3, 0.3 to 2.0, 0.3 to 1.0, 0.3 to 0.8, 0.3 to 0.5, 0.5 to 2.0, 0.5 to 1.0, 0.5 to 0.8, 0.8 to 2.0, 0.8 to 1.0, or 1.0 to 2.0.

In certain embodiments, the guest gas is selected from one or more of acetylene, argon, krypton, xenon, carbon dioxide, methane, ethylene, ethane, propyne, propene, propane, fluoromethane, chloromethane, chloroethane, dimethylether, freons, gaseous fluorocarbons, methanethiol, oxygen, nitrogen, and bromomethane.

In certain embodiments, the gas phase molecule in the void space may comprise one or more of the following gasses: methane, ethane, ethene, ethyne, acetylene, propane, propene, propyne, butane, 1- or 2-butene, 1- or 2-butyne, bromomethane, chloromethane, chloroethane, fluoromethane, dimethyl ether, methane thiol, carbon dioxide, hydrogen, helium, argon, krypton, neon, xenon, nitrogen, oxygen, and other gas molecules generally contained in atmospheric air.

In certain embodiments, compounds of formula (I) can be more than one stereoisomer. For example, when R$^1$ is not a hydrogen atom (—H—), the carbon atom to which R$^1$ is bound is chiral. Chemical formula of the present invention can be generally assumed to include all possible stereoisomers, unless otherwise stated. In certain embodiments, compounds of the invention are the rccc or rctt stereoisomer. In certain embodiments, the chemical compounds of the invention may be stereoisomerically pure. Stereoisomeric purity may be defined as at least 90%, 95%, 97%, 99%, or 99.5% stereoisomeric purity as determined by analytical methods well known to those of ordinary skill in the art.

In an embodiment, when the compound of formula (I) can be one or more stereoisomer, the compositions of the present invention may comprise a compound of formula (I) that is a single stereoisomer. In another embodiment of the composition, the compound of formula (I) may be present as a mixture of stereoisomers.

Figure 12:
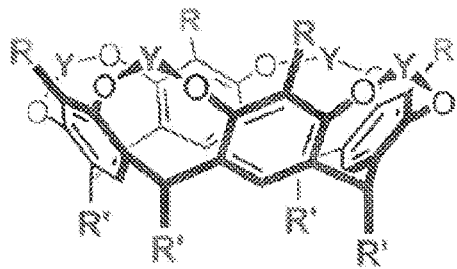
FIG. 12: Stereochemistry of cavitands of formula (I). The figure also depicts two stereoisomers, rccc and rctt, of formula (I) where R is H, $R^1$ is Ph, and Y is $CH_2$.
Figure 12:
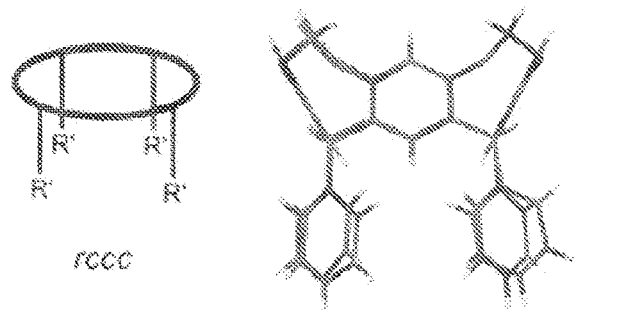
Figure 12:
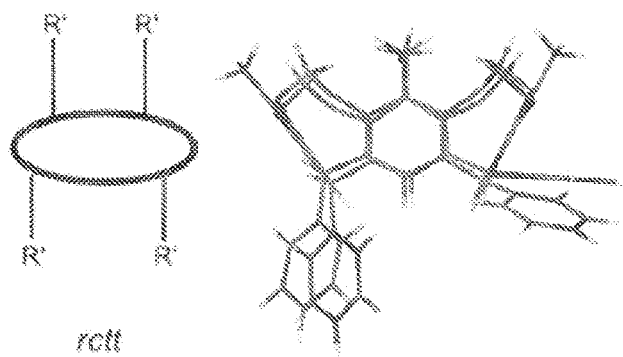
Figure 13:
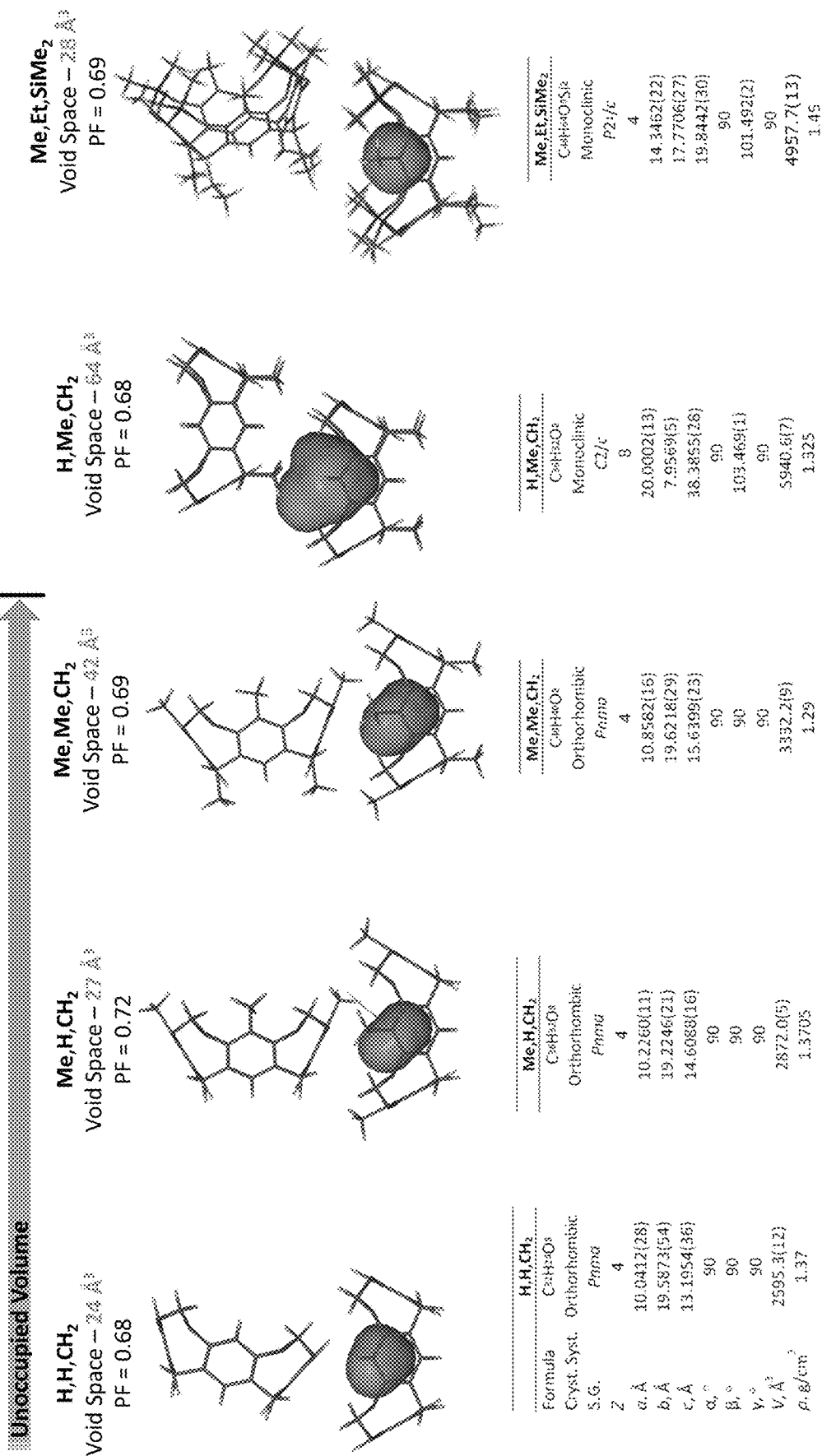
FIG. 13: Demonstration of the substituent modification effects for compositions comprising compounds of formula (I). Varying the R, $R^1$, Y groups affect the volume of the void space and crystal packing.
Figure 14:
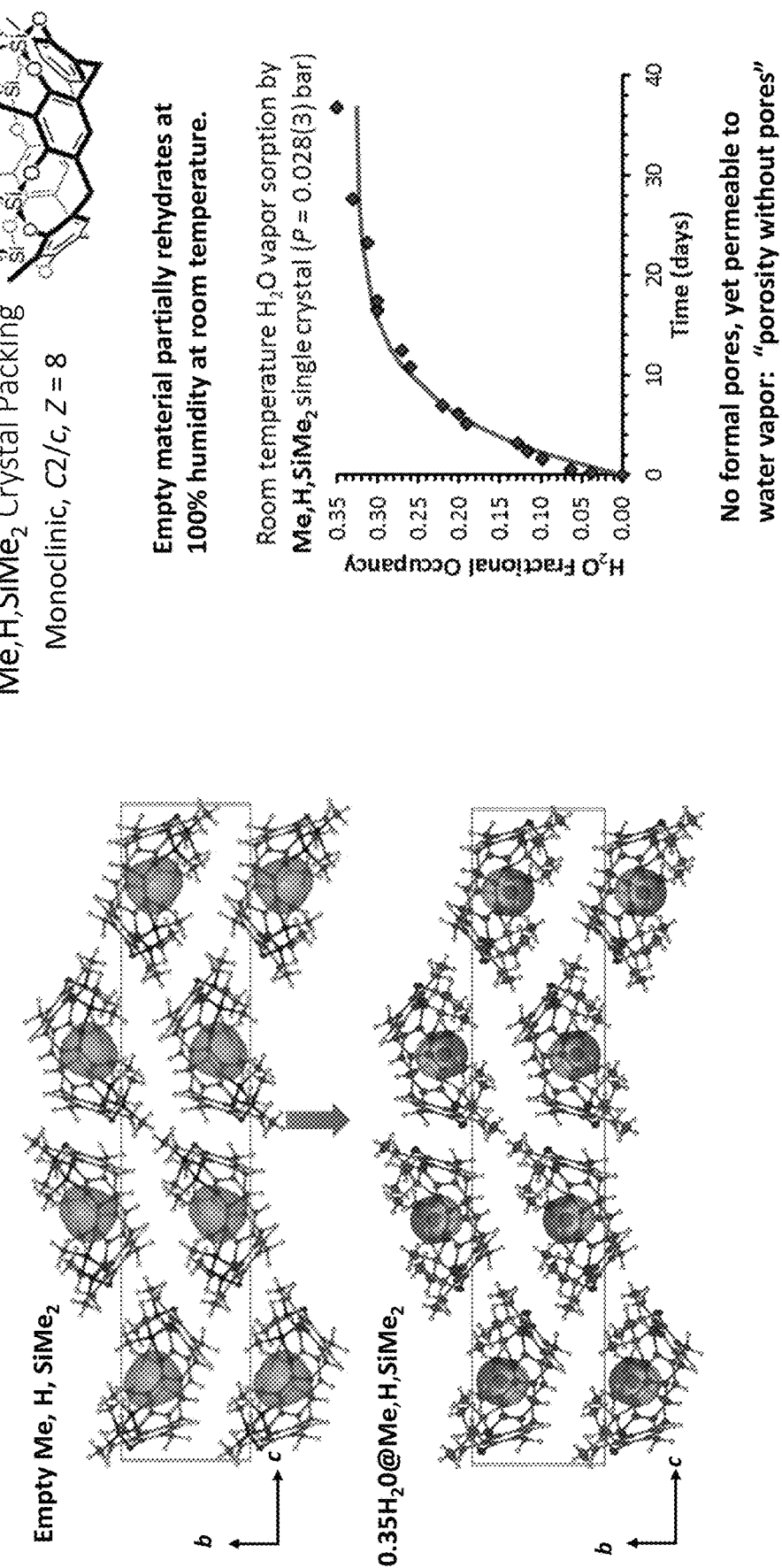
FIG. 14: Uptake of water vapor by a Me, H, SiMe$_2$ cavitand crystal composition.
Figure 15:
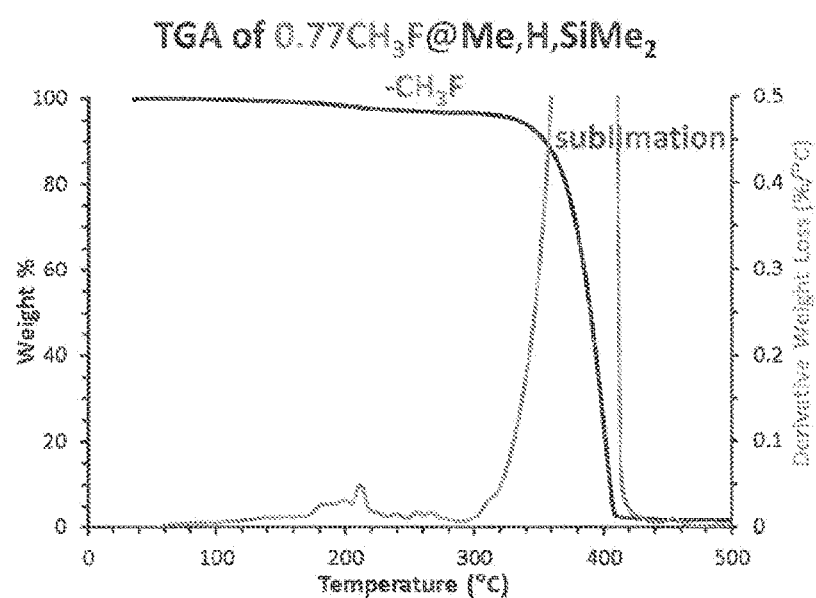
FIG. 15: TGA of 0.77$CH_3$@formula (Ib).
Figure 16:
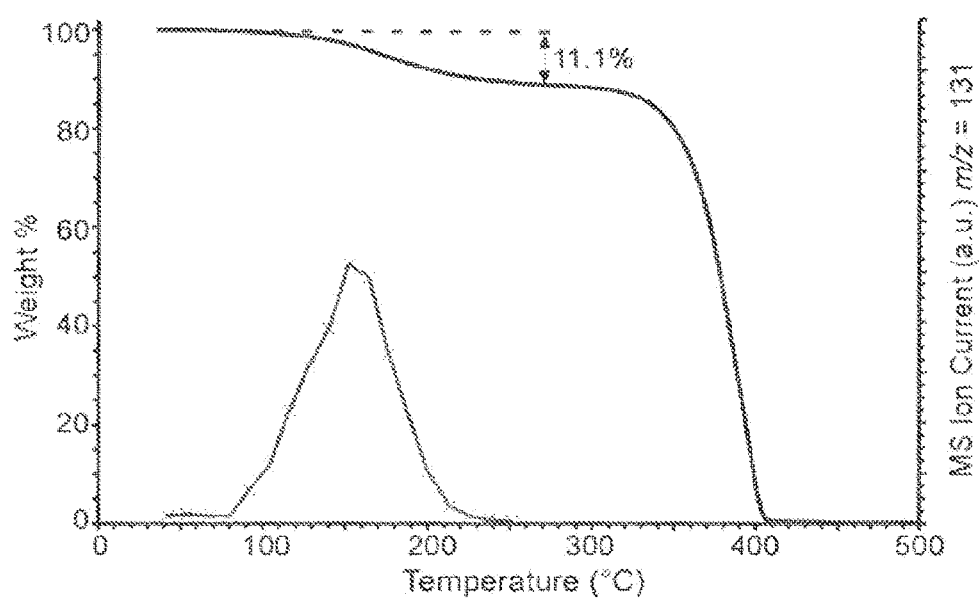
FIG. 16: Thermogravimetric analysis-mass spectrometry (TGA-MA) of 0.81Xe@formula (Ib).
Figure 17:
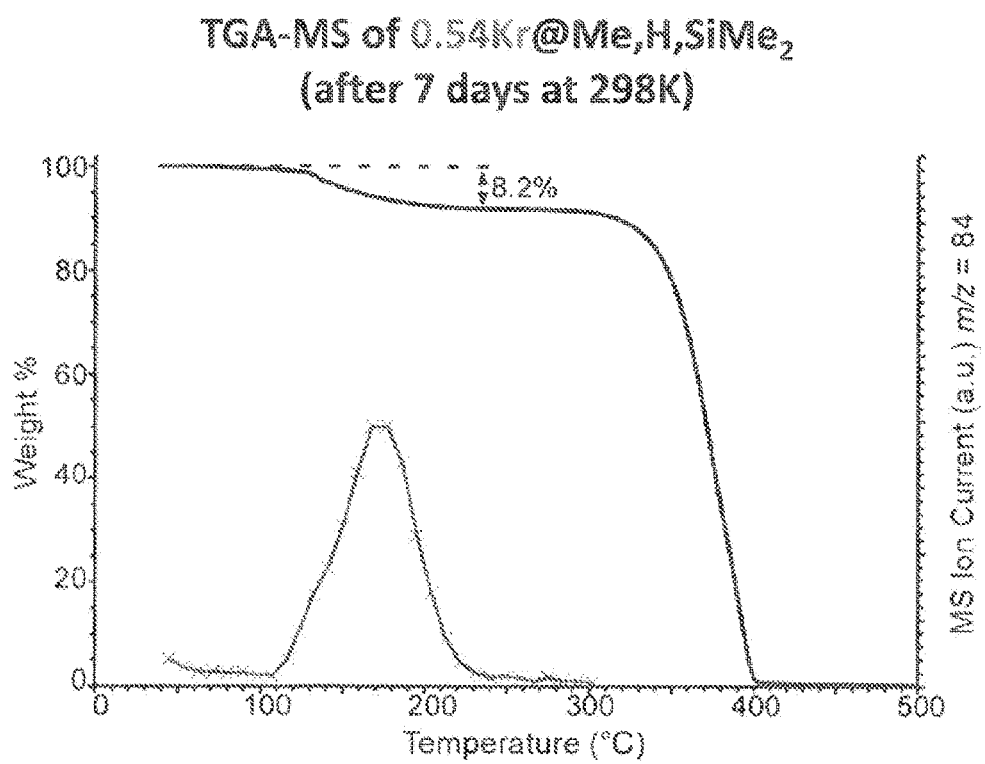
FIG. 17: Thermogravimetric analysis-mass spectrometry (TGA-MA) of 0.54Kr@formula (Ib) after 7 days at 298K.
Figure 18:
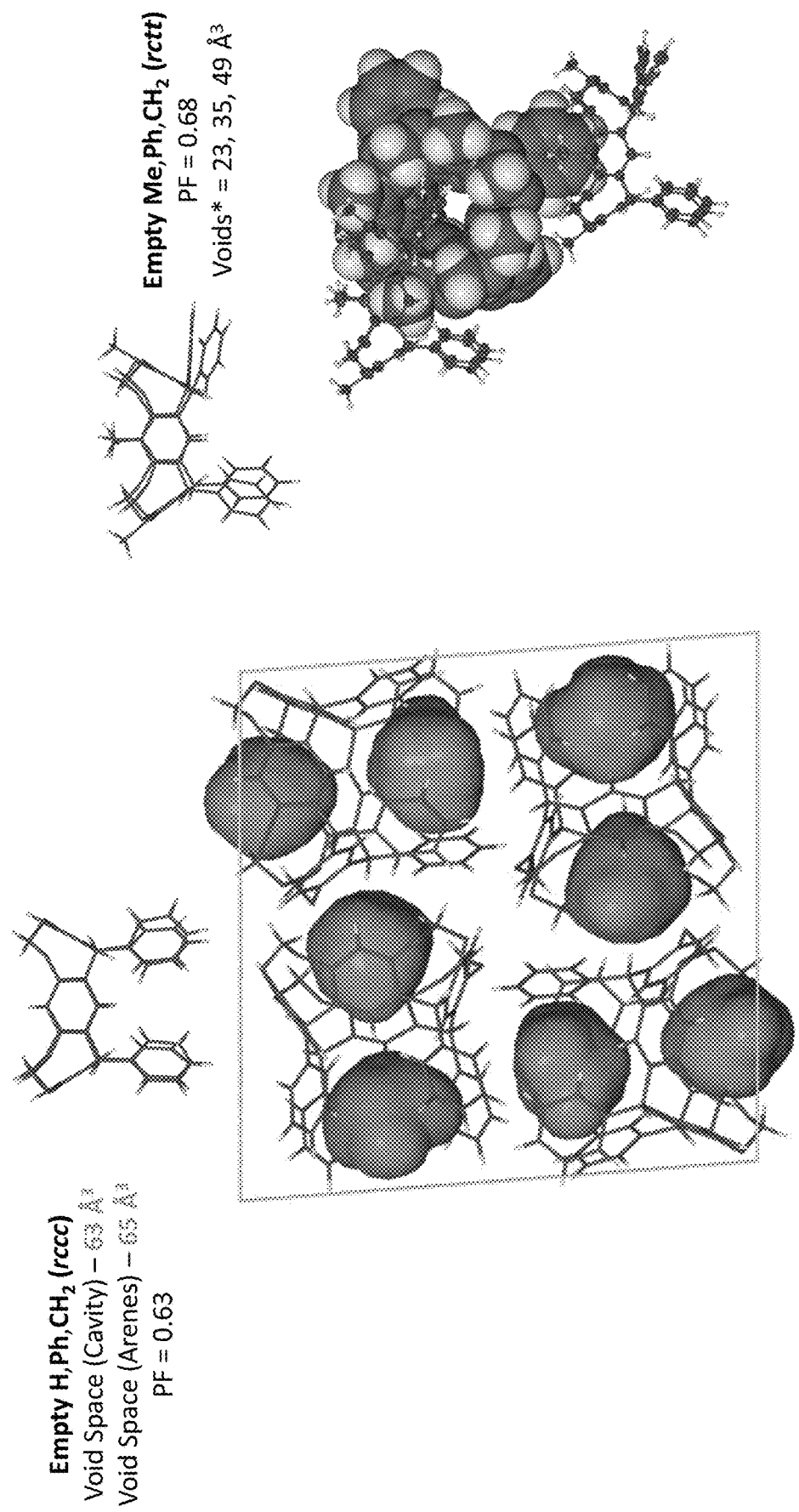
FIG. 18: Stereoisomeric effects on the void spaces of rccc-H,Ph,$CH_2$ and rctt-Me,Ph,$CH_2$.
Figure 19:
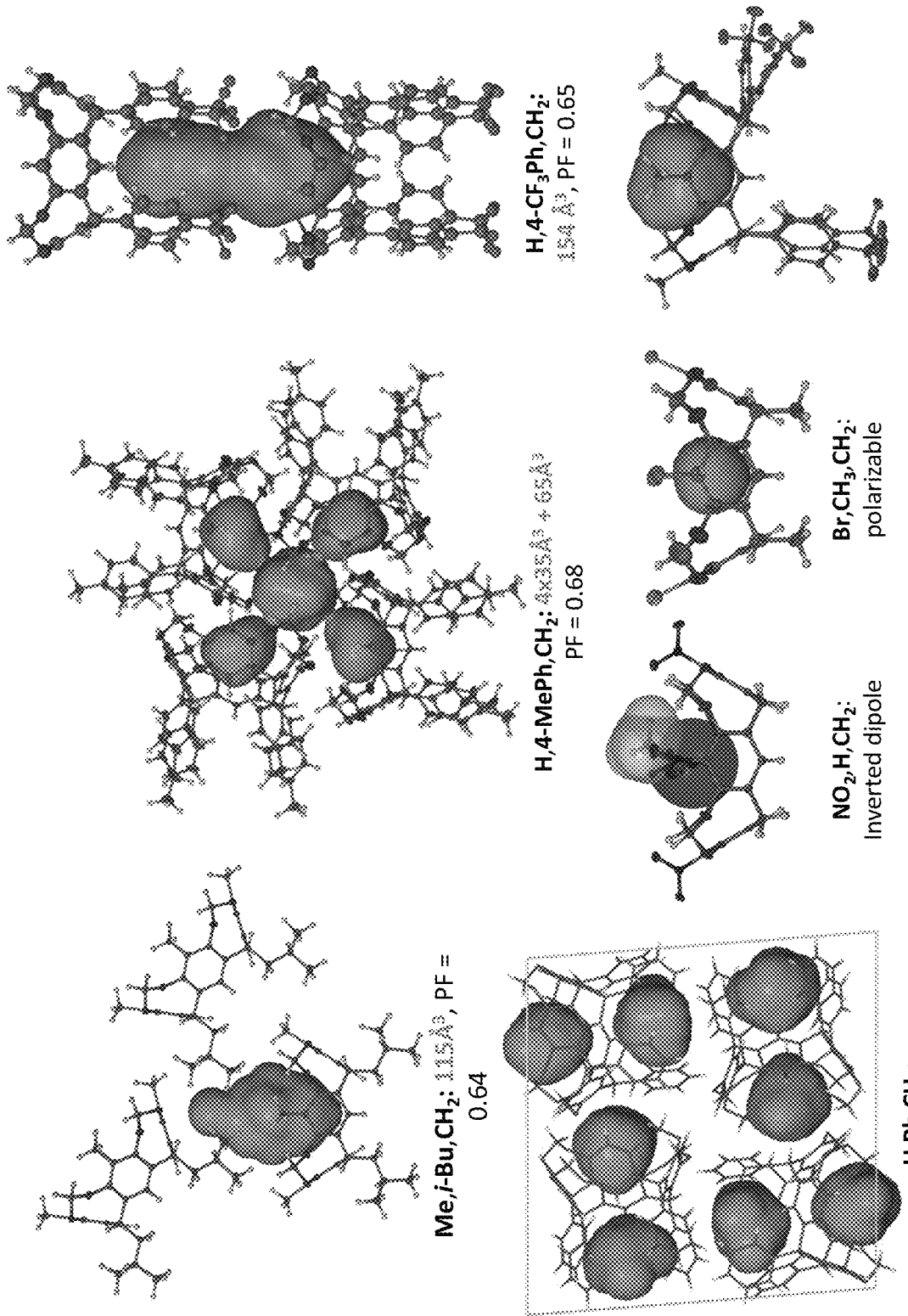
FIG. 19: Examples of guest-free cavitands: (Me,i-Bu, CH$_2$), (H,4-MePh,CH$_2$), (H,3-CF$_3$,CH$_2$), (H,Ph,CH$_2$), (NO$_2$,H,CH$_2$), (Br,CH$_3$,CH$_2$), (rctt-Me,4-CF$_3$, CH$_2$)

Convention regarding stereoisomerism of cavitands is illustrated in FIG. 12. In some embodiments, the compound of a compound of formula (I) is the rccc stereoisomer. In some embodiments, the stereochemistry of a compound of formula (I) is the rctt stereoisomer.

In an embodiment, the crystalline cavitand compositions of the present invention comprise void spaces that are empty. The empty void spaces may be accessible to certain molecules, but inaccessible to other molecules. This property allows the cavitand compositions of the present invention to selectivity take up guest molecules or atoms, for example, gas molecules or atoms. The guest molecules or atoms may be complexed and/or encapsulated within the void spaces of the composition. In an embodiment, the guest(s) is/are chemicals that are in a gas phase at standard temperature and pressure.

In another embodiment, the present invention relates to compositions comprising one or more cavitand compounds selected from formulas (I), (Ia), (Ib), (II), (IIa), (IIb), and (IIc).

Though the compositions of the present invention may not formally be porous, the void spaces or cavities within the compositions may nonetheless be accessible to small molecules and gases under conditions different from the low-temperature gas sorption experiments traditionally used to characterize porous material. This suggests that nanocrystal or mechanochemical approaches may offer opportunities to address potentially slow approach-to-equilibrium kinetics in these materials. Moreover, the systematic study of ultramicrocavity and nanospace structure, particularly in response to the presence of suitable atomic or small molecule probe species, offers opportunities to experimentally examine issues of structural flexibility and accommodation at the sub-angstrom length scale, features that cannot often be studied in large-pore materials.

It is revealed that crystalline compounds of formula (I) are highly capable of highly selective gas capture during crystallization (e.g., ethane vs. propane, chloromethane vs. dimethyl ether, ethylene vs. ethane, propene vs. propane, chloromethane vs. chloroethane, etc.) and confines highly volatile gases at unusually high temperatures. Moreover, while crystals are permeable to certain small molecules without any disruption of their single crystallinity, the kinetics of gas egress are qualitatively slow in comparison to open-pore materials, but are intriguingly highly guest dependent.

For gas uptake to form host-guest complexes of the present invention, may be achieved when the gas molecule or atom is in the gas phase. Alternatively, for gas uptake in certain embodiments, the gas molecule or atom may be in its liquid phase.

For gas storage, the host-guest complexes of the present invention are capable of retaining gases at ambient temperatures that are greater then the boiling point of the gas, but no more than the sublimation temperature of the composition. In certain embodiments, the host-guest complexes are capable of retaining gasses at an ambient temperature that is at least 5° C., 10° C., 20° C., 30° C., 40° C., 50° C., 75° C., 100° C., 150° C., 200° C., 250° C., or 300° C. greater than boiling point of the guest atom or molecule.

In certain embodiments, a guest may be retained within the host-guest complex at an ambient temperature of at least −150° C., −100° C., −50° C., −25° C., 0° C., 10° C., 20° C., 30° C., 40° C., 50° C., 75° C., 100° C., 150° C., or 200° C. In certain embodiments, the ambient temperature is from about −150° C. to −100° C., −100° C. to −50° C., −50° C. to −25° C., −25° C. to 0° C., 0° C. to 10° C., 0° C. to 20° C., 0° C. to 50° C., 20° C. to 50° C., 20° C. to 100° C., or 50° C. to 200° C.

In the host-guest complex, at the elevated temperatures described above, the guest gas is at least 50% retained, 75% retained, 80% retained, 85% retained, 90% retained, 95% reatine, 97% retained, 98% retained, 99% retained, 99.5% retained, or fully retained within instrument measurement limits.

For the first time, guest-free single crystal structures of numerous resorcinarene-derived cavitands have been synthesized. And it has been found that, as expected, in cases where it is sterically infeasible for peripheral functional groups to fully penetrate the bowl-like molecular cavity, empty molecule-sized ultramicrocavities (i.e. spheroidal pores), intrinsic to the molecule, are present in the structures.

Definitions

All definitions, as defined and used herein, should be understood to control over dictionary definitions, definitions in documents incorporated by reference, and/or ordinary meanings of the defined terms.

For purposes of this invention, the chemical elements are identified in accordance with the Periodic Table of the Elements, CAS version, Handbook of Chemistry and Physics, 67th Ed., 1986-87, inside cover.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "about," as used herein in reference to quantitative measurements, refers to the indicated value plus or minus 10%.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkenyl" as used herein means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "arylalkoxy" and "heteroalkoxy" as used herein means an aryl group or heteroaryl group, as defined herein, appended to the parent molecular moiety through an alkoxy group, as defined herein. Representative examples of arylalkoxy include, but are not limited to, 2-chlorophenylmethoxy, 3-trifluoromethylethoxy, and 2,3-methylmethoxy.

The term "arylalkyl" as used herein means an aryl group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylene," is art-recognized, and as used herein pertains to a bidentate moiety obtained by removing two hydrogen atoms of an alkyl group, as defined above.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylthio" as used herein means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "alkynyl" as used herein means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino" as used herein refers to radicals of both unsubstituted and substituted amines appended to the parent molecular moiety through a nitrogen atom. The additional groups appended to the nitrogen are independently hydrogen, alkyl, alkylcarbonyl, alkylsulfonyl, arylcarbonyl, or formyl. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl," as used herein means a phenyl group or a naphthyl group. The aryl groups of the present invention can be optionally substituted with 1, 2, 3, 4 or 5 substituents independently selected from the group consisting of alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "arylene," is art-recognized, and as used herein pertains to a bidentate moiety obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen.

The term "carbonyl" as used herein means a —C(O)— group.

The term "carboxy" as used herein means a —CO$_2$H group.

The term "cycloalkyl" as used herein means monocyclic or multicyclic (e.g., bicyclic, tricyclic, etc.) hydrocarbons containing from 3 to 12 carbon atoms that is completely saturated or has one or more unsaturated bonds but does not amount to an aromatic group. Examples of a cycloalkyl group include cyclopropyl, cyclobutyl, cyclopentyl, cyclopentenyl, cyclohexyl and cyclohexenyl.

The term "cycloalkoxy" as used herein means a cycloalkyl group, as defined herein, appended to the parent molecular moiety through an oxygen.

The term "cyano" as used herein means a —CN group.

The term "halo" or "halogen" means —Cl, —Br, —I or —F.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl", as used herein include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroaryl" as used herein include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo[b]thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, phosphinyl, silyl and silyloxy.

The term "heteroarylene," is art-recognized, and as used herein pertains to a bidentate moiety obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl) ethyl.

The term "hydroxy" as used herein means an —OH group.

The term "hydroxyalkyl" as used herein means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein means a —SH group.

The term "nitro" as used herein means a —NO$_2$ group.

The term "silyl" as used herein includes hydrocarbyl derivatives of the silyl ($H_3Si$—) group (i.e., (hydrocarbyl)$_3Si$—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers. A description of cavitand stereochemistry may be found in FIG. 12.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

As used herein, "amine" refers to organic compounds and functional groups that contain a basic nitrogen atom with a lone electron pair. Amines are derivatives of ammonia, wherein one or more hydrogen atoms have been replaced by a substituent such as, for example, an alkyl or aryl group. As used herein, the term "amine" also includes amino acids.

As used herein, "void," "voids," or "void spaces" refers to spaces within the crystalline cavitand compositions of the invention, and may be read to encompass terms of art including, but not limited to "cavities," "microcavities," "ultramicrocavities" "pores," and "micropores." For example, the void spaces may encompass one or more guest molecules or they may be empty.

As used herein, "thermogravimetric analysis" or "thermal gravimetric analysis" (TGA) is a method of thermal analysis in which changes in physical and chemical properties of materials are measured as a function of increasing temperature (with constant heating rate), or as a function of time (with constant temperature and/or constant mass loss). In the present invention, TGA may be used to determine whether a cavitand composition of the invention is free of molecules or atoms in the void spaces.

As used herein, "Standard conditions for temperature and pressure," "standard temperature and pressure," or "STP" are standard sets of conditions for experimental measurements established to allow comparisons to be made between different sets of data. The most used standards are those of the International Union of Pure and Applied Chemistry (IUPAC) and the National Institute of Standards and Technology (NIST), although these are not universally accepted standards. Other organizations have established a variety of alternative definitions for their standard reference conditions.

For example, in chemistry, IUPAC established standard temperature and pressure (informally abbreviated as STP) as a temperature of 273.15° K (0° C., 32° F.) and an absolute pressure of 100 kPa (14.504 psi, 0.986 atm, 1 bar). An unofficial, but commonly used, standard is standard ambient temperature and pressure (SATP) as a temperature of 298.15° K (25° C., 77° F.) and an absolute pressure of 100 kPa (14.504 psi, 0.986 atm).

NIST uses a temperature of 20° C. (293.15 K, 68° F.) and an absolute pressure of 101.325 kPa (14.696 psi, 1 atm). The International Standard Metric Conditions for natural gas and similar fluids are 288.15 K (59.00° F.; 15.00° C.) and 101.325 kPa.

In certain embodiments, the cavitand compositions of the present invention are free of conventional solvent molecules, where conventional solvents are limited to chemicals that are generally in a liquid phase at standard temperature and pressure.

Solvents described herein, include, but are not limited to, pentane, petroleum ether, hexane, heptanes, diethyl amine, diethyl ether, triethyl amine, tert-butyl methyl ether, cyclohexane, tert-butyl alcohol, isopropanol, acetonitrile, ethanol, acetone, methanol, methyl isobutyl ketone, isobutyl alcohol, 1-propanol, methyl ethyl ketone, 2-butanol, isoamyl alcohol, 1-butanol, diethyl ketone, 1-octanol, p-xylene, m-xylene, toluene, dimethoxyethane, benzene, butyl acetate, 1-chlorobutane, tetrahydrofuran, ethyl acetate, o-xylene, hexamethylphosphorus triamide, 2-ethoxyethyl ether, N,N-dimethylacetamide, diethylene glycol dimethyl ether, N,N-dimethylformamide, 2-methoxyethanol, pyridine, propanoic acid, water, 2-methoxyethyl acetate, benzonitrile, 1-methyl-2-pyrrolidinone, hexamethylphosphoramide, 1,4-dioxane, acetic acid, acetic anhydride, dimethyl sulfoxide, chlorobenzene, deuterium oxide, ethylene glycol, diethylene glycol, propylene carbonate, formic acid, 1,2-dichloroethane, glycerin, carbon disulfide, 1,2-dichlorobenzene, methylene chloride, nitromethane, 2,2,2-trifluoroethanol, chloroform, 1,1,2-trichlorotrifluoroethane, carbon tetrachloride, and tetrachloroethylene.

Examples of encapsulated guests in a cavitand composition of $(R,R^1,Y)$ Me,H,SiMe$_2$ are provided in table 1 below, including the properties of volume ($Å^3$) and boiling point (C.°) associated with these guest molecules.

TABLE 1

Summary of compositional, structural, and thermal analysis data for isostructural clathrates xguest@Me, H, SiMe$_2$ (x ≤ 1) and CH$_3$CCH@Me, H, SiMe$_2$•2CHCl$_3$, arranged by boiling point of the guest.

| Encapsulated Guest | bp (° C.) | $V_{guest}$ (Å$^3$) | Fractional Occupancy | | | $V_{cav}$ (Å$^3$) | PF$_{cav}$ | $V_{cell}$ (Å$^3$) | TGA | | $T_{max}$ (° C.) | $T_{max} - T_{bp}$ (° C.) |
|---|---|---|---|---|---|---|---|---|---|---|---|---|
| | | | SCXRD$^a$ | Day 0$^{b, c}$ | Day$^3$ 7$^{c, d}$ | | | | wt %$_{th}$ | wt %$_{exp}$ | | |
| none | n/a | n/a | n/a | n/a | n/a | 28 | 0 | 8230 (10) | 0 | 0 | 395(12)° | n/a |
| | | | | | | 28 | 0 | 8403 (2) | | | | |
| CH$_4$ | −162 | 28 | nm$^e$ | trace | 0 | — | — | — | — | nm | — | — |
| Ar | −186 | 28 | 0.29 (2)$^e$ | 0.29 (2)$^e$ | 0.27 (2)$^{d, e}$ | 41 | 0.7 | 8225 (1) | 1.5 | 1.7 | 129 | 315 |
| Kr | −153 | 35 | | 0.97$^{e, f}$ | 0.82$^{d, e, f}$ | | | | 9.8$^i$ | 9.5 | 139 | 292 |
| | | | 0.54 (3)$^e$ | 0.54 (3)$^{e, g}$ | 0.07 (1)$^{d, e, g}$ | 62 | 0.56 | 8223 (2) | | | | |
| Xe | −108 | 42 | 0.77 (3)$^e$ | 0.94$^{e, f}$ | 0.76$^{e, f}$ | 62 | 0.68 | 8252 (1) | 14.6$^i$ | 13.7 | 171 | 279 |
| | | | | 0.77 (3)$^e$ | 0.79 (2)$^{d, e, g}$ | | | | | | | |
| C$_2$H$_4$ | −104 | 40 | 0.41 (4)$^e$ | 0.41 (4)$^{e, g}$ | 0.43$^{e, g}$ | 65 | 0.62 | 8227 (1) | 1.5 | 1.0 | nm | nm |
| | | | | 0.062 (9) | 0.037 (1) | | | | | | | |

TABLE 1-continued

Summary of compositional, structural, and thermal analysis data for isostructural clathrates xguest@Me, H, SiMe$_2$ (x ≤ 1) and CH$_3$CCH@Me, H, SiMe$_2$•2CHCl$_3$, arranged by boiling point of the guest.

| Encapsulated Guest | bp (° C.) | $V_{guest}$ (Å$^3$) | Fractional Occupancy SCXRD[a] | Day 0[b, c] | Day$^3$ 7[c, d] | $V_{cav}$ (Å$^3$) | $PF_{cav}$ | $V_{cell}$ (Å$^3$) | TGA wt %$_{th}$ | wt %$_{exp}$ | $T_{max}$ (° C.) | $T_{max} - T_{bp}$ (° C.) |
|---|---|---|---|---|---|---|---|---|---|---|---|---|
| C$_2$H$_6$ | −89 | 45 | 0.72 (2), 0.62 (1)[e] | 0.72 (2)[e, g] 0.056 (5) | 0.74 (2)[d, e, g] 0.055 (4) | 67 | 0.67 | 8236 (1) | 2.7 | 2.8 | >129 | >218 |
| HC≡CH | −84 | 34 | nd | 0.055 (4) | 0 | nd | nd | nd | nd | nd | nd | nd |
| CH$_3$F | −78 | 32 | 0.80 (4), 0.45(11)[h] | 0.51 (5) | 0.27 (6) | 51 | 0.63 | 8218 (2) | 3.4 | 3.5 | 203 | 281 |
| CO$_2$ | −78[n] | 32 | 0.46 (6)[e] | 0.39[e, f] 0.46 (8)[e,g] | 0.35[e, f] 0.35 (5)[e, g] | 61 | 0.5 | 8214 (1) | 2.6 | 2.2 | 109 | 187 |
| CH$_3$CH=CH$_2$ | −48 | 57 | 0[e] | 0 | 0 | — | — | — | — | — | — | — |
| CH$_3$CH$_2$CH$_3$ | −42 | 62 | 0[e] | 0 | 0 | — | — | — | — | — | — | — |
| CH$_3$Cl | −24 | 44 | 0.90 (4), 1.0[j] | 1.0 | 0.84 | 62 | 0.71 | 8280 (2) | 6.2[i] | 6.4 | 233 | 257 |
| CH$_3$OCH$_3$ | −24 | 53 | 0.82 (4)[e] | 0.40 (2) | 0.35 (1) | 80 | 0.66 | 8349 (1) | 4.7 | 5.3 | 162 | 186 |
| CH$_3$C≡CH | −23 | 51 | 1.03 (2)[k] | 1.0[k] | 0 | 74 | 0.69 | 5003 (2)[k] | nm[k] | nd[k] | <25 | nm |
| CH$_3$Br | 4 | 49 | 0.91 (4) | nd | nd | 75 | 0.65 | 8307 (2) | 11.0 | nm[l] | 230 | 226 |
| CH$_3$SH | 6 | 46 | 0.83 (4) | nd | nd | 72 | 0.64 | 8278 (1) | nd | nd | nd | nd |
| CH$_3$CH$_2$Cl | 12 | 61 | 0.95 (1)[e] | 1.0 | 1.0 | 76 | 0.80 | 8446 (1) | 7.7[i] | 7.8 | 158 | 146 |
| CH$_2$Cl$_2$ | 40 | 59 | 0.85 (1) | nd | nd | 74 | 0.80 | 8378 (1) | 9.9[i] | 9.7 | 179 | 139 |
| CH$_3$I | 42 | 53 | 0.95 (3) | nd | nd | 77 | 0.69 | 8371 (1) | 15.6[i] | nm[l] | 210 | 168 |
| MeOH | 65 | 37 | 0.67 (8) | nd | nd | 52 | | 8230 (1) | 2.8 | 3.6 | 160 | 95 |
| BrCH$_2$Cl | 68 | 64 | 0.75 | 0.62[a] | nd | 82 | 0.78 | 8404 (1) | 11.7 | 9.6 | 177 | 109 |
| EtOH | 78 | 54 | 0.13 (4) | nd | nd | nm | nm | 8241 (2) | 0.8 | trace | nm | nm |
| CH$_3$CN | 81 | 44 | 0.96 (3) | nd | nd | 64 | 0.69 | 8244 (2) | 5.0 | nm[l] | nm | nm |
| CH$_2$Br$_2$ | 97 | 69 | 0[a] | 0.09[a] | nd | — | — | — | 2.0 | 2.2 | 115 | 18 |
| NO$_2$CH$_3$ | 101 | 51 | 0.95 (2) | nd | nd | 69 | 0.74 | 8277 (2) | 7.0 | nm[l] | nm | nm |
| H$_2$O | 100 | 18 | 0.29 (2)/ 0.40 (2)[m] | nd | nd | 28 | 0.65 | 8225 (25) | <0.5 | trace | nm | nm |
| I$_2$ | 113[n] | 60 | 0.06 (1) | nd | nd | nm | nm | 8242 (1) | 2.3 | 2.4 | nd | nd |

SCXRD = single crystal X-ray diffraction.
$V_{guest}$ = guest volume.
$V_{cav}$ = cavity volume estimated from SCRXD data (see Supporting Information).
$PF_{cav}$ = $V_{guest}/V_{cav}$, the packing fraction of the guest within the cavity.
$V_{cell}$ = unit cell volume at 100 K as measured by SCXRD (esds >2 Å$^3$ correspond to data from multiple crystals).
TGA = thermal gravimetric analysis (5° C./min.).
Wt % = theoretical (th) percent mass loss according to the SCXRD occupancy and experimentally observed (exp) percent mass loss.
$T_{max}$ = temperature of maximum rate of guest-loss (5° C./min. heating rate).
$T_{max} - T_{bp}$ = difference between the normal boiling point of the included guest and $T_{max}$.
Nd = not determined.
Nm = not meaningful.
[a]Crystals grown at room temperature directly from the included solvent (by evaporation) or from saturated CHCl$_3$ solutions of Me, H, SiMe$_2$ that were treated with excess guest (for CH$_3$OH, CH$_3$CH$_2$OH, I$_2$), or saturated with the gas of interest at 1 atm or the pressure indicated in footnote e.
[b]Unless otherwise noted, bulk powder samples were obtained by passing the the gas of interest (1 atm) through a chloroform solution of Me, H, SiMe$_2$ until dry.
[c]Occupancies determined by $^1$H NMR spectroscopy unless otherwise noted; esds are from three experiments.
[d]Occupancies after single crystals left for one week under ambient conditions, or as indicated as follows: (Kr, 11 days (TGA); Kr, 14 days at 100° C. (SCXRD); Xe, 19 days (TGA); Xe, 112 days (SCXRD); C$_2$H$_6$, 10 days (SCXRD); CO$_2$, 10 days (SCXRD).
[e]Occupancy detemrined by SCXRD. Crystals grown at room temperature from dry CHCl$_3$ under a pressure of gas (Ar ≤ 70 atm; Kr ≤ 70 atm; Xe ≤ 50 atm; C$_2$H$_4$ ≤ 45 atm; C$_2$H$_6$ ≤ 40 atm; CO$_2$ ≤ 60 atm; CH$_3$OCH$_3$ ≤ 6 atm; CH$_3$CH$_2$Cl < 2 atm; CH$_3$CH$_2$CH$_3$ > 20 atm; CH$_3$CH=CH$_2$, >20 atm).
[f]Occupancies est. by TGA.
[g]Occupancy determined by SCXRD at 100 K; the same crystal was used as for the Day 0 data.
[h]Crystal from the same batch preparation, but after 146 days (CH$_3$F) or 112 days (Xe) at ambient conditions.
[i]Based upon 100% ocupancy.
[j]Crystal from EtOAc solution.
[k]Crystallizes as the CH$_3$CCH@Me, H, SiMe$_2$•2CHCl$_3$ solvate, which loses gas at room temperature.
[l]Host sublimation occurs concommitantly with guest loss.
[m]Partial hydrates obtained from CHCl$_3$ (0.22 eq.) or acetone (0.38 eq.), or by room temperature rehydration of empty single crystals of Me, H, SiMe$_2$.
[n]Sublimation temperature.
[o]$T_{max}$(esd) of Me, H, SiMe$_2$ sublimation from empty or clathrate samples. The sublimation onset temperature is ca. 310° C.

The compositions of the invention may be characterized by an ability to differentially take up or form complexes with certain molecular or atomic guests in the void spaces of the crystals. The compositions of the present invention may be selective for the uptake of certain molecules over others, particularly molecules that are normally in gas phase at standard temperature and pressure. In some embodiments, a composition of the present invention is capable of selectively forming complexes with certain hydrocarbons and/or halogenated alkanes.

In certain embodiments, a composition of the invention may selectively take up 2-carbon hydrocarbon gases over 3-carbon hydrocarbon gases. In certain embodiments, a composition of the invention may selectively take up a 2-carbon hydrocarbon gas over another 2-carbon hydrocarbon gas. In certain embodiments, a composition of the invention may selectively take up a 1-carbon halogenated alkane over a 2-carbon halogenated alkane. In certain embodiments, the compositions of the present invention will selectively take up one or more hydrocarbon gasses, wherein the hydrocarbons may have 1, 2, or 3 carbon atoms, over carbon dioxide. In certain embodiments, the compositions of the present invention will selectively take up one or more hydrocarbon gasses, wherein the hydrocarbons may have 1, 2, or 3 carbon atoms, over dimethyl ether (DME). In other embodiments, the compositions of the present invention are suitable for selectively taking up gas molecules that are present in solvents.

In an embodiment, a complex of the present invention selectively takes up ethane over propane. In another embodiment, a composition of the present invention selectively takes up chloromethane over chloroethane. In another embodiment, a composition of the present invention selectively takes up chloromethane and/or chloroethane over dimethyl ether. In another embodiment, a complex of the present invention selectively takes up ethane gas over ethylene gas.

The selectivity of the compositions towards taking up certain molecules may be expressed by a selectivity coefficient, $K_{A:B}$. For any two gas guest molecules, A and B, the selectivity coefficient, $K_{A:B}$ may be of at least about 2, about 5, about 10, about 20, about 50, about 100, about 200, about 500, about 1000, about 2000, about 5000, or about 10,000.

For the uptake of gas molecules, the compositions of the present invention may exhibit a selectivity coefficient for $C_2$ hydrocarbon gasses over $C_3$ hydrocarbon gasses, or $C_3$ hydrocarbon gasses over $C_2$ hydrocarbon gasses, of at least about 2, about 5, about 10, about 20, about 50, about 100, about 200, about 500, about 1000, about 2000, about 5000, or about 10,000.

In other embodiments, the compositions of the present invention may exhibit selectivity of chloromethane over chloroethane, or chloroethane over chloromethane, of at least about 2, about 5, about 10, about 20, about 50, or about 100.

In another embodiment, the compositions of the present invention may exhibit selectivity of chloromethane and/or chloroethane over dimethyl ether, or dimethyl ether over chloromethane and/or chloroethane, of greater than about 2, about 5, about 10, about 20, about 50, about 100, about 200, about 500, about 1000, about 2000, about 5000, or about 10,000.

Synthesis of Cavitands of Formula (I)

In an embodiment, cavitand compositions comprising crystals of formula (I) may be synthesized by synthetic methods known to those of ordinary skill in the art.

While the synthesis of cavitands was known in the art, methods of synthesizing crystalline cavitand compositions comprising compounds of formula (I), wherein the void spaces of the cavitands are empty is believed new to the present invention. Described herein are methods of obtaining these empty void compositions.

In an embodiment of the invention, after workup and subsequent purification of a cavitand of formula (I), the resulting solid composition of formula (I) may be sublimed at high temperature and low pressure to give single crystals of empty cavitand.

Crystalline cavitand compositions of the invention may be analyzed by single crystal x-ray diffraction (SCXRD) at, for example, 100 and 298 K. Further analysis of this guest-free form of crystalline cavitand compositions of formula (I) using the MSRoll subroutine (Connolly, M. L. *J. Mol. Graph.* 1993, 11, 139) in XSEED (Barbour, L. J. *J. Supramol. Chem.* 2001, 1, 181) may show empty cavities of varying volumes, as described in the foregoing.

Table 2, below, contains data from a cavitand compositions of the invention that have been synthesized and subjected to analysis described herein. In general the compositions of the invention, including those described in table 2, may expand or contract depending on conditions such as temperature, pressure, and the degree of gas occupancy within cavitand compositions of the invention.

For the compositions described herein, the error associated with unit cell measurement to account for variations in the conditions and measurements is expected to be about ±3-5% for the lattice constants.

TABLE 2

Cavitand Composition Data

| Cavitand ($R, R^1, Y$) | Stereo isomer | New Complexes | a (Å) | b (Å) | c (Å) | α (°) | β (°) | γ (°) | V (Å³) | T (K) |
|---|---|---|---|---|---|---|---|---|---|---|
| H, H, $CH_2$ | rccc | Sublimed/Empty - Pnma | 10.0412 (28) | 19.5873 (54) | 13.1954 (36) | 90 | 90 | 90 | 2595.3 (12) | 100 (2) |
| | | $NO_2CH_3$ - $P2_1/m$ | 7.3877 (13) | 18.8361 (33) | 10.3891 (18) | 90 | 110.492 (2) | 90 | 1354.22 | 100 (2) |
| H, Me, $CH_2$ | rccc | $(CH_2Cl)_2$ - $P2_1/c$ | 12.1885 (17) | 8.3899 (12) | 30.8472 (42) | 90 | 90.702 (2) | 90 | 3154.21 | 100 (2) |
| | | $CH_2Br_2$ - Pbcm | 10.8853 (17) | 15.4820 (24) | 19.0058 (30) | 90 | 90 | 90 | 3202.98 | 100 (2) |
| | | $BrCH_2Cl$ - Pbcm | 10.8698 (9) | 15.2856 (13) | 19.0701 (16) | 90 | 90 | 90 | 3168.52 | 100 (2) |
| | | $CHCl_3$ - $P2_1/c$ | 15.2685 (12) | 14.4825 (12) | 15.3771 (12) | 90 | 106.082 (1) | 90 | 3267.21 | 100 (2) |
| | | 2EtOAc - P-1 | 10.6979 (11) | 10.7309 (11) | 35.6025 (41) | 98.001 (2) | 92.791 (2) | 111.251 (1) | 3750.28 | 100 (2) |
| | | $NO_2CH_3$ - P-1 | 8.2141 (151) | 10.4728 (196) | 19.5942 (366) | 102.325 (23) | 90.018 (24) | 108.811 (22) | 1554.42 | 100 (2) |
| | | Sublimed/Empty - C2/c | 20.0002 (13) | 7.9569 (5) | 38.3855 (28) | 90 | 103.469 (1) | 90 | 5940.6 (7) | 100 (2) |
| | | Sublimed/Empty - C2/c PXRD patterns of propene, propane, $CH_3Cl$, $CH_3CH_2Cl$, DME | 20.0499 (13) | 8.0240 (5) | 38.5526 (25) | 90 | 103.277 (1) | 90 | 6035.8 (7) | 298 (2) |
| H, Et, $CH_2$ | rccc | | | | | | | | | |
| H, i-Bu, $CH_2$ | rccc | | | | | | | | | |

TABLE 2-continued

Cavitand Composition Data

| Cavitand (R, R¹, Y) | Stereo isomer | New Complexes | a (Å) | b (Å) | c (Å) | α (°) | β (°) | γ (°) | V (Å³) | T (K) |
|---|---|---|---|---|---|---|---|---|---|---|
| H, Ph, CH$_2$ | rccc | 2CH$_3$I - P2$_1$/c | 22.3506 (34) | 10.7665 (16) | 21.6563 (33) | 90 | 115.703 (2) | 90 | 4695.69 | 100 (2) |
|  |  | 2NO$_2$CH$_3$ - P2$_1$ | 10.7171 (22) | 13.1962 (27) | 16.4770 (34) | 90 | 104.321 (4) | 90 | 2257.85 | 100 (2) |
|  |  | Sublimed/Empty - P-1 | 10.8153 (15) | 20.5120 (47) | 21.1317 (48) | 91.117 (3) | 104.804 (3) | 102.495 (3) | 4411.1 (X) | 100 (2) |
| H, Ph, CH$_2$ | rctt |  |  |  |  |  |  |  |  |  |
| H, 4-CF$_3$Ph, CH$_2$ | rccc | Sublimed/Empty - P1 | 10.7920 (26) | 13.9228 (33) | 18.8059 (45) | 97.069 (4) | 92.221 (4) | 110.743 (30) | 2612.08 | 100 (2) |
| H, 4-MePh, CH$_2$ | rccc | Sublimed/Empty - I-4 | 41.2138 (33) | 41.2138 (33) | 10.9003 (12) | 90 | 90 | 90 | 18515 (3) | 100 (2) |
| H, 3,5-F$_2$Ph, CH$_2$ | rccc | sublimed | insert data! |  |  |  |  |  |  |  |
| Me, 3,5-CF$_3$Ph, CH$_2$ | rctt | 4CHCl$_3$ - P2$_1$/c | 24.6086 (43) | 18.7299 (33) | 34.2758 (59) | 90 | 107.531 (2) | 90 | 15064.52 | 100 (2) |
|  |  | Sublimed/x(H$_2$O) - P2$_1$/c | 18.6310 (28) | 15.2825 (23) | 23.0555 (35) | 90 | 94.661 (2) | 90 | 6542.8 (X) | 100 (2) |
|  |  | Sublimed/Empty - P-1 | 11.9261 (81) | 14.8033 (101) | 20.0334 (137) | 70.627 (8) | 83.137 (9) | 81.696 (8) | 3291.9 (X) | 100 (2) |
| Me, H, CH$_2$ | rccc | CCl$_4$ - Pbca | 17.8176 (10) | 19.5344 (11) | 39.3215 (21) | 90 | 90 | 90 | 13686.09 | 100 (2) |
|  |  | 2NO$_2$CH$_3$ - P4nc | 15.4840 (14) | 15.4840 (14) | 7.1541 (6) | 90 | 90 | 90 | 1715.23 | 100 (2) |
|  |  | 2.5 (p-xylene) - P-1 | 11.7994 (11) | 18.7618 (18) | 21.9151 (21) | 111.616 (1) | 91.618 (2) | 91.271 (2) | 4505.76 | 100 (2) |
|  |  | Sublimed/Empty - Pnma | 10.2260 (11) | 19.2246 (21) | 14.6088 (16) | 90 | 90 | 90 | 2872.0 (5) | 100 (2) |
| Me, Me, CH$_2$ | rccc | Ether - P2$_1$/n | 9.2578 (4) | 22.2474 (10) | 18.3674 (9) | 90 | 98.929 (2) | 90 | 3737.14 | 100 (2) |
|  |  | EtOAc - P2$_1$/n | 9.4203 (8) | 21.9453 (18) | 18.3180 (15) | 90 | 97.794 (1) | 90 | 3751.92 | 100 (2) |
|  |  | p-xylene - P2$_1$/n | 9.7050 (9) | 21.0726 (20) | 19.2831 (18) | 90 | 96.013 (2) | 90 | 3921.88 | 100 (2) |
|  |  | p-xylene•x(p-xylene) - R3m | 35.0045 (35) | 35.0045 (35) | 9.5239 (10) | 90 | 90 | 120 | 10106.32 | 100 (2) |
|  |  | Sublimed/Empty - Pnma | 10.8582 (16) | 19.6218 (29) | 15.6399 (23) | 90 | 90 | 90 | 3332.2 (9) | 100 (2) |
| Me, Et, CH$_2$ | rccc | EtOAc - Pnma | 17.1572 (15) | 19.7201 (17) | 12.0228 (10) | 90 | 90 | 90 | 4067.81 | 100 (2) |
|  |  | m-xylene - Pnma | 17.4735 (17) | 19.7666 (19) | 12.2970 (12) | 90 | 90 | 90 | 4247.28 | 100 (2) |
|  |  | NO$_2$CH$_3$ - Pnma | 17.5037 (19) | 19.6988 (21) | 11.9868 (13) | 90 | 90 | 90 | 4133.07 | 100 (2) |
|  |  | Sublimed/Empty - P2$_1$/c | 11.8341 (10) | 24.0475 (20) | 14.0138 (12) | 90 | 110.772 (1) | 90 | 3728.8 (5) | 100 (2) |
| Me, i-Bu, CH$_2$ | rccc | EtOAc - Pnma | 10.5134 (11) | 19.9360 (20) | 24.1453 (25) | 90 | 90 | 90 | 5060.74 | 100 (2) |
|  |  | Sublimed/Empty - Pbca | 21.9246 (72) | 17.8065 (58) | 23.3378 (75) | 90 | 90 | 90 | 9111.09 | 100 (2) |
|  |  | Sublimed/Empty - Pnma | 19.3612 (13) | 19.2325 (13) | 12.9860 (9) | 90 | 90 | 90 | 4835.5 (6) | 100 (2) |
|  |  |  | 19.5969 (22) | 19.5240 (22) | 12.9603 (14) | 90 | 90 | 90 | 4958.7 (10) | 298 |
| Me, Ph, CH$_2$ | rctt | 3p-xylene - P-1 | 13.0968 (12) | 14.7232 (13) | 18.1206 (16) | 78.969 (1) | 77.827 (1) | 77.702 (1) | 3297.74 | 100 (2) |
|  |  | Sublimed/Empty - P2$_1$/c | 14.3913 (21) | 19.8671 (29) | 17.1496 (25) | 90 | 110.850 (2) | 90 | 4582.2 (12) | 100 (2) |
| Me, 4-MePh, CH$_2$ | rccc | Sublimed - P-1 | 15.5154 (11) | 17.7460 (13) | 20.4372 (15) | 109.577 (1) | 100.463 (1) | 94.401 (1) | 5155.85 | 100 (2) |
| Me, 4-MePh, CH$_2$ | rccc | Sublimed - Tetragonal (Unit Cell) | 22.34 | 22.34 | 41.93 | 90 | 90 | 90 | 20925 | 100 (2) |
| Me, 4-MePh, CH$_2$ | rctt |  |  |  |  |  |  |  |  |  |

TABLE 2-continued

Cavitand Composition Data

| Cavitand (R, R¹, Y) | Stereo isomer | New Complexes | a (Å) | b (Å) | c (Å) | α (°) | β (°) | γ (°) | V (Å³) | T (K) |
|---|---|---|---|---|---|---|---|---|---|---|
| NO₂, H, CH₂ | rccc | 2NO₂CH₃ - P2₁/c | 12.2944 (23) | 11.8264 (22) | 24.6129 (46) | 90 | 103.841 (2) | 90 | 3474.77 | 100 (2) |
| Br, Me, CH₂ | rccc | 2CCl₄ - Pnma | 23.4262 (48) | 14.1072 (29) | 13.1381 (27) | 90 | 90 | 90 | 4341.85 | 100 (2) |
| | | 2EtOAc - P2₁/n | 12.3385 (15) | 15.4284 (19) | 22.0928 (27) | 90 | 90.773 (2) | 90 | 4205.28 | 100 (2) |
| | | p-xylene - P2₁/n | 9.7358 (3) | 21.2018 (7) | 19.3794 (7) | 90 | 95.906 (2) | 90 | 3978.99 | 100 (2) |
| | | Sublimed/Empty - C2/m | 19.0053 (81) | 20.5047 (89) | 9.4568 (59) | 90 | 115.363 (3) | 90 | 3330 (3) | 100 (2) |
| H, H, SiMe₂ | rccc | 0.97CH₃Br - P2₁/m | 10.7771 (3) | 23.2733 (8) | 15.3035 (5) | 90 | 90.404 (2) | 90 | 3838.3 (2) | 100 (2) |
| | | 0.91CH₃Cl - P2₁/m | 10.8232 (11) | 23.1753 (24) | 15.2837 (16) | 90 | 90.427 (2) | 90 | 3833.5 (7) | 100 (2) |
| | | MeCN - P2₁/n | 15.6147 (18) | 11.2042 (13) | 22.6801 (27) | 90 | 107.620 (1) | 90 | 3781.7 (8) | 100 (2) |
| | | 0.19CH₃F - P2₁/n | 15.3018 (13) | 11.1458 (9) | 22.6486 (19) | 90 | 107.110 (1) | 90 | 3691.8 (5) | 100 (2) |
| | | 0.94CH₃I - P2₁/m | 10.7251 (14) | 23.3754 (31) | 15.3431 (20) | 90 | 90.370 (2) | 90 | 3846.5 (9) | 100 (2) |
| | | 0.03DME•0.10(H₂O) - P2₁/n | 15.2936 (12) | 11.1450 (9) | 22.6250 (17) | 90 | 107.052 (1) | 90 | 3686.84 | 100 (2) |
| | | NO₂CH₃ - P2₁/m | 10.8730 (8) | 23.1887 (17) | 15.2072 (11) | 90 | 90.395 (1) | 90 | 3834.11 | 100 (2) |
| | | 0.24(CH₃CCH) - P2₁/n | 15.4271 (16) | 11.1810 (11) | 22.7033 (23) | 90 | 107.510 (1) | 90 | 3734.6 (7) | 100 (2) |
| | | Empty - P2₁/n | 15.2400 (19) | 11.1290 (14) | 22.6153 (28) | 90 | 107.000 (2) | 90 | 3668.1 (8) | 100 (2) |
| | | Sublimed/x(H₂O) - P2₁/n | 15.2737 (24) | 11.1575 (18) | 22.6217 (36) | 90 | 107.084 (2) | 90 | 3685 (1) | 100 (2) |
| H, Me, SiMe₂ | rccc | 3(CH₃COCH₃)•x(H₂O) - P-1 | 11.1287 (3) | 15.3438 (4) | 17.0364 (5) | 108.583 (1) | 106.323 (1) | 90.359 (1) | 2631.54 | 100 (2) |
| | | 2(C₆H₆)•x(H₂O) - P2₁/n | 11.1753 (7) | 23.0596 (15) | 19.6234 (12) | 90 | 95.737 (1) | 90 | 5031.58 | 100 (2) |
| | | CH₃I•x(H₂O) [CH₃I outside] - P2₁/n | 11.2542 (6) | 16.5477 (9) | 24.1753 (13) | 90 | 93.015 (1) | 90 | 4495.96 | 100 (2) |
| | | 0.82(CH₃Cl)•CHCl₃ - P2₁/m | 10.1381 (11) | 20.1495 (21) | 11.2593 (12) | 90 | 91.773 (1) | 90 | 2298.92 | 100 (2) |
| | | CH₃F•CHCl₃—P2₁/m | 10.0930 (17) | 20.2481 (34) | 11.1542 (19) | 90 | 91.313 (2) | 90 | 2278.92 | 100 (2) |
| | | 0.20(DME)•CHCl₃ - P2₁/m | 10.0507 (15) | 20.2763 (30) | 11.1636 (16) | 90 | 91.495 (2) | 90 | 2274.27 | 100 (2) |
| | | CH₃CCH•CHCl₃ - P2₁/m | 10.2254 (29) | 20.1340 (57) | 11.2366 (32) | 90 | 92.390 (4) | 90 | 2311.36 | 100 (2) |
| | | mesitylene•x(H₂O) - P2₁/c | 10.9613 (9) | 19.3023 (16) | 24.1861 (21) | 90 | 103.097 (1) | 90 | 4984.14 | 100 (2) |
| | | 0.93(CH₃Cl)•0.5 (C₁₀H₁₄) - P2₁/n | 9.2535 (9) | 11.4711 (11) | 24.1032 (23) | 76.462 (1) | 86.097 (1) | 68.991 (1) | 2321.71 | 100 (2) |
| | | 0.17(CH₃F) - P2₁/n | 12.5117 (9) | 21.4532 (15) | 16.3933 (11) | 90 | 105.677 (1) | 90 | 4236.5 (5) | 100 (2) |
| | | 0.22(DME)•C₁₀H₁₄ - P2₁/m | 11.2823 (23) | 18.3561 (37) | 12.4616 (25) | 90 | 90.656 (3) | 90 | 2580.62 | 100 (2) |
| | | CH₃CCH•C₁₀H₁₄ - P2₁/m | 11.2920 (7) | 18.2727 (11) | 12.5036 (7) | 90 | 90.430 (1) | 90 | 2579.86 | 100 (2) |
| | | Sublimed, x(H₂O) - P2₁/n | 12.4947 (8) | 21.4728 (14) | 16.3608 (11) | 90 | 105.536 (1) | 90 | 4229.16 | 100 (2) |
| | | 0.5(toluene)•x(H₂O) - Cmc2₁ | 20.8478 (65) | 9.3670 (29) | 45.1885 (14) | 90 | 90 | 90 | 8824.47 | 100 (2) |
| H, i-Bu, SiMe2 | rccc | Empty - C2/c | 23.8783 (24) | 8.3377 (9) | 42.1053 (43) | 90 | 100.631 (1) | 90 | 8238.9 (15) | 100 (2) |
| Me, H, SiMe₂ | rccc | | 23.9160 (31) | 8.4243 (11) | 42.4217 (55) | 90 | 100.521 (2) | 90 | 8403.2 (19) | 296 (2) |
| | | CH₃I -C2/c | 23.7418 (15) | 8.3761 (5) | 42.6673 (28) | 90 | 99.403 (1) | 90 | 8371.0 (9) | 100 (2) |
| | | CH₃Br - C2/c | 23.7815 (29) | 8.3577 (10) | 42.3173 (52) | 90 | 98.998 (2) | 90 | 8307.4 (17) | 100 (2) |
| | | CH₃Cl - C2/c | 23.8190 (24) | 8.3375 (9) | 42.2158 (43) | 90 | 99.032 (1) | 90 | 8279.7 (15) | 100 (2) |
| | | 0.80(CH₃F) - C2/c | 23.8281 (25) | 8.3065 (9) | 42.1464 (44) | 90 | 99.653 (1) | 90 | 8223.8 (15) | 100 (2) |
| | | EtCl - C2/c | 23.5981 (20) | 8.4762 (7) | 42.8436 (35) | 90 | 99.750 (1) | 90 | 8445.9 (12) | 100 (2) |
| | | 0.74(BrCH₂Cl) - C2/c | 23.7650 (20) | 8.4219 (7) | 42.7905 (36) | 90 | 101.108 (1) | 90 | 8403.9 (12) | 100 (2) |

TABLE 2-continued

Cavitand Composition Data

| Cavitand (R, R¹, Y) | Stereo isomer | New Complexes | a (Å) | b (Å) | c (Å) | α (°) | β (°) | γ (°) | V (Å³) | T (K) |
|---|---|---|---|---|---|---|---|---|---|---|
| | | 0.85($CH_2Cl_2$) - C2/c | 23.8439 (22) | 8.3749 (8) | 42.7877 (39) | 90 | 101.337 (1) | 90 | 8377.6 (13) | 100 (2) |
| | | 0.82(DME) - C2/c | 23.8115 (22) | 8.3707 (8) | 42.6458 (40) | 90 | 100.829 (1) | 90 | 8348.7 (14) | 100 (2) |
| | | 0.83($CH_3SH$) - C2/c | 23.8489 (14) | 8.3186 (5) | 42.2892 (26) | 90 | 99.377 (1) | 90 | 8277.6 (9) | 100 (2) |
| | | 0.06($I_2$) - C2/c | 23.8600 (12) | 8.3389 (4) | 42.1352 (22) | 90 | 100.525 (1) | 90 | 8242.4 (7) | 100 (2) |
| | | 0.72($C_2H_6$) - C2/c | 23.7918 (15) | 8.3456 (5) | 42.2677 (26) | 90 | 99.785 (1) | 90 | 8270.5 (10) | 100 (2) |
| | | 0.77(Xe) - C2/c | 23.7847 (20) | 8.3252 (7) | 42.2368 (35) | 90 | 99.359 (1) | 90 | 8252.1 (12) | 100 (2) |
| | | 0.41($C_2H_4$) - C2/c | 23.8487 (12) | 8.3237 (4) | 42.0407 (21) | 90 | 99.880 (1) | 90 | 8226.6 (7) | 100 (2) |
| | | 0.54(Kr) - C2/c | 23.8156 (27) | 8.3314 (10) | 42.0998 (48) | 90 | 99.948 (1) | 90 | 8227.7 (17) | 100 (2) |
| | | 0.29(Ar) - C2/c | 23.8429 (12) | 8.3337 (4) | 42.0738 (22) | 90 | 100.309 (1) | 90 | 8225.1 (7) | 100 (2) |
| | | 0.46($CO_2$) - C2/c | 23.9014 (24) | 8.3164 (8) | 41.9864 (43) | 90 | 100.205 (1) | 90 | 8213.8 (14) | 100 (2) |
| | | 0.26($CH_4$) - C2/c | 23.934 (13) | 8.3621 (45) | 42.157 (23) | 90 | 100.501 (6) | 90 | 8296 (8) | 100 (2) |
| | | MeCN - C2/c | 23.8211 (29) | 8.3280 (12) | 42.0611 (62) | 90 | 98.894 (2) | 90 | 8244 (2) | 100 (2) |
| | | $NO_2CH_3$ - C2/c | 23.9220 (31) | 8.2830 (11) | 42.4669 (54) | 90 | 100.387 (1) | 90 | 8276.7 (19) | 100 (2) |
| | | 0.67(MeOH) - C2/c | 23.9064 (22) | 8.3015 (8) | 42.1497 (39) | 90 | 100.301 (1) | 90 | 8230.2 (13) | 100 (2) |
| | | 0.13(EtOH) - C2/c | 23.8670 (26) | 8.3297 (9) | 42.1428 (46) | 90 | 100.399 (2) | 90 | 8240.6 (16) | 100 (2) |
| | | empty - P-1 | 11.8168 (8) | 12.4352 (8) | 28.3927 (18) | 96.443 (1) | 90.292 (1) | 91.446 (1) | 4144.3 (5) | 100 (2) |
| | | $2CHCl_3 \cdot CH_3CCH$ - $P2_1/n$ | 11.6044 (23) | 18.0529 (35) | 24.1294 (47) | 90 | 98.247 (2) | 90 | 5002.67 | 100 (2) |
| Me, Me, $SiMe_2$ | rccc | Sublimed/Empty - P2/n | 22.7948 (24) | 9.2086 (10) | 43.2150 (45) | 90 | 100.508 (2) | 90 | 8919.05 | 100 (2) |
| Me, Et, $SiMe_2$ | rccc | $x(H_2O)$ - $P2_1/n$ | 14.3462 (22) | 17.7706 (27) | 19.8442 (30) | 90 | 101.492 (2) | 90 | 4957.7 (13) | 100 (2) |
| H, Me, $SiEt_2$ | rccc | EtOAc•$x(H_2O)$ - P-1 | 11.3409 (14) | 13.7853 (17) | 18.6917 (24) | 80.679 (2) | 81.906 (2) | 67.770 (2) | 2659.17 | 100 (2) |
| Me, H, $SiEt_2$ | | | | | | | | | | |
| Me, Me, $SiEt_2$ | rccc | $BrCH_2Cl \cdot x(H_2O)$ - P-1 | 11.9231 (15) | 12.5610 (16) | 18.6982 (23) | 109.099 (2) | 97.895 (2) | 94.984 (2) | 2595.00 | 100 (2) |
| H, H, Si (i-Pr)$_2$ | rccc | | | | | | | | | |
| H, Me, Si (i-Pr)$_2$ | rccc | | | | | | | | | |
| Me, H, Si (i-Pr)$_2$ | rccc | Sublimed/Empty - I4 | 16.5767 (15) | 16.5767 (15) | 9.9147 (9) | 90 | 90 | 90 | 2724.4 (4) | 100 (2) |
| Me, Me, Si (i-Pr)$_2$ | rccc | | | | | | | | | |

EXAMPLES

General Methods

All solvents were used as received from Fisher (Pittsburg, Pa.). Reagents were obtained from Acros (Pittsburgh, Pa.) or Aldrich (Milwaukee, Wis.) and were used without further purification. Chromatography was carried out on silica gel (32-64 μm) from Silicycle Chemical Division.

Thermogravimetric Analysis and TGA-MS

Thermogravimetric analyses (TGA) were performed with a TA Instruments Q5000IR TGA. Unless otherwise indicated, samples were placed in platinum pans and heated at a rate of 5° C./min under a constant flow of dry helium (10 mL/min.).

$^1$H Nuclear Magnetic Resonance ($^1$H NMR)

For the characterization of the compounds, $^1$H (400 MHz) and $^{13}$C (100 MHz) NMR spectra were carried out on a Varian 400-MR spectrometer at 9.4 T. MestReNova version 5.2.5-4119 software was used for data analysis. Deuterated solvents were used as received from Cambridge Isotope Laboratories, Inc. Unless otherwise noted, these spectra were obtained at room temperature and chemical shifts given are based upon on the residual solvent peaks. Splitting patterns are labeled as singlet (s), doublet (d), triplet (t) and broad (br.). Encapsulated species are indicated by preceding an @ symbol.

Data Collection and Structure Determination

Single crystal X-ray diffraction data were collected at 100(2) K (or room temperature, as indicated) on a Siemens SMART three-circle X-ray diffractometer equipped with an APEX II CCD detector (Bruker-AXS) and an Oxford Cryosystems 700 Cryostream, using Mo Kα radiation (0.71073 Å). The crystal structures were solved by direct methods using SHELXS, and all structural refinements were conducted using SHELXL-97-2 (G. M. Sheldrick, *Acta Cryst.* 2008, A64, 112-122). All non-hydrogen atoms were modeled with anisotropic displacement parameters. All hydrogen atoms were placed in calculated positions and were refined using a riding model with coordinates and isotropic displacement parameters being dependent upon the atom to which they are attached. The program X-Seed (Barbour, L. *Supramol. Chem.* 2001, 1, 189. http://x-seed.net) was used as a graphical interface for the SHELX software suite and for the generation of figures.

Cavity Volumes

Cavity volumes are usually extracted from atomic coordinate data by computationally probing the cavity with a sphere of a defined probe radius. The volume of space that can be encompassed by rolling the sphere around the interior of the cavity is summed over all achievable positions of the sphere. The atomic coordinates maybe provided by computational or experimental data. For structure of formula (Ia), crystal structure data were used with normalized C—H bond lengths of 1.08 Å. Cavity volumes were calculated using the X-seed interface (Barbour, L. *Supramol. Chem.* 2001, 1, 189. http://x-seed.net) to MSRoll (Connolly, M. L. J. *Mol. Graph.* 1993, 11, 139.), employing the default van der Waals atomic radii and a 1.4 Å probe radius.

Example 1a

Synthesis of Empty Crystalline Cavitand Compositions of Formula (Ia)

The synthesis of a compound of formula (Ia) was originally performed by Cram by an the acid-catalyzed condensation reaction between acetaldehyde and resorcinol is high yielding (Tunstad, L. M.; Tucker, J. A.; Dalcanale, E.; Weiser, J.; Bryant, J. A.; Sherman, J. C.; Helgeson, R. C.; Knobler, C. B.; Cram, D. J. *J. Org. Chem.* 1989, 54, 1305).

An alternate synthetic pathway in analogy to that used by Sherman et al. for intramolecular ring closing among all hydroxy functionalities provides better yields after all necessary purification steps (Naumann, C.; Roman, E.; Peinador, C.; Ren, T.; Patrick, B. O.; Kaifer, A. E.; Sherman, J. C. *Chem. Eur. J.* 2001, 7, 1637).

After workup and subsequent purification of the cavitand of formula (Ia), the colorless solid was sublimed at high temperature and low pressure to give single crystals of empty cavitand which were analyzed by single crystal x-ray diffraction (SCXRD) at 100 and 298 K. Further analysis of this guest-free form using the MSRoll subroutine (Connolly, M. L. J. *Mol. Graph.* 1993, 11, 139) in XSEED (Barbour, L. J. *J. Supramol. Chem.* 2001, 1, 181) showed a cavity volume of approximately 61 Å$^3$ using a 1.4 Å probe radius and normalizing all C—H bonds to 1.08 Å (FIG. 1).

Example 1b

X-Ray Analysis of Empty Cavitand Compositions of Formula (Ia)

The crystallographic parameters of a guest-free form of crystalline formula (Ia) are in congruence with the $CH_2Cl_2$@formula (Ia) solvate that was isolated and studied by Cram by SCXRD (FIG. 1) (the "@" symbol denotes that the cavitand encapsulates the guest) (Tunstad, L. M.; Tucker, J. A.; Dalcanale, E.; Weiser, J.; Bryant, J. A.; Sherman, J. C.; Helgeson, R. C.; Knobler, C. B.; Cram, D. J. *J. Org. Chem.* 1989, 54, 130).

Powder x-ray diffraction analysis (PXRD) may also be used to analyze bulk samples of empty cavitand crystals and cavitand crystals, where the cavitand is complexed with a solvent guest. Differences in the composition may be observed by changes in shift and intensity of PXRD peaks. This observation prompted further exploration of cavitand complexation with much more volatile gas species.

For cavitand compositions of formula (Ia), powder x-ray diffraction analysis (PXRD) of the bulk samples of empty [a(simulated), b(experimental)] and the dichloromethane (DCM) complex [d(simulated), e(experimental)] (FIG. 2) do, however, show a few differences: 1) the intensities of (11-2) and (11-3) are much larger for the DCM clathrate as opposed to empty due to the presence of chlorine atoms in the sample, 2) a shift in the (200) peak to larger 2θ since the b axis is expanded to accommodate the large guest. This observation prompted further exploration of cavitand complexation with much more volatile gas species.

By utilizing a number of different guests, it is possible to probe a cavities' ability to expand itself for guest accommodation, determine how it behaves electronically upon complexation (dipolar interactions) as well as understand the stability these complexes may have over time at ambient conditions and under elevated temperatures. Crystallographic data for compositions of formula (Ia) are shown in table 3, below.

TABLE 3

Crystallographic Data for x(Guest)@formula (Ia).

| Crystal Parameters | formula (Ia) | formula (Ia) | $CH_2Cl_2$@formula (Ia) | $BrCH_2Cl$@formula (Ia) | $CH_2Br_2$@formula (Ia) |
|---|---|---|---|---|---|
| Chemical formula | $C_{36}H_{32}O_8$ | $C_{36}H_{32}O_8$ | $C_{37}H_{34}O_8Cl_2$ | $C_{37}H_{34}O_8BrCl$ | $C_{37}H_{34}O_8Br_2$ |
| Formula weight, g/mol | 592.62 | 592.62 | 677.58 | 722.03 | 766.48 |
| Growth solvent | None | None | $CH_2Cl_2$ | $BrCH_2Cl$ | $CH_2Br_2$ |
| Crystal system | Monoclinic | Monoclinic | Monoclinic | Orthorhombic | Orthorhombic |
| Space group | C2/c | C2/c | C2/c | Pbcm | Pbcm |
| Z | 8 | 8 | 8 | 4 | 4 |
| a, Å | 20.0002 (13) | 20.0491 (13) | 19.7686 (29) | 10.8698 (9) | 10.8853 (17) |
| b, Å | 7.9569 (5) | 8.0236 (5) | 8.1693 (12) | 15.2836 (13) | 15.4820 (24) |
| c, Å | 38.3855 (28) | 38.5515 (28) | 38.9892 (56) | 19.0701 (16) | 19.0058 (30) |
| α, deg | 90 | 90 | 90 | 90 | 90 |
| β, deg | 103.469 (1) | 103.281 (1) | 101.402 (2) | 90 | 90 |
| γ, deg | 90 | 90 | 90 | 90 | 90 |
| V, Å$^3$ | 5940.6 (7) | 6035.8 (7) | 6172.3 (16) | 3168.5 (5) | 50 |
| $\rho_{calc}$, g/cm$^3$ | 1.33 | 1.30 | 1.46 | 1.51 | 1.59 |

TABLE 3-continued

Crystallographic Data for x(Guest)@formula (Ia).

| Crystal Parameters | formula (Ia) | formula (Ia) | $CH_2Cl_2$@formula (Ia) | $BrCH_2Cl$@formula (Ia) | $CH_2Br_2$@formula (Ia) |
|---|---|---|---|---|---|
| crystal dimensions, mm | 0.38 × 0.26 × 0.16 | 0.38 × 0.26 × 0.16 | 0.45 × 0.28 × 0.28 | 0.64 × 0.42 × 0.35 | 1.30 × 0.92 × 0.44 |
| T, K | 100(2) | 298 (2) | 100 (2) | 100 (2) | 100 (2) |
| 2Θ max for refinement, deg | 56.0 | 54.3 | 50.0 | 50.0 | 50.0 |
| total reflections | 25444 | 25370 | 18834 | 22258 | 21936 |
| independent reflections | 7093 | 6672 | 5439 | 2885 | 2909 |
| no. of observed data | 5407 | 4163 | 4036 | 2535 | 2128 |
| no. of parameters | 392 | 401 | 428 | 228 | 228 |
| μ, mm$^{-1}$ | 0.093 | 0.092 | 0.267 | 1.437 | 2.586 |
| $R_{int}$ | 0.0362 | 0.0384 | 0.0504 | 0.025 | 0.0664 |
| $R_1(F)$, $wR_2(F^2)$, (I > 2σ(I)) | 0.0431, 0.1035 | 0.0453, 0.1034 | 0.0608, 0.1481 | 0.0404, 0.1311 | 0.0429, 0.1153 |
| Goodness-of-fit on $F^2$ | 1.058 | 0.997 | 1.054 | 1.219 | 1.069 |

Example 1c

Thermogravimetric Analysis of Empty Cavitand Compositions of Formula (Ia)

The presence or absence of a guest molecule complexed within a crystalline cavitand composition of the invention can also be determined by thermogravimetric analysis (TGA). TGA provides a tool to analyze the thermodynamics of guest loss upon heating of a composition up to the sublimation temperature of the cavitand composition.

In some instances, since the kinetics of guest loss are quite broad, an accurate onset temperature cannot be ascertained; however the maximum rate of guest loss may be measured ($T_{max}$) and used as a quantitative measure of guest confinement.

Figure 3:
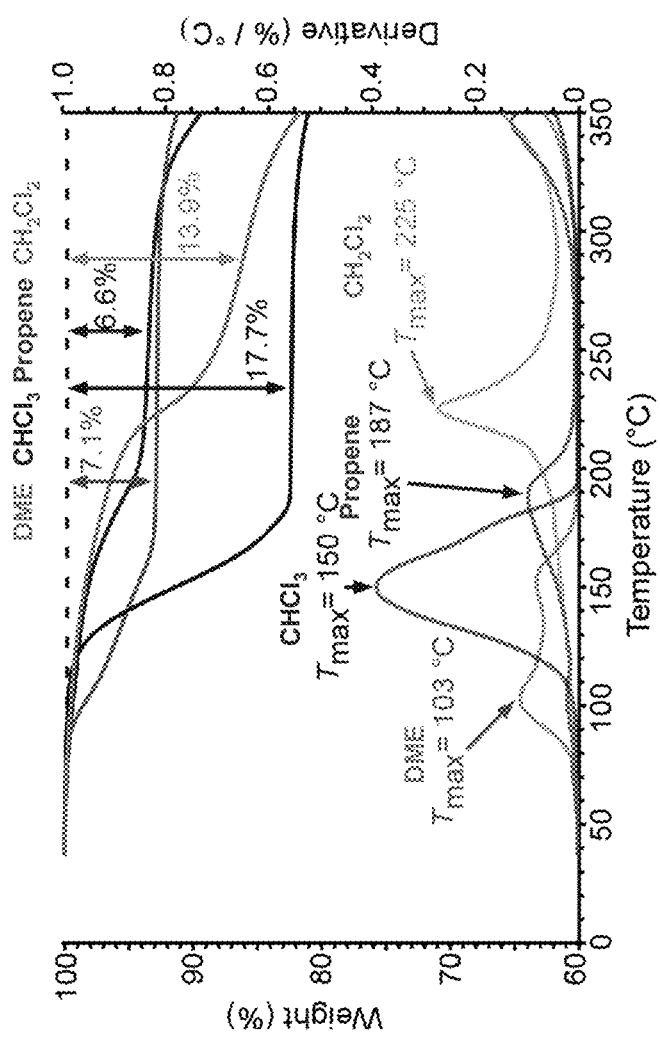
FIG. 3: Thermogravimetric analysis of various x(guest)@formula (Ia) inclusion compounds with corresponding % weight loss and $T_{max}$ values.
Figure 4A:
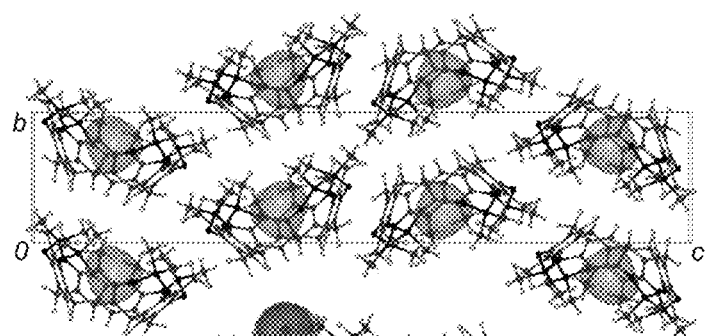
FIGS. 4a-d: Isostructural crystal packing of a) empty formula (Ib), illustrating the unoccupied 28 Å$^3$ ultramicrocavities, b) 0.85$CH_2Cl_2$@formula (Ib), and c) the partial hydrate $xH_2O$@formula (Ib) (x<0.4), as seen for one layer of molecules packed in the be plane. d) Spacefill model of the empty and $CH_2Cl_2$-occupied formula (Ib) cavitands as viewed from the top of the bowls. Cavity volumes in a) and b) are depicted (1.4 Å probe) and guests are shown as spacefill models.
Figure 4B:
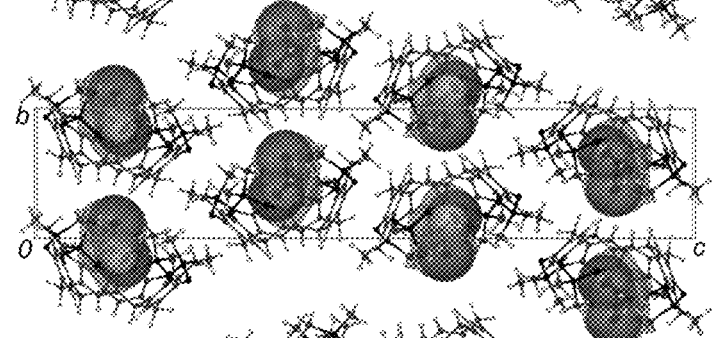
Figure 4C:
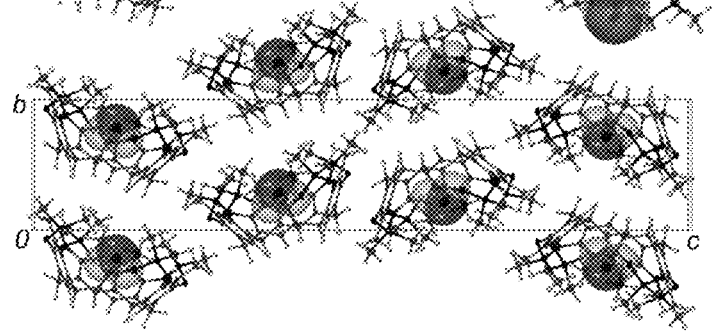
Figure 4D:
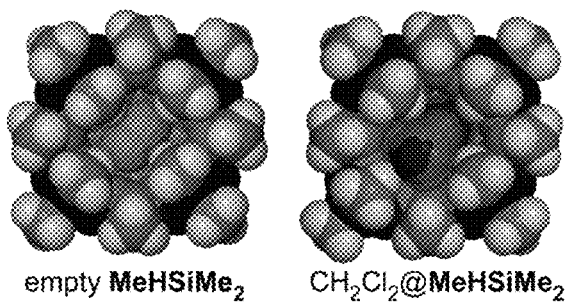

A composition of formula (Ia) in the form of a dichloromethane solvate was isolated after reaction purification and studied by thermogravimetric analysis (TGA), and then compared with other guest molecule complexes, such as propene, dimethyl ether, and trichloromethane (FIG. 3). The TGA values of several other guest molecules are also summarized in Table 4, below.

For example, when a cavitand of formula (Ia) was complexed with the solvent $CH_2Cl_2$ as the guest molecule, approximately one equivalent of $CH_2Cl_2$ was lost ($T_{max}$=225° C.), an event that also coincided with sublimation of empty cavitand. Due to the large $T_{max}$ of guest loss for this complex, the empty cavitand of formula (Ia) could not be generated after heating the sample at 220° C. for 3 days as the $^1$H NMR still showed residual signals for the solvent.

Figure 2:
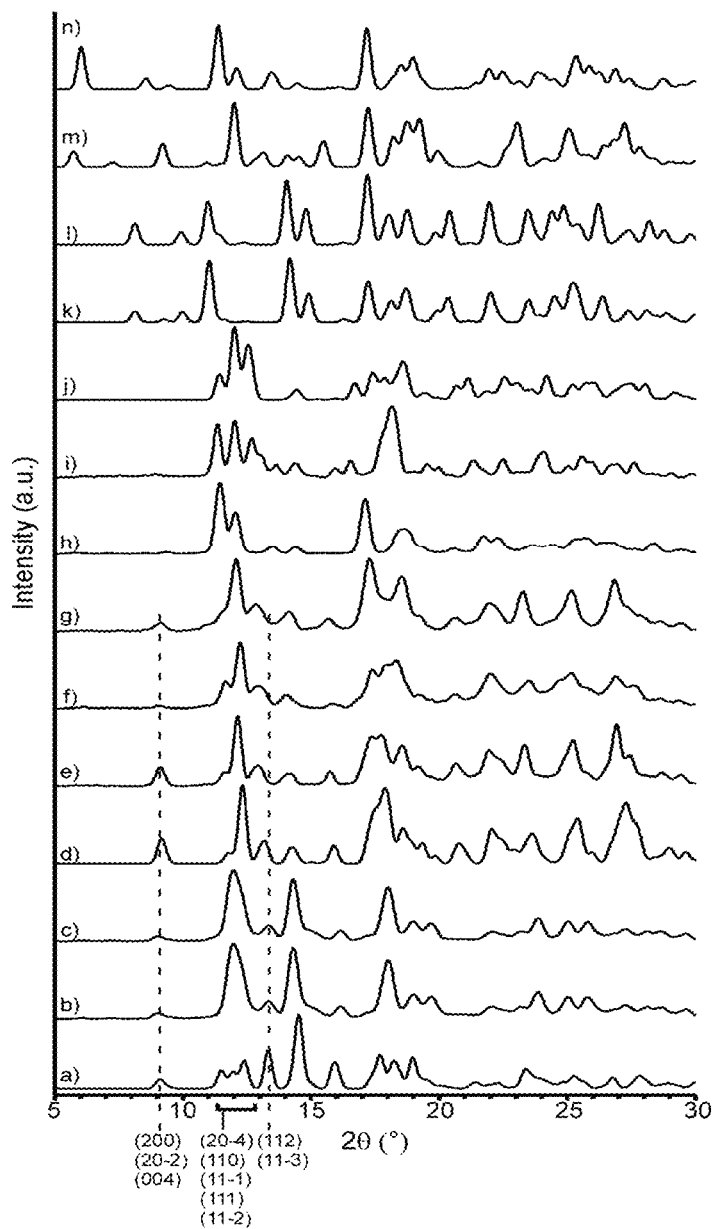
FIG. 2: Powder X-ray Diffraction (PXRD) patterns of a) empty formula (Ia)—simulated (298 K), b) empty formula (Ia) (298 K), c) formula (Ia) from propane experiment (298 K) d) $CH_2Cl_2$@formula (Ia) (298 K), e) $CH_2Cl_2$@formula (Ia)—simulated (100 K), f) $CH_3Cl$@formula (Ia) (298 K), g) EtCl@formula (Ia) (298 K), h) $x(CH_3OCH_3)$@formula (Ia) (298 K), i) $CH_3CHCH_2$@formula (Ia) (298 K), j) $NO_2CH_3$@formula (Ia)—simulated (100 K), k) $BrCH_2Cl$@formula (Ia)—simulated (100 K), l) $CH_2Br_2$@formula (Ia)—simulated (100 K), m) $(CH_2Cl)_2$@formula (Ia)—simulated (100 K), n) $CHCl_3$@formula (Ia)—simulated (100 K).

To circumvent this shortcoming, a batch of $CHCl_3$@formula (Ia) crystals were grown (by slow evaporation of a chloroform solution of formula (Ia)) and placed in the oven at 150° C. for 1 day to give the empty cavitand, as confirmed by $^1$H NMR and powder x-ray diffraction (PXRD) (FIG. 2). The greater ease of guest loss in this case is due to a less tightly packed phase of formula (Ia), an observation caused by the larger van der Waals volume of chloroform over dichloromethane (74 vs. 59 Å$^3$).

Example 1d

Encapsulation Studies of Empty Cavitand Compositions of Formula (Ia)

In order to study the selectivity of formula (Ia) for more volatile guests, a variety of gases were used that possess variable polarities and sizes (Table 4). Pure, empty formula (Ia) (25 mg) was placed in a sealed borosilicate glass vial (when $P_{vapor}$<5 atm) or a Teflon bomb (when $P_{vapor}$>5 atm) along with enough liquefied gas to ensure an equilibrium between liquid and gas phases.

These mixtures were stirred for 1-2 days to ensure that all the empty material dissolved in the liquefied gas before precipitating as the inclusion compound. The vessels were then opened and the remaining liquid was allowed to evaporate and a nitrogen stream was passed over the solid for 20 minutes to remove residual gas. The solids were then analyzed by $^1$H NMR, TGA and PXRD (FIG. 2) and the results summarized in Table 4.

TABLE 4

Complexes of formula (Ib) with various guests (bp, vdW volumes) and respective fractional occupancies as determined by $^1$H NMR and TGA. Guest occupancies of gaseous species were also determined after $^a$8 days and $^b$5 days by $^1$H NMR.

| Guest | bp (° C.) | Vol. (Å$^3$) | $^1$H NMR | TGA wt %/eq. | $T_{max}$ (° C.) | $T_{max} - T_{bp}$ (° C.) |
|---|---|---|---|---|---|---|
| Propene | −48 | 57 | 0.76(0.6)$^a$ | 6.6/0.99 | 187 | 235 |
| Propane | −42 | 62 | 0.03(0.03)$^a$ | 1.5/0.20 | 75 | 117 |
| $CH_3Cl$ | −24 | 44 | 1.00(0.80)$^a$ | 8.0/1.02 | 225 | 249 |
| $CH_3OCH_3$ | −24 | 53 | 1.00(0.86)$^b$ | 7.1/0.98 | 103 | 127 |
| EtCl | 12 | 61 | 1.00(1.00)$^a$ | 9.7/0.99 | 289 | 277 |
| $CH_2Cl_2$ | 40 | 59 | 1 | 13.9/1.13 | 225 | 185 |
| $BrCH_2Cl$ | 68 | 64 | 1 | 18.7/1.05 | 106 | 38 |
| $CHCl_3$ | 61 | 74 | 1 | 17.7/1.07 | 150 | 89 |
| $NO_2CH_3$ | 101 | 51 | 1 | 8.8/0.94 | 190 | 89 |

For example, chloromethane and chloroethane both have dipole moments, but different molecular geometries, yet both completely occupy the cavity of a compound of formula (Ib) as seen by $^1$H NMR and TGA. As seen from the respective PXRD patterns, the (112) and (11-3) peaks are shifted towards lower 2θ values (FIG. 2).

This observation is even more pronounced in the case of chloroethane (Vol.=61 Å$^3$); the empty crystalline cavitand complex of formula (Ia) has a void space of 61 Å$^3$, so the cell axes must swell in order to complex the guest and still maintain the same packing motif as the empty cell. Also, since chloroethane fills virtually all the void space of the cavitand, it is more thermodynamically stabilized by van der Waals interactions, in addition to a quadrupole-dipole interaction among the phenyl rings. This increase in stability is seen in the higher $T_{max}$ and $T_{max}-T_{bp}$ value versus that of chloromethane [$T_{max}$-MeCl (255° C.) vs. EtCl (289° C.)/$T_{max}-T_{bp}$-MeCl (249° C.) vs. EtCl (277° C.)].

Analysis of $CH_3OCH_3$ complexes with a cavitand of formula (Ia) shows that the gas is fully occupied in the cavitand, however it is not 100% retained after 5 days. The $T_{max}-T_{bp}$ value for this inclusion complex is also drastically diminished when compared to a guest of similar van der Waals volume (EtCl). The reason for this is two-fold: 1) dimethyl ether does not possess a dipole, so the cavitand has less of an affinity for the guest, and 2) the PXRD pattern of $CH_3OCH_3$ is not identical to that of the empty cavitand of formula (Ia) and the EtCl complex, suggesting that less efficient packing is responsible for the lack of gas confinement in the solid state.

Perhaps what is most intriguing is the selectivity that cavitand of formula (Ia) exhibits between propane and propylene. Propylene is produced almost entirely as a byproduct of ethylene production by cracking and refinery processes (Propene. *Ullmann's Encyclopedia of Industrial Chemistry*, 7$^{th}$ ed; VCH: Weinheim, Germany, 2005) and its separation from propane represents one of the most important operations in the petrochemical industry. (Järvelin H.; Fair, J. R. *Ind. Eng. Chem. Res.* 1993, 32, 2201.)

Current methods for the separation of propane/propylene involve highly complex separation units and energy intensive processes due to their similar properties and boiling points. Materials that have been shown to separate such gases on a small scale include SBA-15 (Basaldella, E. I.; Tara, J. C.; Armenta, G. A.; Patiño-Iglesias, M. E.; Castellón, E. R. *J. Sol.-Gel. Sci. Techn.* 2006, 37, 141.) and AgNO$_3$/SiO$_2$ sorbents (Rege, S. U.; Yang, R. T. *Chem. Eng. Sci.* 2002, 57, 1139).

Though the cavitand displays very low solubility in both liquefied gases, the affinity that composition of formula (Ia) has for propylene is unquestionable. The equivalents of propane that are bound are variable since the $^1$H NMR and TGA give distinctly different numbers (0.03 vs. 0.20 eq.). This may be due to propane being lost upon dissolving the complex for NMR analysis. The low equivalents would also explain how the PXRD pattern for the bulk sample is identical to that of the empty cavitand. Nonetheless, despite how little propane is present in the cavity, it is held over a period of 8 days without any loss.

This behavior is the inverse to that of propylene. High equivalents of propylene found by $^1$H NMR and TGA (nearly full occupancy), however it only retains about 80% of the guest after 8 days. This observation is still remarkable yet. The volume of propylene is only 5 Å$^3$ less than that of propane, however is virtually fully occupied in the cavitand of formula (Ia). The lesser retention of propylene over time at ambient conditions is not surprising since it has a negligible dipole compared to that of EtCl, which is retained 100% over 8 days. This is further illustrated by the different packing mode of the propylene complex as seen by the PXRD pattern; therefore not identical to the empty/DCM pattern. This feature of formula (Ia) may prove to be fruitful in industrial applications towards the separation of propane and propylene.

Several single crystal structures of formula (Ia) in various solvents were also determined [$NO_2CH_3$, $CHCl_3$, $CH_2Br_2$, $BrCH_2Cl$, $(CH_2Cl)_2$]. In an effort to determine the phases of $CH_3CHCH_2$@formula (Ib) and $CH_3OCH_3$@formula (Ib), the simulated PXRD patterns of all single crystal solvates were superimposed (FIG. 2). Bromochloromethane (BCM) and dibromomethane (DBM) both crystallize in a primitive orthorhombic crystal setting and do not compare with the gas solvates mentioned. The dichloroethane and chloroform solvates of formula (Ia) crystallize in a primitive monoclinic crystal setting and contain low 2θ planes that are not congruent with the patterns of propylene and dimethyl ether bound complexes as well.

Example 2a

Empty Cavitand Compositions of Formula (Ib)

In another example, FIG. 4 shows the X-ray single crystal structure of freshly sublimed composition of formula (Ib) (100 K). The molecules pack in an as-close-as-possible packed arrangement of cavitand layers adopting the monoclinic C2/c space group (Z=8) with a unit cell volume that averages 8230(10) Å$^3$ at 100 K, as determined for several crystals.

Figure 5:
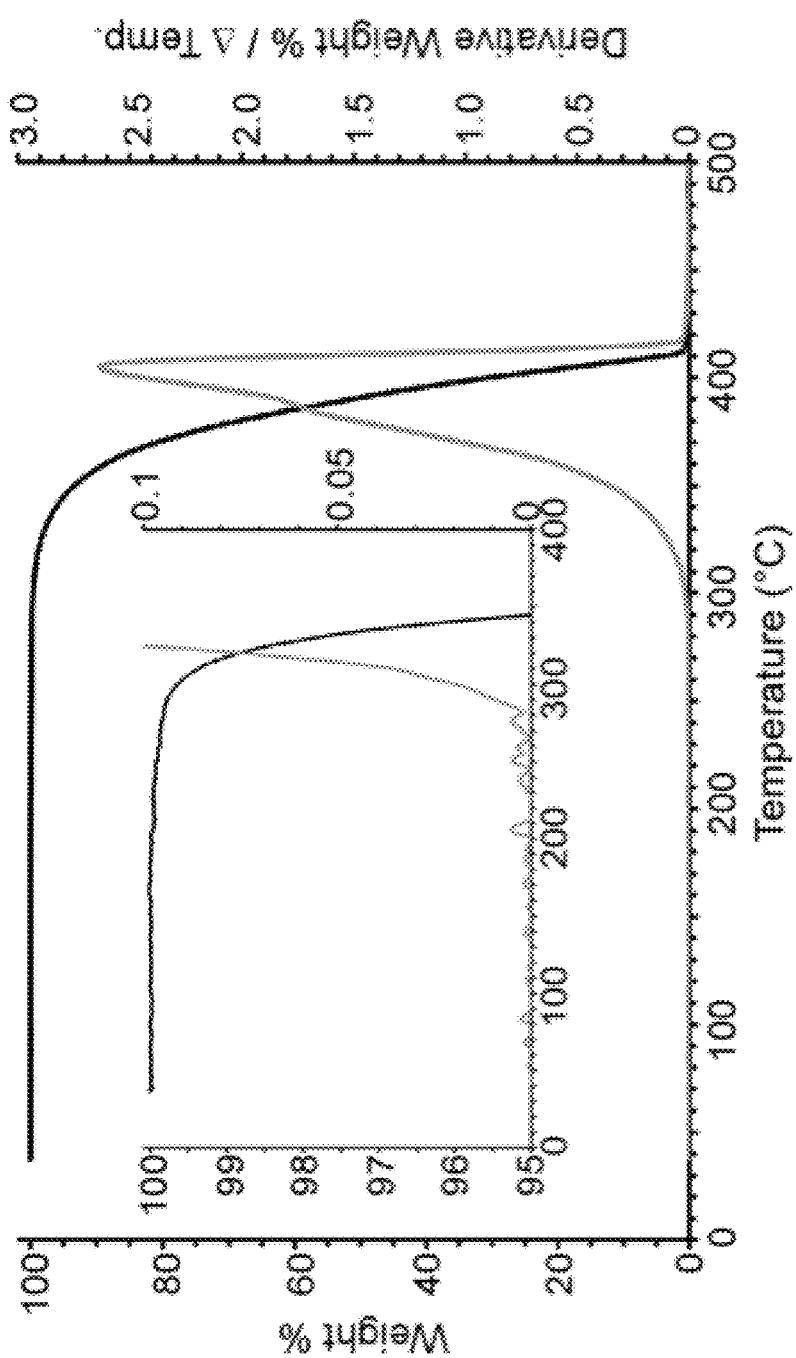
FIG. 5: TGA of empty formula (Ib) (black) and derivative weight curve. Inset: magnified view.

Though the molecules of formula (Ib) are close-packed, the bowl-shaped cavitands enforce discrete, empty cavities of approximately 28 Å$^3$, constituting 2.7% of the crystal volume. Electron density analysis reveals that freshly prepared crystals are truly empty. Moreover, thermogravimetric analysis (TGA) of empty formula (Ib) reveals no mass loss whatsoever up to the point of sublimation, which onsets at about 310° C. and reaches its maximum rate at 395(12)° C. (heating rate=5° C./min.) (FIG. 5).

Example 2b

Guest Complexed Cavitand Compositions of Formula (Ib)

In contrast, when formula (Ib) is crystallized from certain small molecule solvents, it forms simple 1:1 solvent@formula (Ib) clathrates (e.g. solvent=CH$_3$I, CH$_3$CN, NO$_2$CH$_3$, see Table 5) or partial solvates, as in xCH$_2$Cl$_2$@formula (Ib) (x≥0.85). Notably, the solvates adopt essentially the same crystal packing as the empty form, with the solvents simply occupying the otherwise empty cavitand cavities. For instance, the 100 K unit cell volume of CH$_3$CN@formula (Ib) ($V_{cell}$=8244(2) Å$^3$)—the clathrate of the smallest of these solvents—is nearly indistinguishable from empty formula (Ib), despite a doubling of the cavity volume ($V_{cav}$) from 28 Å$^3$ to 64 Å$^3$ (6.2% of the crystal) to accommodate the 44 Å$^3$ CH$_3$CN guest. The solvent is efficiently packed within the formula (Ib) cavity, occupying approximately 69% of the available volume.

Figure 10:
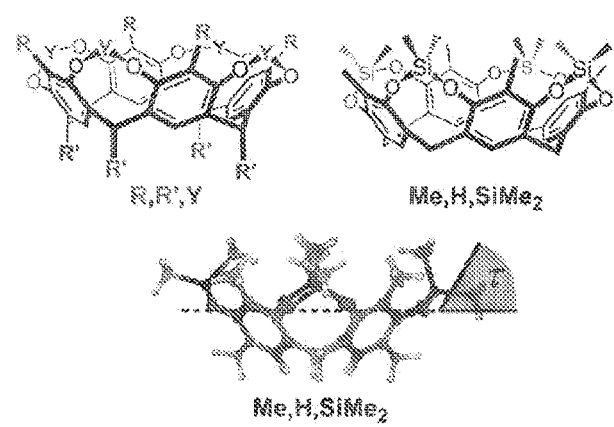
FIG. 10: Swelling of the formula (Ib) cavity largely entails an outward swinging of the O—Si—O linkages such that the angles between the planes defined by the O—Si—O linkages and the plane defined by the upper rim atoms of the pseudo 4-fold symmetric cavitand (angle τ) are all more acute.

Swelling of the formula (Ib) cavity largely entails an outward swinging of the O—Si—O linkages such that the angles between the planes defined by the O—Si—O linkages and the plane defined by the upper rim atoms of the pseudo 4-fold symmetric cavitand (angle τ) are all more acute (FIG. 10). For CH$_3$CN@formula (Ib), the average τ angle is 8.4° smaller (Δτ(avg.)) than for the empty phase, despite little overall change in the unit cell volume (Table 6).

For clathrates of the other solvents, however, the unit cells are slightly expanded as compared to the empty form.

The observed unit cell volumes, and conformational $\Delta\tau$ angles of the host are loosely correlated with the volume of the solvent: the cavitand shows a modest ability to expand its molecular cavity, from 28 Å$^3$ to an apparent maximum of about 80 Å$^3$, to accommodate guests. Moreover, the crystal packing of formula (Ib) shows some ability to accommodate modest protrusions of the guests from the upper rim of the cavity via slight alterations of the crystal packing and expansion of the unit cell, up to about 8440 Å$^3$ (measured at 100 K).

For example, the 100 K unit cell of a single crystal of 0.85CH$_2$Cl$_2$@formula (Ib) ($V_{cell}$=8378(1) Å$^3$)—formally, this crystal is a solid solution of empty and occupied cavitands—is larger by $\Delta V_{cell}$=148 Å$^3$ (1.8%) relative to empty formula (Ib). The degree of crystal expansion is minimal, however, considering that, on average per unit cell, 6.8 molecules of CH$_2$Cl$_2$ (6.8° 59 Å$^3$=401 Å$^3$, which require 558 Å$^3$ of space in pure crystalline CH$_2$Cl$_2$ at 153 K) have been introduced into the material. In fact, the seemingly partial occupancy of CH$_2$Cl$_2$ suggests that this guest approaches the upper volume limit of what can be accommodated by the cavitand or its monoclinic empty-like phase.

TABLE 5

Calculations of the electron density in cavitand cavity using SQUEEZE. A guest occupancy was calculated from the number of electrons found and compared with that of the values obtained in the SHELXL atomistic refinement. Esds are calculated based upon occupancies derived from SHELXL, SQUEEZE and individual occupancies.

| Guest | Squeeze (e-) | Squeeze (occ.) | SCXRD occ. | Avg Occ. | St. Dev. Occ. | Individual Occupancies | | |
|---|---|---|---|---|---|---|---|---|
| | | | | | | Atom 1 | Atom 2 | Atom 3 |
| None | 1.63 | 0.163 | 0 | 0.08 | 0.12 | | | |
| CH$_4$ | 2 | 0.25 | 0.26 | 0.26 | 0.01 | | | |
| Ar | 5 | 0.28 | 0.31 | 0.29 | 0.02 | | | |
| Kr | 20 | 0.56 | 0.52 | 0.54 | 0.03 | | | |
| Xe | 41 | 0.75 | 0.79 | 0.77 | 0.03 | | | |
| C$_2$H$_4$ | 6 | 0.38 | 0.44 | 0.41 | 0.04 | 0.45 | 0.43 | |
| C$_2$H$_6$ | 13 | 0.72 | 0.71 | 0.72 | 0.02 | 0.71 | 0.74 | |
| CH$_3$F | 14 | 0.83 | 0.77 | 0.80 | 0.04 | 0.79 | 0.75 | |
| CO$_2$ | 10 | 0.45 | 0.46 | 0.46 | 0.06 | 0.53 | 0.38 | 0.44 |
| CH$_3$Cl | 23 | 0.92 | 0.87 | 0.90 | 0.03 | 0.91 | 0.86 | |
| CH$_3$Cl | 25 | 1 | 1 | 1.00 | 0.02 | 0.99 | 0.97 | |
| CH$_3$OCH$_3$ | 21 | 0.81 | 0.82 | 0.82 | 0.04 | 0.88 | 0.8 | 0.79 |
| CH$_3$CCH | 23 | 1.05 | 1 | 1.03 | 0.02 | 1.03 | 1 | 1.02 |
| CH$_3$Br | 40 | 0.93 | 0.88 | 0.91 | 0.04 | 0.95 | 0.88 | |
| CH$_3$SH | 22 | 0.85 | 0.8 | 0.83 | 0.04 | 0.87 | 0.79 | |
| EtCl | 32 | 0.94 | 0.95 | 0.95 | 0.01 | 0.95 | 0.96 | 0.93 |
| CH$_2$Cl$_2$ | 36 | 0.86 | 0.84 | 0.85 | 0.01 | 0.85 | 0.86 | 0.84 |
| CH$_3$I | 61 | 0.98 | 0.92 | 0.95 | 0.03 | 0.96 | 0.92 | |
| MeOH | 12 | 0.66 | 0.68 | 0.67 | 0.08 | 0.76 | 0.61 | |
| BrCH$_2$Cl | 45 | 0.75 | 0.75 | 0.75 | 0.00 | 0.48 | 0.67 | 1 |
| EtOH | 3 | 0.12 | 0.13 | 0.13 | 0.04 | 0.14 | 0.2 | 0.1 |
| MeCN | 20 | 0.95 | 0.97 | 0.96 | 0.03 | 0.98 | 0.99 | 1.02 |
| CH$_2$Br$_2$ | 3 | 0.04 | 0 | 0.02 | 0.03 | | | |
| NO$_2$CH$_3$ | 30 | 0.94 | 0.96 | 0.95 | 0.05 | 0.98 | 0.88 | 0.95/0.98 |
| (0.29)H$_2$O | 3 | 0.3 | 0.28 | 0.29 | 0.01 | | | |
| (0.21)H$_2$O | 1.75 | 0.18 | 0.21 | 0.20 | 0.02 | | | |
| I$_2$ | 7 | 0.066 | 0.06 | 0.06 | 0.01 | 0.07 | 0.06 | |

TABLE 6

Angles, $\tau$, between planes of all O—Si—O functionalities and the plane defined by the upper rim carbon atoms of the arene rings of formula (Ib) (see FIG. 10 for definition of $\tau$).

| Guest | Angle (Small to large) | | | | Avg. (τ̄) | St. Dev. | $\Delta\tau$ (°) | $V_g$ | $V_{cell}$ |
|---|---|---|---|---|---|---|---|---|---|
| | 1 | 2 | 3 | 4 | | | | | |
| None | 74.16 | 81.33 | 88.69 | 88.77 | 85.01 | 5.20 | 0 | | 8230 |
| Ar | 73.23 | 81.03 | 87.41 | 89.61 | 82.82 | 7.36 | 2.2 | 28 | 8225 |
| Kr | 72.42 | 80.45 | 85.67 | 87.66 | 81.55 | 6.80 | 3.5 | 35 | 8223 |
| Xe | 69.53 | 78.61 | 81.37 | 83.26 | 78.19 | 6.08 | 6.8 | 42 | 8252 |
| C$_2$H$_4$ | 70.86 | 80.43 | 85.28 | 88.08 | 81.16 | 7.56 | 3.8 | 40 | 8227 |
| C$_2$H$_6$ | 65.6 | 79.19 | 81.38 | 85.20 | 77.84 | 8.53 | 7.2 | 45 | 8236 |
| CH$_3$F | 71.37 | 79.7 | 84.23 | 86.06 | 80.34 | 6.55 | 4.7 | 32 | 8218 |
| CO$_2$ | 68.79 | 81.25 | 86 | 89.51 | 81.39 | 9.05 | 3.6 | 32 | 8214 |
| CH$_3$Cl | 66.45 | 78.72 | 78.89 | 83.04 | 76.78 | 7.17 | 8.2 | 44 | 8280 |
| CH$_3$OCH$_3$ | 58.1 | 76.9 | 82.08 | 83.70 | 75.20 | 11.76 | 9.8 | 53 | 8349 |
| CH$_3$CCH | 74.25 | 74.31 | 77.16 | 80.79 | 76.63 | 3.09 | 8.4 | 51 | |
| CH$_3$Br | 63.36 | 77.04 | 78.17 | 81.71 | 75.07 | 8.06 | 9.9 | 49 | 8307 |
| CH$_3$SH | 63.63 | 77.9 | 78.43 | 84.05 | 76.00 | 8.71 | 9.0 | 46 | 8278 |
| EtCl | 61.46 | 75.8 | 78.93 | 80.20 | 74.10 | 8.63 | 10.9 | 61 | 8446 |
| CH$_2$Cl$_2$ | 56.64 | 73.6 | 81.73 | 82.92 | 73.72 | 12.12 | 11.3 | 59 | 8378 |
| CH$_3$I | 55.88 | 75.96 | 77.21 | 78.76 | 71.95 | 10.78 | 13.1 | 53 | 8371 |
| MeOH | 69.91 | 78.37 | 85.3 | 87.76 | 80.34 | 8.01 | 4.7 | 37 | 8230 |
| ClCH$_2$Br | 57.27 | 73.81 | 82.01 | 83.29 | 74.10 | 11.98 | 10.9 | 64 | 8404 |

TABLE 6-continued

Angles, τ, between planes of all O—Si—O functionalities and the plane defined by the upper rim carbon atoms of the arene rings of formula (Ib) (see FIG. 10 for definition of τ).

| Guest | Angle (Small to large) | | | | Avg. (T) | St. Dev. | Δτ (°) | $V_g$ | $V_{cell}$ |
|---|---|---|---|---|---|---|---|---|---|
| | 1 | 2 | 3 | 4 | | | | | |
| EtOH | 72.32 | 80.86 | 87.5 | 89.94 | 82.66 | 7.89 | 2.4 | 54 | 8241 |
| MeCN | 64.54 | 78.94 | 79.01 | 83.94 | 76.61 | 8.38 | 8.4 | 44 | 8244 |
| NO₂Me | 60.62 | 72.08 | 81.19 | 82.52 | 74.10 | 10.12 | 10.9 | 51 | 8277 |
| H₂O | 74.43 | 81.42 | 88.6 | 89.22 | 83.42 | 6.96 | 1.6 | 18 | 8225 |
| I₂ | 72.91 | 80.7 | 88.18 | 89.68 | 82.87 | 7.71 | 2.1 | 60 | 8242 |

The aforementioned behavior—namely, the ultramicrocavity structure of empty formula (Ib), the isostructural and volume and/or shape-selective nature of its solvates, and the ability of the hydrophobic cavity to scavenge water from certain organic solvents—prompted an exploration of the potential for formula (Ib) to selectively capture and confine gases during the process of crystal growth. The following paragraphs detail various experiments conducted and observations made toward this end.

Example 3

Gas Complexed Cavitand Compositions of Formula (Ib)

To initially probe the ability of formula (Ib) to form stable gas clathrates, chloroform solutions of formula (Ib) were treated by passing various protic gases ($CH_3CH_2Cl$, $CH_3OCH_3$, $CH_3CH_2CH_3$, $CH_3CH=CH_2$, $CH_3C\equiv CH$, $CH_3Cl$, $CH_3F$, $CH_3CH_3$, $CH_2=CH_2$, $CH_4$) through them until the solvent had completely evaporated. The resulting solids were then rigorously flushed with nitrogen and were subsequently analyzed by $^1H$ NMR spectroscopy. The spectra showed unequivocally that exactly one equivalent of chloroethane, chloromethane, and propyne were captured by the cavitand under these conditions whereas lesser, but significant, amounts of fluoromethane (0.51(3) equivalents) and dimethylether (0.40(2) equivalents) were captured, and very small amounts of ethane (0.056(5) equivalents), ethylene (0.062(9) equivalents), acetylene (0.055(4) equivalents), and possibly methane (trace) were captured.

Notably, there was no evidence for the capture of propane or propene under these conditions. As a preliminary probe of the kinetic stability of these gas clathrates, the resulting solids were reanalyzed after seven days exposure to room temperature conditions in open vials; the results showed that, with the exception of methane, acetylene, and propyne, even extremely volatile gases such as $CH_3F$ (b.p.=−78° C.) and ethane (b.p.=−89° C.) are largely or completely retained by the host after one week. Notably, propyne, for which exactly one equivalent is captured by formula (Ib) initially, was completely missing from the solid after 7 days, an observation seemingly at odds with the observed confinement of much more volatile and less effectively captured gases.

The initial gas occupancy trends observed in the above experiments can be explained as follows. The small cavity of formula (Ib) is able to bind the gases to varying degrees in $CHCl_3$ solution, a solvent which is too large to compete for the cavity. Binding of gases and other small molecules by cavitands in solution is not new: Cram and coworkers observed that the related, more shallow-bowled cavitand (R, R¹, Y) H,Me,SiMe₂ weakly bind $CS_2$, $CH_3CCH$, and even $O_2$ in $CHCl_3$ solution, though the association constant measured for $CS_2$ (the only one measured) was very small ($K_a$=0.22 at 300 K).

Thus, enclathration of the halomethanes can be attributed to their small size, linear shape, and complementary host-guest dipole-dipole interactions, with $CH_3Cl$ and $CH_3Br$ being bound more effectively than $CH_3F$, likely for entropic reasons. Similarly, due to its complementary, linear shape and dipolar nature, one equivalent of propyne is captured by formula (Ib), though propyne is lost from the resulting solid much more rapidly than are the other gases.

Notably, despite attempts to observe it, Cram and coworkers found no evidence for the complexation of $CH_3I$ by H,Me,SiMe₂ in $CHCl_3$, or, for that matter, $CH_2Cl_2$, $H_2O$ or $CO_2$. Nonetheless, we find that each of these guests is enclathrated by formula (Ib) when crystallized under the appropriate conditions (vide infra). When a series of non-linear gases of nearly identical size and shape are compared, the xguest@formula (Ib) occupancies follow the trend: chloroethane>dimethyl ether>>propane, propene (completely excluded). These occupancies can also generally be explained on the basis of host-guest dipole-dipole interactions.

Most interesting, however, is the ability of formula (Ib) to capture and retain small amounts of the highly volatile $C_2$ hydrocarbons (ethane, ethylene, acetylene) as compared to its complete exclusion of the less volatile $C_3$ hydrocarbons propane and propene. One might expect a greater dispersion interaction between the higher surface area propane/propene and the host as compared to the $C_2$ hydrocarbons, but without being bound by theory, the former may be either: i) too large or inappropriately shaped to be accommodated by molecular cavity of the host in solution, or ii) excluded from the crystal during the process of crystal nucleation and growth, which is capable of placing further three dimensional constraints on the open-ended host cavity if the complex is to pack in the low-energy, empty-like monoclinic arrangement. Apparently, bent small molecules such as methylene chloride and chloroethane are only be taken by formula (Ib) because they offer a significant dipole to compensate for the stresses associated with their incorporation into the necessarily expanded molecular cavity.

Figure 6:
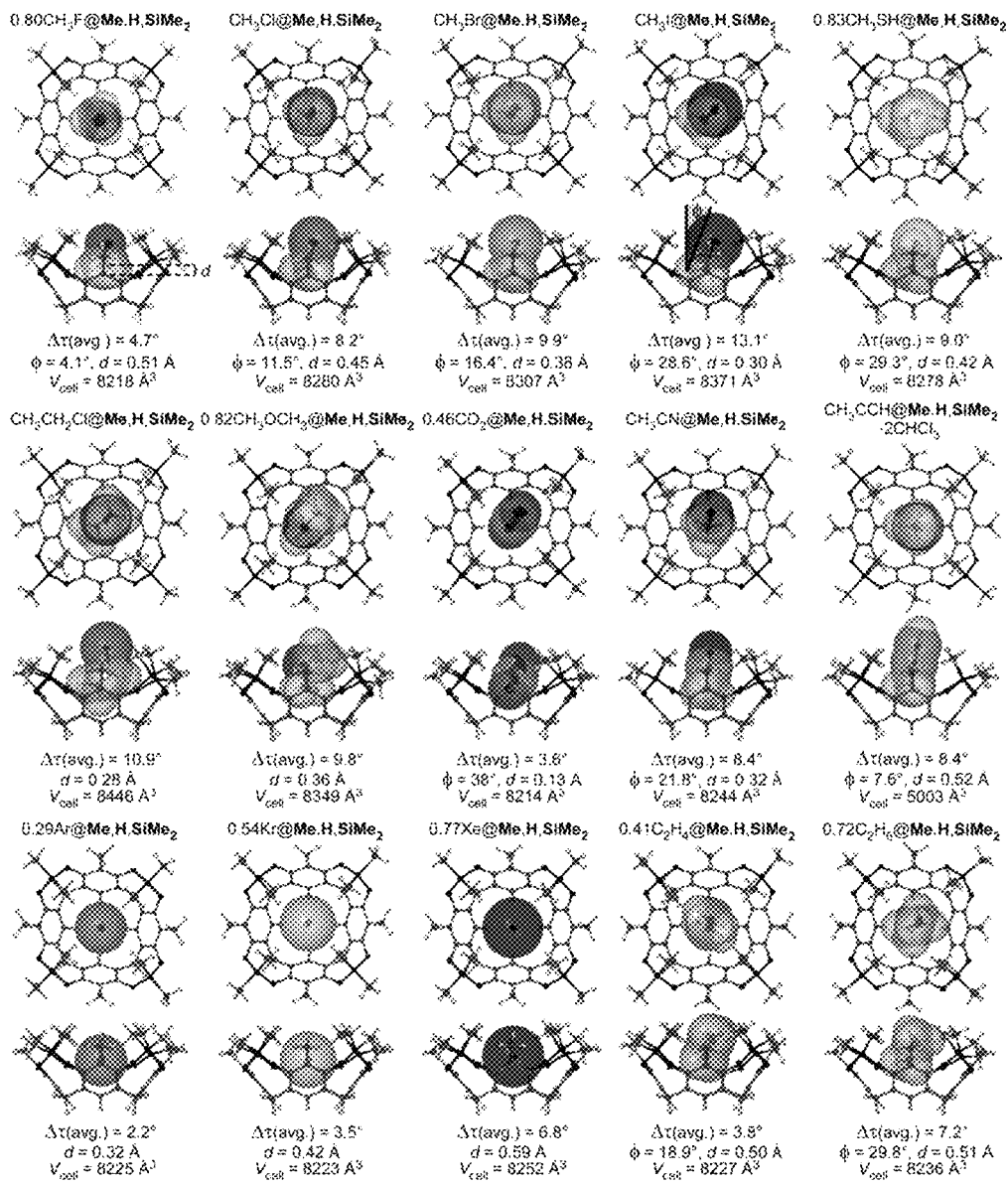
FIG. 6: Single crystal structures of several isostructural x(gas/solvent)@formula (Ib) (x≤1) clathrates, along with summary structural parameters $V_{cell}$, Δτ, φ, and d, defined in the text. The $CH_3CCH$@formula (Ib) complex is taken from the structure of $CH_3CCH$@formula (Ib).2$CHCl_3$.

To probe the structural factors at play with respect to enclathration selectivity, and to extend the investigation to non-protic gases and other small molecule guests (e.g. antisolvents), the X-ray crystal structures of numerous isostructural xguest@formula (Ib) (x≤1) clathrates were obtained. FIG. 6 depicts thermal ellipsoid plots and some pertinent structural indicators regarding many of the guest@formula (Ib) complexes. In all cases, the guest occupancies were estimated by single crystal X-ray diffraction experiments, and TGA and $^1H$ NMR obtained on the bulk samples are generally in accord with the X-ray results (with specific exceptions; see Supporting Information). Moreover, the X-ray structures of these isostructural gas clathrates are of such quality that one can place some confidence (est. ±3%) in the precision of the guest occupancies as determined by refinement of the diffraction data.

When nearly saturated chloroform solutions of formula (Ib) were briefly saturated with one atmosphere of the following gases, followed by capping of the flasks, x(gas) @formula (Ib) (x≤1) complexes precipitated as large single crystals over a period of hours to days: $CH_3F$ (x=0.80(4)), $CH_3Cl$ (x=0.90(4)), $CH_3Br$ (x=0.91(4)), $CH_3SH$ (x=0.83 (4)). That simply exposing solutions to one atmosphere of these gases induces crystallization of the gas clathrate from an otherwise unsaturated solution of formula (Ib) is significant. The lattice energy of the gas @formula (Ib) complexes is lower than that of the isostructural empty or partial hydrate phases. Thus, the observation of precipitation, and the occupancy of the resulting clathrate obtained under similar conditions is a semi-quantitative indicator of the extent of gas complexation in solution and/or the selectivity of the crystallization process.

For example, when solutions were similarly treated with non-polar gases such as ethane, ethylene, acetylene, carbon dioxide, dimethyl ether, or the Noble gases, either no precipitates formed, or crystals formed that were found by X-ray diffraction to be simple partial hydrates or seemingly very low occupancy complexes (<5%). Nonetheless, crystals of each of these gas clathrates could be obtained (except acetylene), and their structures determined, simply by growing crystals from chloroform solutions that were pressurized with the gas.

Generally, the increased solution concentration of the gas under pressurized conditions pushes the solution binding equilibrium toward complexed species, and the gas occupancy of the resulting precipitate is ultimately a factor of the gas pressure, the equilibrium constant for gas complexation in solution, and the selectivity of the crystallization process with respect to incorporation of empty or occupied molecules of formula (Ib). Certain gases required only low pressures to observe significantly occupied crystals—e.g., single crystals of $0.82CH_3OCH_3$@formula (Ib) were obtained at pressures less than the gas vapor pressure of 6 atm—whereas others required high pressures to obtain even low occupancy crystals.

For example, crystals of $0.29Ar$@formula (Ib) were obtained by sealing a vial containing formula (Ib) in $CHCl_3$ (with 3 Å molecular sieves) with liquid argon in a 23 mL teflon-lined digestion bomb and allowing the system to equilibrate at room temperature for several days; the equilibrium pressure under these conditions was not measured, but was estimated, P(est.), to be necessarily less than 70 atm.

Similarly, high pressures were required for even modest uptake of $CO_2$, but the atomic-resolution crystal structure of $0.46CO_2$@formula (Ib) could nonetheless be obtained. Crystals grown under high pressures of methane (P(est.)<60 atm) contained only trace amounts of methane (by $^1$H NMR and TGA) and the resulting single crystal structure of the putative methane clathrate was not formally distinguishable from the partial hydrate. Notably, experiments were unable to prepare formula (Ib) clathrates of propane or propene even under pressurized conditions.

The numerous single crystal structure determinations of x(gas/guest)@formula (Ib) (x≤1) clathrates constitute an unusual example of a systematic, sub-angstrom resolution exploration of the structural characteristics of small, semi-flexible nanospaces in response to molecular probes (see FIG. 6) and sheds light on structure-selectivity and structure-stability relationships in ultramicrocavity materials. Moreover, the existence of kinetically stable (vide infra) gas clathrates of formula (Ib) also provides a means to study the structure and properties of gas molecules in a highly confined environment.

It is believed that the structure determination of $0.80(4)$ $CH_3F$@formula (Ib) constitutes the first single crystal structure determination of the fluoromethane molecule (Freon 41), the determined C—F bond length (1.391(4) Å) being in accord with theory (or other experiments?1.39(x) Å). Similarly, the CSD contains only one atomic-resolution structure containing an ordered, uncoordinated ethylene molecule—pure ethylene at 85 K—and only two examples of ordered ethane—a twinned ethane crystal at 85 K and a twinned crystal of the $C_2H_6$@$C_{60}$ clathrate, another ultramicrocavity clathrate.

Some telling structural features are immediately apparent. First, the smaller, less polar, and lighter gases enclathrated by formula (Ib) (e.g. $CO_2$, $CH_3CH_3$, $H_2C=CH_2$, $CH_3F$) exhibit a greater degree of thermal motion at 100 K than do the larger, more polar, and heavier molecules bound in the xguest@formula (Ib) phase. For instance, while $CH_3F$ exhibits larger thermal parameters than the larger and heavier $CH_3Cl$, $CH_3F$ is clearly more fixed by the formula (Ib) cavity at 100 K than the larger, similar mass ethane molecule, or the heavier $CO_2$ molecule. The effect is a manifestation of the enthalpy-entropy interplay in supramolecular systems. Regardless, each of these volatile gases is found to be generally ordered within the cavity at 100 K and can be refined without restraints. For instance, the freely refined ethane C—C bond and ethylene C=C bond lengths in $0.72(2)CH_3CH_3$@formula (Ib) and $0.41(4)$ $C_2H_4$@formula (Ib) are 1.50(x) Å and 1.34(x) Å, respectively, the former value suggesting some degree of librational shortening.

The occupancies of the x(gas)@formula (Ib) (x≤1) clathrates obtained under the various preparation conditions, and the apparent strained conditions of certain larger-volume gas clathrates, suggest opportunities to apply formula (Ib) toward the separation of gases.

For instance, the non-cryogenic separation of xenon and krypton (and krypton sequestration) remains an important problem. Formula (Ib) takes more xenon than krypton at similar pressures, a trend that is in line with their chloroform solubilities and polarizabilities and the preferences of most microporous materials that are capable of accommodating xenon.

Perhaps more interesting is the fact that formula (Ib) takes up hydrocarbons with a preferential order of ethane>ethylene>>methane with complete exclusion of propane and propene. And the apparent ethane>ethylene clathrate stability order is a reversal of the thermodynamic selectivity observed by most zeolitic and Lewis acidic sorbents. A particularly exceptional manifestation of gas-selective enclathration by formula (Ib) was uncovered in experiments designed to grow single crystals of the chloroethane clathrate.

Example 4

Separation of Chloromethane and Chloroethane by Cavitand Compositions of Formula (Ib)

When a large excess of 99.7% purity chloroethane gas was passed through chloroform solutions of pure formula (Ib), the initial precipitate is single crystals of the chloromethane clathrate, $CH_3Cl$@formula (Ib), instead of the expected $CH_3CH_2Cl$@formula (Ib) clathrate. Analysis of the original chloroethane gas sample by $^1$H NMR spectroscopy revealed it to consist of an approximate 1477:1 ratio of $CH_3CH_2Cl$ to $CH_3Cl$. When the near-pure gas is passed through a concentrated $CDCl_3$ solution of formula (Ib), however, $^1$H NMR spectroscopy of the solution reveals that the cavitand serves to hold and thereby concentrate the $CH_3Cl$ in the solvent over time, effectively removing the $CH_3Cl$ from the $CH_3CH_2Cl$ stream, no doubt via selective complexation. Single crystals of the chloroethane clathrate, $CH_3CH_2Cl$@formula (Ib), had to be obtained by limiting the amount of $CH_3Cl$ available to the cavitand, treating a chloroform solution of formula (Ib) with a small volume of liquefied chloroethane under pressurized conditions.

Formula (Ib) also has utility in another gas separation of industrial significance, namely the separation of dimethyl ether and chloromethane. These gases, with identical boiling points (−24° C.), inevitably appear as mixture during the industrial synthesis of chloromethane by the action of hydrochloric acid on methanol. As the mixture cannot be separated by distillation, current methods of separation resort to aqueous liquid-liquid extraction or the wasteful destruction of $CH_3OCH_3$ by acids. Dimethyl ether is less readily included into formula (Ib) than chloromethane and forms a clearly more strained gas clathrate. As a preliminary test of the feasibility of using formula (Ib) for this separation, a pressurized, liquid, 9:1 mixture of $CH_3OCH_3$:$CH_3Cl$ was slurried with 0.1 equivalents of formula (Ib) at room temperature and the liquid was allowed to evaporate. The resulting solid contained a X:Y ratio of $CH_3Cl$:$CH_3OCH_3$, yielding a selectivity coefficient of ca. 47.

Example 5

Kinetic Stability of Gas Complexed Cavitand Compositions of Formula (Ib)

The x(gas)@formula (Ib) (x≤1) clathrates exhibit a remarkable kinetic stability. In general, heating above 100° C. is required to remove the gases from the material at a reasonable rate. For example, despite the low normal boiling points of many of the guests, the x(gas)@formula (Ib) crystals do not require any special handling and show no sign of gas loss at room temperature on a timescale of hours to months, depending upon the identity of the confined gas. As a probe of their stability, single crystals of x(gas) @formula (Ib) clathrates of the most volatile guests—x(gas) =0.29(2)Ar, 0.77(3)Xe, 0.41(4)$C_2H_4$, 0.72(2)$C_2H_6$, 0.46(6) $CO_2$, 0.80(4)$CH_3F$—were kept under ambient conditions and were again analyzed by single crystal X-ray diffraction after 7, 112, 7, 10, 10, and 146 days, respectively (the x($CH_3F$)@formula (Ib) crystal was a different crystal in the second structure determination, though a crystal from the same original batch preparation was chosen for analysis). None of the crystals lost their transparency or showed significantly diminished single crystal diffraction intensities over this time frame. With the exception of the x($CH_3F$)@formula (Ib) and x($CO_2$)@formula (Ib) crystals, which gave refined occupancies of x=0.45(11) and 0.35(5) after 146 and 10 days at room temperature, respectively, the occupancies of the other aforementioned x(gas)@formula (Ib) clathrates were identical within the estimated precision of the single crystal measurement (ca. +/−3-5%).

As an additional measure, the single crystal of 0.45(11) $CH_3F$@formula (Ib) was heated at 150° C. for four days; redetermination of the structure of this crystal gave a refined occupancy of 0.23(5) for the $CH_3F$ species. Further heating for several days at 190° C. finally emptied the crystal entirely. Similarly, numerous single crystals of the x$H_2O$@formula (Ib) (x0.30) partial hydrates could be dehydrated, also in a single crystal to single crystal fashion, by heating at 150° C. And after ten days in the oven at 100° C., the original single crystal of 0.54(3)Kr@formula (Ib) gave a single crystal that was determined to be 0.07(x)Kr@formula (Ib). In general, it was found that single crystals of the x(gas)@formula (Ib) clathrates could be readily degassed at high temperatures while preserving single crystallinity if their unit cell volumes did not appreciably contract upon emptying. Single crystal clathrates of the larger volume guests (e.g. $CH_2Cl_2$, Xe), however, tended to fracture under the stresses of degassing and/or non-uniform contraction upon high temperature guest loss.

Figure 7:
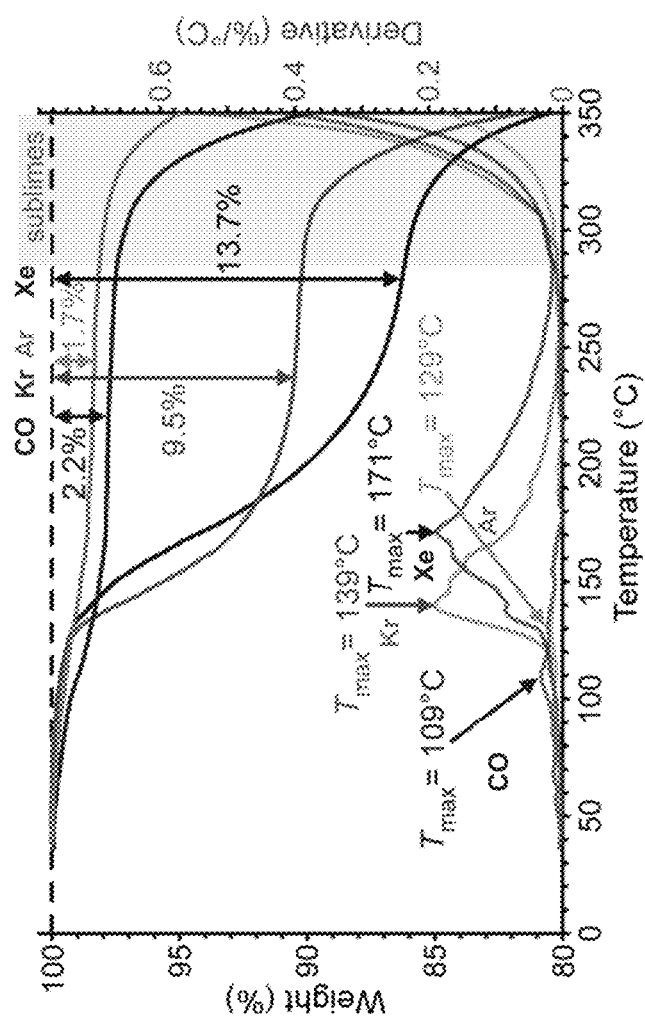
FIG. 7: a) TGA of selected x(gas)@formula (Ib) (x≤1) clathrates highlighting the unusual kinetic stability of the clathrates. The maximum of the semitransparent derivative mass loss curves is defined as $T_{max}$ and $T_{max}-T_{bp}$ (=315° C., Ar; 292° C., Kr; 279° C., Xe; 187° C., $CO_2$) may be considered a semi-quantitative measure of the relative extent of guest confinement. a) Room temperature, $P_{H2O}$=0.028(3) bar water vapor uptake kinetics as measured by SCXRD analysis of an originally empty crystal of formula (Ib). The equilibrium occupancy is 0.32$H_2O$@formula (Ib).

TGA of the bulk x(gas)@formula (Ib) samples further underscores the kinetic stability of the x(gas)@formula (Ib) clathrates. FIG. 7 shows, for example, the TGA behavior (5° C./min.) of four selected clathrates. Though the onset temperatures for gas loss are difficult to define due to the very slow release rates below 100° C., experiments found that the $T_{max}$ values, the temperature that defines the maximum rate of mass loss, are fairly reproducible (+/−5° C.) for powdered samples and serve as a practical indicator of the relative kinetic stability of the clathrates.

Moreover, the parameter $T_{max}-T_{bp}$, where $T_{bp}$ is the normal boiling point of the gas, is a useful indicator of the extent to which a material is capable of kinetically confining an otherwise volatile gas. For example, the $T_{max}$ values of the gas clathrates in FIG. 7 follow the order: $CO_2$<Ar<Kr<Xe. Though the $T_{max}$ values of this series correlate with the kinetic diameters of these gases, this behavior is not general. For example, the $T_{max}$ of the chloroethane and dimethyl ether clathrates similar since b4 and after structure ~same, Tmax reflective of diffusion rate through crystal.

The cavitand formula (Ib) was shown to bind a variety of gases under ambient conditions and at elevated pressures, including chloromethane, chloroethane and dimethyl ether (DME) (Table 7).

TABLE 7

Summary data for chloromethane, chloroethane and dimethyl ether

| Gas | MW (g/mol) | Boiling point (° C.) | Vol. (Å$^3$) | Density (g/mL) |
| --- | --- | --- | --- | --- |
| MeCl | 50.49 | −23.9 | 44 | 0.92 (20° C.) |
| EtCl | 64.52 | 12.3 | 61 | 0.924 (0° C.) |
| DME | 46.07 | −24.8 | 53 | 0.67 (20° C.) |

While attempting to grow a crystalline solvate of EtCl@formula (Ib) (the "@" symbol denotes the cavitand encapsulates the guest) by bubbling EtCl gas into a saturated solution of formula (Ib) in chloroform, the single crystals that formed contained virtually no EtCl, but MeCl instead. This was due to the cavitand's selectivity of MeCl vs. EtCl; the bulk gas contained a ratio of 1:1460, however when the gas was bubbled through the solution of cavitand, this ratio changed to 1:91. This prompted us to further probe the selectivity of this cavitand towards chloromethane.

Example 6

Separation of Chloromethane and Chloroethane from Dimethyl Ether by Cavitand Compositions of Formula (Ib)

Chloromethane is mainly produced commercially by the hydrochlorination of methanol, a process that is much more practical than the traditional methane chlorination method (Chlorinated Hydrocarbons. *Ullmann's Encyclopedia of Industrial Chemistry*, 7$^{th}$ ed; VCH: Weinheim, Germany, 2005). Synthesis is carried out in the gas phase under activated $Al_2O_3$ with excess hydrogen chloride, to drive the equilibrium towards MeCl formation, while reducing the amount of dimethyl ether side product formed (0.2 to 1%).

The residual DME is then destroyed during the MeCl purification process by passing the gaseous mixture through a 96% sulfuric acid column, forming methyl sulfate and 'onium salts'. Treatment of dimethyl ether with HCl (U.S. Pat. No. 3,981,938) or SbCl₃ (DE 2640852) back towards MeCl formation has been reported.

By utilizing the selective nature of the cavitand, methods for the destruction of side products such as DME or meticulous separations of chloroalkanes can be avoided entirely. Separation experiments that are based on selectivity of one guest over another require an inclusion preference of the host. Pairwise experiments that utilize the host and are run in the presence of both guests with known mole fractions can be used to determine the selectivity coefficient of the host ($K_{A:B}$).

$$K_{A:B} = (K_{B:A})^{-1} = Y_A/Y_B \cdot X_B/X_A \quad [1]$$

As defined by Pivovar et al., equation [1] shows the selectivity coefficient calculation where $X_A$ and $X_B$ are the mole fractions of the two competing guests in the original solution and $Y_A$ and $Y$ are the mole fractions of the two competing guests in the host (Pivovar, A. M.; Holman, K. T.; Ward, M. D. *Chem. Mater.* 2011, 13, 3018-3031).

Figure 8:
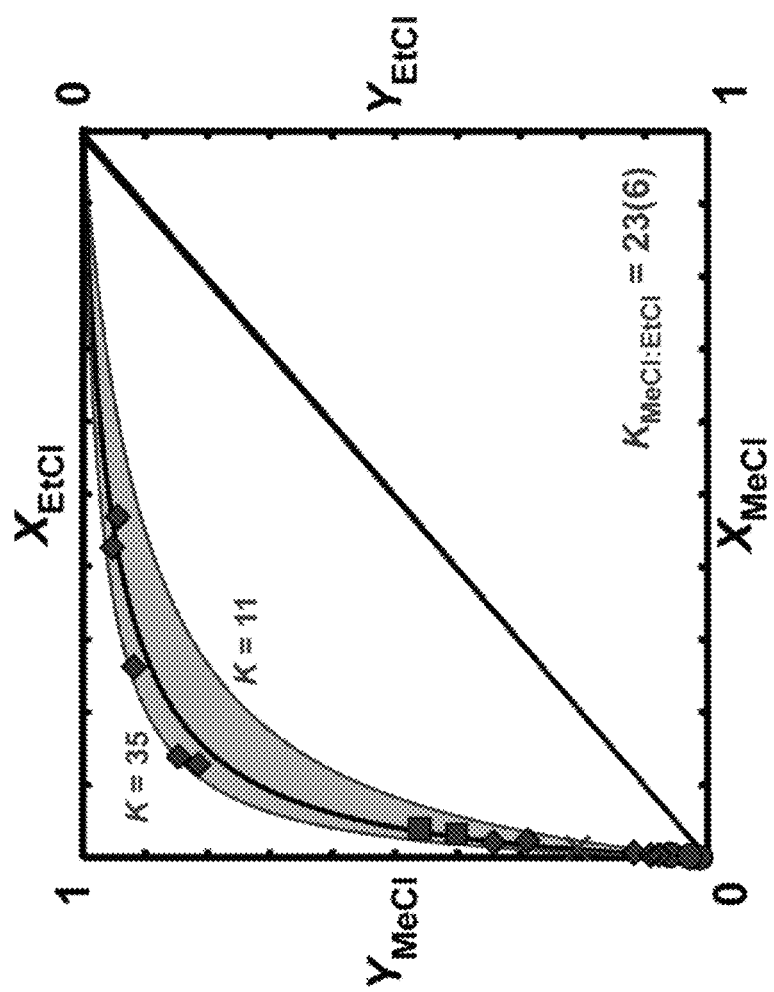
FIG. 8: Selectivity profile for MeCl vs. EtCl with formula (Ib) as a host. Diagonal line denotes no selectivity (K=1); curved lines show selectivity 2 esds above and below the determined $K_{MeCl:EtCl}$. Axes are labelled as mole fractions of both gases in the starting solution (X) and the host after the experiment (Y). Individual shapes highlight what method of competition experiments were performed for specific data point (diamond—cooling, circle—evaporation, square—precipitation, x—solid-solution).
Figure 9:
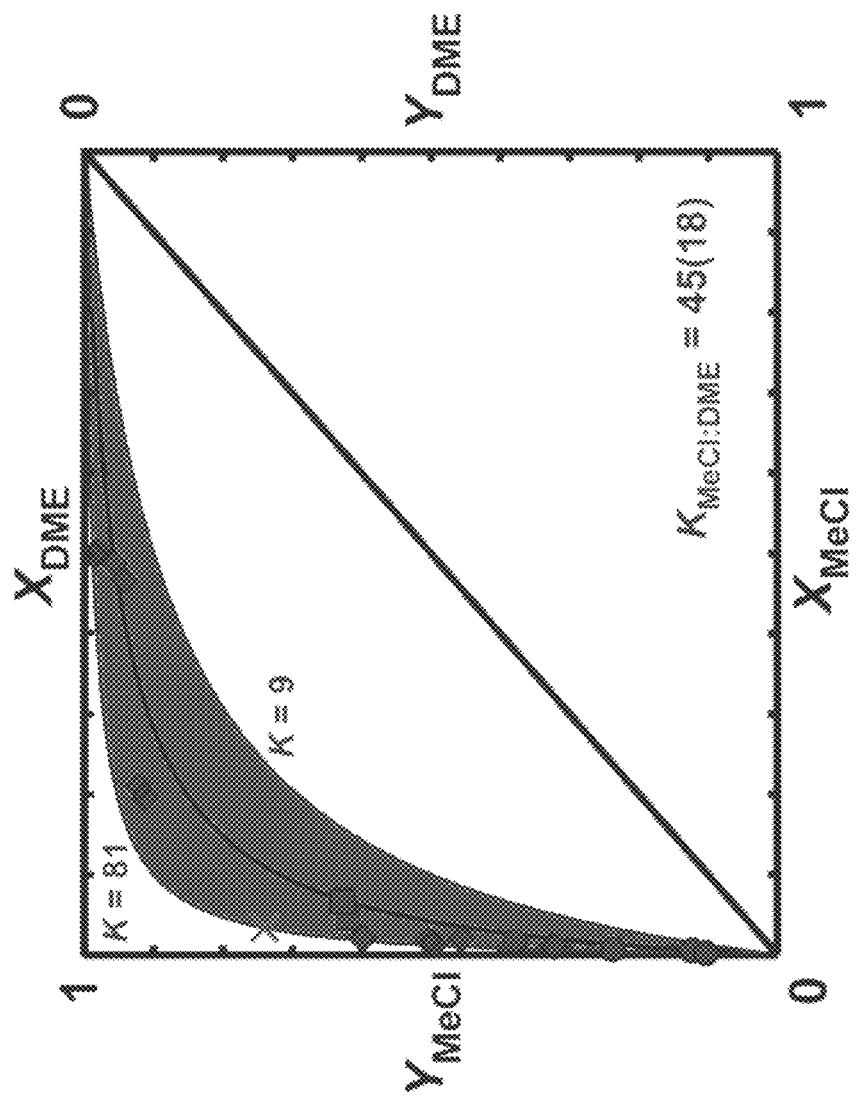
FIG. 9: Selectivity profile for MeCl vs. DME with formula (Ib) as a host. Diagonal line denotes no selectivity (K=1); curved lines show selectivity 2 esds above and below the determined $K_{MeCl:DME}$. Axes are labelled as mole fractions of both gases in the starting solution (X) and the host after the experiment (Y). Individual shapes highlight what method of competition experiments were performed for specific data point (diamond—cooling, circle—evaporation, square—precipitation, x—solid-solution).

Selectivity coefficients for $K_{MeCl:EtCl}$ and $K_{MeCl:DME}$ were determined and averaged (with esds) over numerous trials where the combined equivalents of gas bound in the cavitand were greater than 0.10. These values can be seen in FIG. 8 (MeCl vs EtCl) and FIG. 9 (MeCl vs DME). Experimental details as well as all raw data can be found in the supplementary information. The diagonal black line seen in both selectivity plots above denote no selectivity of host for any competitive guest ($K_{A:B}=1$). Curved lines for each set of competition experiments are shown as two standard deviations above and below the average selectivity coefficient calculated.

The preference of MeCl over EtCl for formula (Ib) is mainly due to guest size and geometry. Both guests have a dipole moment, however the linear shape and smaller van der Waals volume of MeCl over EtCl show inclusion of the former to be more favorable. Furthermore, single crystal structures of both inclusion complexes show very similar unit cell parameters for MeCl@formula (Ib) when compared to the native (empty) cavitand structure; there is a much larger deviation in unit cell parameters for EtCl@formula (Ib) as the cavitand must swell in order to accommodate the much larger, bent guest.

Perhaps what is more intriguing is the much larger selectivity of MeCl over DME. Since both guests have similar boiling points, typical separation methods by way of cryogenic distillation may prove to be difficult. Also, chloromethane not only has the benefit of its linear shape, but its dipole makes it inherently more thermodynamically stable than the 0.82(DME)@formula (Ib) inclusion complex, thus more likely to be bound when in competition with the non-polar DME. This effect is already seen as the DME does not fully occupy the cavitand in the solid-state and though not as pronounced of an effect as that seen with EtCl@Me,H,SiMe₃, the unit cell parameters for the DME complex are more expanded than that of the MeCl clathrate.

TABLE 8

Summary data for precipitation and single crystal competition experiments. Ratio of gases determined by ¹H NMR of gas mixture. Ratio of gases after determined by ¹H NMR of cavitand inclusion complex. SCXRD ratio was determined by the relative occupancies of both guests in the solid-solution of cavitand using SHELXL refinement. Ratios are listed with MeCl first.

| Precipitation | MeCl vs. EtCl | | MeCl vs. DME | |
|---|---|---|---|---|
| | Trial 1 | Trial 2 | Trial 1 | Trial 2 |
| Ratio before (X) | 1:24 | 1:30 | 1:21 | 1:14 |
| Ratio after (Y) | 1:1.17 | 1:1.49 | 1.63:1 | 1.68:1 |
| $K_{MeCl:EtCl\ or\ DME}$ | 21 | 20 | 34 | 24 |
| Yield | 49 mg | 58 mg | 32 mg | 41 mg |
| | 69% | 82% | 45% | 58% |
| Single Crystal | | | | |
| Ratio before (X) | 1:78 | | 1:29 | |
| Ratio after (Y) | 1:4.38 | | 3.19:1 | |
| SCXRD ratio | 1:3.23 | | 2.52:1 | |
| $K_{MeCl:EtCl\ or\ DME}$ (NMR/SCXRD) | 18/24 | | 93/73 | |

Precipitation experiments were carried out to determine the approximate yields of the inclusion compounds as well as how the selectivity may change when the experiment is performed over the course of a few minutes. Nearly saturated solutions of formula (Ib) (71 mg in 1 mL CDCl₃) were taken and added to them were liquefied gas mixtures in excess containing either more EtCl or DME over MeCl. Precipitation occurred almost immediately and the equivalents of gases included are summarized in Table 8.

The precipitation experiments show no real difference in MeCl selectivity when competed against EtCl. This observation is not congruent with MeCl vs. DME pairwise experiments. Fast precipitation of the cavitand without allowing for equilibrium to be established diminishes the chloromethane selectivity since no time is allowed for the more thermodynamic complex to form.

Figure 11:
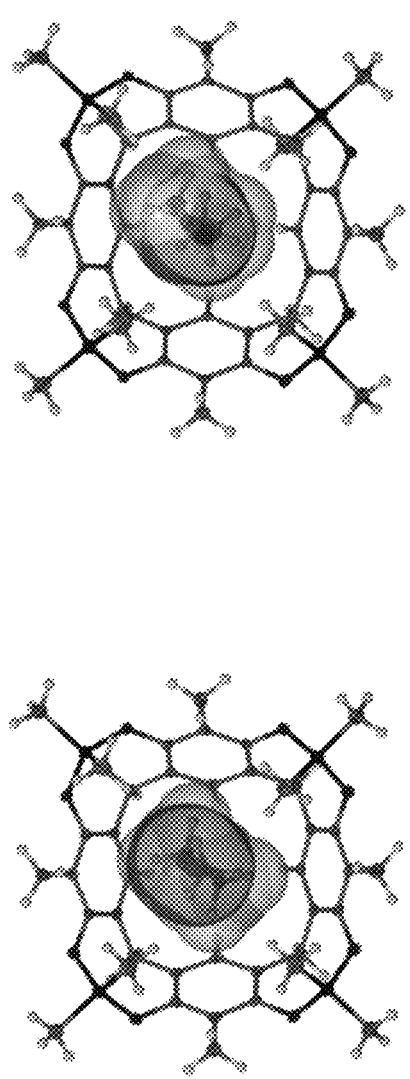
FIG. 11: Thermal ellipsoid plots of solid-solutions from competition crystal growth experiments shown with 50% probability ellipsoids.
Figure 11:
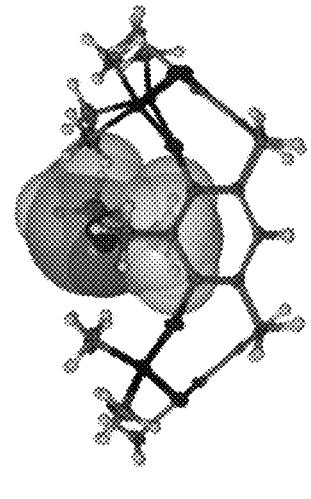
Figure 11:
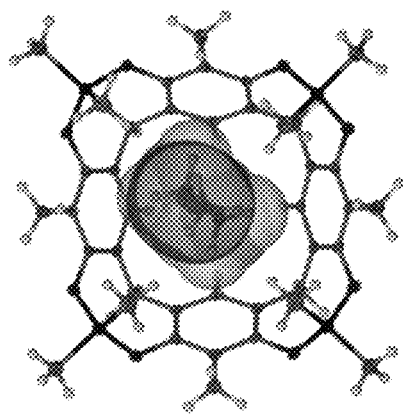
Figure 11:
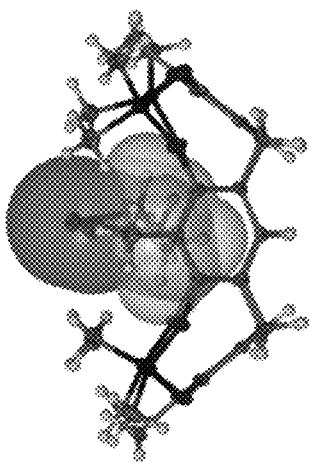

Single crystal growth of solid solutions containing both competing guests was achieved under dilute conditions (80 mg cavitand in 6 mL CDCl₃). Table 8 shows the equivalents of gas mixtures before the competition (by ¹H NMR) and the crystals after (¹H NMR and SCXRD). In all cases, the ¹H NMR was in agreement with the equivalents of gas as determined by SHELXL refinement. Chloromethane selectivity over EtCl is not improved when crystal growth conditions are employed. Using DME as the competing guest, chloromethane inclusion is enhanced as more time is given for the more thermodynamically stable complex can be formed. The thermal ellipsoid plots of the solid solutions can be seen in FIG. 11. All crystallographic information can be found in the supplementary information.

Example 7

Synthesis of H,H,SiMe₂ Cavitand

Using a different synthetic route, the parent compound H,H,SiMe₂ was also synthesized and briefly studied for gas inclusion. This parent compound lacks methyl groups on the rim of the cavitand, which inherently gives it different/confinement properties of the guests studied. Indeed, gas inclusion complexes containing DME and MeCl were isolated and studied by SCXRD. The guest free form of H,H,SiMe₂ was sublimed and its structure was determined to be the same as single crystals of the cavitand grown from ethyl acetate as the solvent is too large to complex into the cavity. Saturated ethyl acetate solutions of H,H,SiMe$_2$ (12 mg per 1 mL) were exposed to the respective gases by bubbling through the solutions for 2-3 minutes. Vials containing the solutions were then capped and heated to redissolve any precipitate that may have formed and set aside.

Single crystals formed over the course of days to weeks and studied by SCXRD. Without the presence of any other competing guest, the cavitand shows remarkable inclusion selectivity of MeCl over DME. Inclusion complex 0.91 (MeCl)@H,H,SiMe$_2$ contains a mirror plane, a slight deviation from the empty form (P2$_1$/n) however is almost fully occupied by chloromethane. Conversely, 0.03(DME).0.10 (H$_2$O)@H,H,SiMe$_2$ contains mostly water and as a result, shares the same space group as the sublimed, empty cavitand. The lack of DME inclusion is presumably due to its molecular geometry; this may also explain why we have been unable to grow single crystals of complexes containing EtCl in H,H,SiMe$_2$.

The cavity of the empty H,H,SiMe$_2$ is slightly larger than the formula (Ib) derivative using the same 1.4 Å probe radius and normalizing all C—H bonds to 1.08 Å. It would appear that it is thus better suited to accommodate the larger DME guest, however the degree for which it must expand may be too significant to form the inclusion complex. Pairwise experiments of H,H,SiMe$_2$ with MeCl/EtCl or MeCl/DME run in the same manner as described for formula (Ib) show no uptake of any gaseous guest.

Example 8

Synthesis of Empty Crystals of Formula (Ib) and Hydrate Crystals of Formula (Ib)

Calix[4]resorcinarene Me,H,OH was prepared by a literature method (Naumann, C.; Roman, E.; Peinador, C.; Ren, T.; Patrick, B. O.; Kaifer, A. E.; Sherman, J. C. *Chem. Eur. J.* 2001, 7, 1637-1645.). Cavitand formula (Ib) was prepared as follows analogous to the procedure outlined by Gibb et al. (Gibb, B. C.; Chapman, R. G.; Sherman, J. C. *J. Org. Chem.* 1996, 61, 1505-1509) for the synthesis of related cavitands and was first reported by Lara-Ochoa et al. (Lara-Ochoa, F.; Garcia, M. M.; Teran, R.; Almaza, R. C.; Espinoza-Perez, G.; Chen, G.; Silaghi-Dumitrescu, I. *Supramol. Chem.* 2000, 11, 263).

x(H$_2$O)@formula (Ib) (x(H$_2$O)@C$_{40}$H$_{48}$O$_8$Si$_4$)

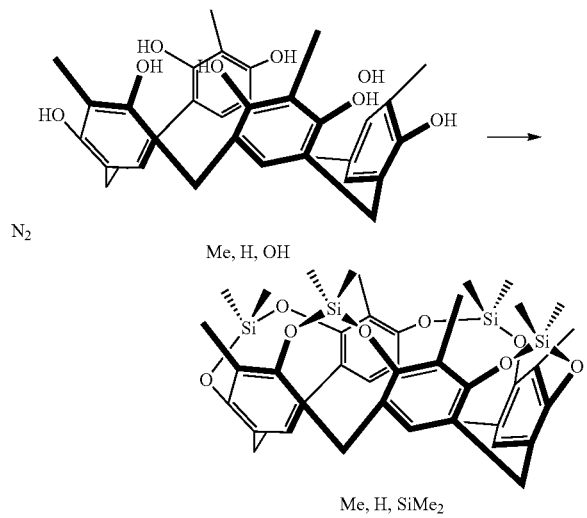

Under atmosphere, calix[4]resorcinarene Me,H,OH (3.0 g, 5.5 mmol) was dissolved in pyridine (180 mL), dichlorodimethylsilane (7.11 g, 6.64 mL, 55.1 mmol) was rapidly added and the mixture was stirred for 48 hours at room temperature. The solvent was then removed in vacuo and methanol was added (250 mL) to quench any unreacted Cl$_2$SiMe$_2$ and the solvent was removed by rotary evaporation. The material was triterated with methanol and the off-white solid was filtered and dried. The crude material was then dissolved in chloroform and run through a silica gel plug to give the pure product as a partial hydrate in 68% yield (1.45 g, 1.88 mmol). M.P.=320-322° C. (onset of sublimation). $^1$H NMR (400 MHz, CDCl$_3$): δ=7.16 (s, 4H, ArH$_{bottom}$), 4.26 (d, $^2$J$_{HH}$=13.1 Hz, 4H, CH$_{2(out)}$), 3.35 (d, $^2$J$_{HH}$=13.1 Hz, 4H, CH$_{2(in)}$), 1.93 (s, 12H, ArCH$_3$), 0.52 (s, 12H, SiCH$_{3(out)}$), −0.63 (s, 12H, SiCH$_{3(in)}$) ppm. $^{13}$C NMR (100 MHz, CDCl$_3$): δ=148.63, 128.09, 127.03, 119.76, 32.25, 10.33, −3.03, −6.23 ppm.

A single crystal of the partial cavitand hydrate 0.21(H$_2$O) @formula (Ib) was obtained by slow evaporation of formula (Ib) from wet chloroform solution. A peak of 1.79 e$^-$/Å$^3$ was centered in the cavity and was modeled as a partial H$_2$O, refining to an occupancy of 0.21. Electron density SQUEEZE analysis estimated 1.75 e$^-$ per cavitand cavity, corresponding to 0.18 eq. H$_2$O, this improved R$_1$ by 10% (0.0519 to 0.0473).

Empty Formula (Ib)

This crystal was then subsequently dehydrated at 150° C. for 1 week in a single-crystal-to-single-crystal fashion. A second data collection was performed on the crystal, which showed no peak (0.25 e$^-$/Å$^3$ well offset from the center of the cavity). SQUEEZE analysis of this structure gave 1.63 e$^-$ per cavitand cavity. This demonstrates that the cavities are empty. A room temperature collection was obtained on another empty crystal that was prepared from the partial hydrate in the same manner as described above.

Crystal rehydration was carried out by placing the empty formula (Ib) crystal into a humidity chamber (100% RH) for 1 week at room temperature. Data collection of this crystal revealed a peak of 2.59 e$^-$/Å$^3$, which refined to 0.28 occupancy of an oxygen atom (R$_1$ improves from 0.0531 to 0.0447). SQUEEZE analysis estimates 3 electrons per cavitand cavity, corresponding to an occupancy of 0.30 eq. of H$_2$O.

Example 9

Synthesis and Analysis of x(Guest)@Formula (Ib)

Half saturated solutions of empty formula (Ib) (generated by placing x(H$_2$O)@formula (Ib) in the oven at 150° C. for at least 2 days) in chloroform (solubility ~80 mg/mL) were prepared and select gases were bubbled through the solutions until the chloroform evaporated and the resulting precipitated solids were dry. Nitrogen gas was then used to purge any remaining gas vapors from the vial before NMR measurements (~3 mins.). $^1$H NMR spectra of the solids were obtained in CDCl$_3$ or acetone-d$_6$ and the solid samples were again analyzed after 7 days of standing in ambient conditions. Multiple trials of these experiments were carried out for select gases to ascertain errors for the measurements. These spectra are denoted as day 0 or day 7 bubbling to dryness experiments for a variety of gases and are shown in the Synthesis and Characterization section. The integrations in the spectra for the guest and host protons are normalized to determine equivalents of gas. In some instances, the signals of the guest overlap with signals of the host; in this case, the integrations of the combined signals are subtracted from the integration of a peak solely corresponding to the host and subsequently normalized to determine equivalents.

Samples obtained from gas clathrates under pressurized conditions were analyzed the same way as described above. The day 0 and day 7 spectra are given for each sample in the Synthesis and Characterization section. In the instances where the included guest do not have any protons for analysis, only a day 0 spectra was taken to check for proton-containing impurities and to ensure that observed TGA mass losses are not due to impurities.

xCH$_3$F@Formula (Ib)

Single crystals 0.80(CH$_3$F)@formula (Ib) (table S4) were obtained by bubbling fluoromethane into a saturated solution (approx. 0.1 M) of formula (Ib) in CHCl$_3$ until a precipitate formed, capping the glass vial and reheating to dissolve the remaining precipitate after which crystals formed over days. SHELXL and SQUEEZE analysis estimated 0.77 and 0.83 eq. of CH$_3$F per cavitand, respectively (average=0.80(4) eq./cavitand). Analysis of other crystals from batches prepared in the same manner gave the same occupancies within error. Data collection of another crystal from the same batch shows a reduced fluoromethane occupancy of 0.43 eq. (after four months under ambient conditions) (table S4). In analogy to that of the hydrate, this crystal was then heated at 150° C. for four days and its structure was re-determined by SCXRD; the occupancy was found to be 0.23 eq. CH$_3$F per cavitand. Subsequent heating of the same crystal at 190° C. for 1 more week yielded the empty formula (Ib) crystal as shown by SCXRD analysis. These latter two collections have been omitted from the crystallographic data tables (below) due to their redundancy with already reported structures, but the data is available upon request.

xKr@Formula (Ib)

Single crystals of x(Kr)@formula (Ib) were grown under elevated pressures by the following procedure. About 3±0.25 mL of krypton was condensed in a cooled graduated cylinder and was poured into a cooled Teflon bomb (23 mL capacity) that was cooled in liquid nitrogen. A 1 mL saturated solution of formula (Ib) in CHCl$_3$ with activated 3 Å molecular sieves in an uncapped GC-MS vial (1.5 mL capacity) was immediately placed into the cooled Teflon bomb with the liquefied krypton. The bomb was quickly sealed in a metal jacket and set aside for 1-2 weeks. The bomb was re-opened and the crystals of x(Kr)@formula (Ib) were filtered off. A single crystal from the batch was studied by SCXRD and its composition was found to be 0.54(3) (Kr)@formula (Ib) (table S7) according to SHELXL refinement and SQUEEZE treatment of the data. Another single crystal from the same batch was found to have 0.50 eq. of Kr per cavitand (not reported). The original crystal was then heated at 100° C. for two weeks and a subsequent SHELXL refinement showed a peak of 4.44 e$^-$/Å$^3$ that was centered in the cavity. The SQUEEZE subroutine gave 2.75 e$^-$ per cavitand cavity corresponding to 0.07 eq. Kr. The electron density and peak position allows the conclusion that the electrons correspond to residual krypton. Overall the SCXRD correlates with the 0.07(Kr)@formula (Ib) inclusion complex.

TABLE S2

Crystallographic data for x(guest)@formula (Ib)

| Crystal Parameters | formula (Ib)[a] | formula (Ib)[b] | 0.21(H$_2$O)@formula (Ib)[a] | 0.29(H$_2$O)@formula (Ib)[a] |
|---|---|---|---|---|
| Chemical formula | C$_{40}$H$_{48}$O$_8$Si$_4$ | C$_{40}$H$_{48}$O$_8$Si$_4$ | C$_{40}$H$_{48.44}$O$_{8.21}$Si$_4$ | C$_{40}$H$_{48.58}$O$_{8.29}$Si$_4$ |
| Formula weight, g/mol | 769.14 | 769.14 | 772.52 | 774.36 |
| Growth Solvent | CHCl$_3$ | CHCl$_3$ | CHCl$_3$ | CHCl$_3$ |
| Crystal system | Monoclinic | Monoclinic | Monoclinic | Monoclinic |
| Space group | C2/c | C2/c | C2/c | C2/c |
| Z | 8 | 8 | 8 | 8 |
| a, Å | 23.8783 (24) | 23.9160 (31) | 23.8959 (28) | 23.8634 (18) |
| b, Å | 8.3377 (9) | 8.4243 (11) | 8.3362 (10) | 8.3296 (6) |
| c, Å | 42.1053 (43) | 42.4217 (55) | 42.0987 (49) | 42.0507 (32) |
| α, deg | 90 | 90 | 90 | 90 |
| β, deg | 100.631 (1) | 100.521 (2) | 100.506 (1) | 100.508 (1) |
| γ, deg | 90 | 90 | 90 | 90 |
| V, Å$^3$ | 8238.9 (15) | 8403.2 (19) | 8245.5 (17) | 8218.3 (11) |
| ρ$_{calc}$, g/cm$^3$ | 1.24 | 1.22 | 1.24 | 1.25 |
| crystal dimensions, mm | 1.6 × 1.5 × 0.96 | 0.82 × 0.63 × 0.36 | 1.6 × 1.5 × 0.96 | 1.6 × 1.5 × 0.96 |
| T, K | 100 (2) | 296 (2) | 100 (2) | 100 (2) |
| 2Θ max for refinement, deg | 56.0 | 56.0 | 56.0 | 56.0 |
| total reflections | 34790 | 31870 | 35219 | 31061 |
| independent reflections | 9663 | 9900 | 9653 | 9631 |
| no. of observed data | 7342 | 5314 | 6795 | 7799 |
| no. of parameters | 477 | 477 | 490 | 490 |
| R$_{int}$ | 0.0455 | 0.0741 | 0.1154 | 0.0365 |
| μ, mm$^{-1}$ | 0.193 | 0.189 | 0.194 | 0.195 |
| R$_1$(F), wR$_2$(F$^2$), (I > 2σ(I)) | 0.0473, 0.1309 | 0.0447, 0.1019 | 0.0473, 0.1166 | 0.0447, 0.1146 |
| Goodness-of-fit on F$^2$ | 1.066 | 0.861 | 0.972 | 0.85 |
| CCDC Depository Number | 895245 | 895246 | 895247 | 895248 |

[a]Same crystal
[b]Note: room temp. data.

TABLE S3

Crystallographic data for x(guest)@formula (Ib)

| Crystal Parameters | CH$_3$I@formula (Ib) | CH$_3$Br@formula (Ib) | CH$_3$Cl@formula (Ib) | CH$_3$Cl@formula (Ib) |
|---|---|---|---|---|
| Chemical formula | C$_{41}$H$_{53}$O$_8$Si$_4$I | C$_{41}$H$_{53}$O$_8$Si$_4$Br | C$_{41}$H$_{51}$O$_8$Si$_4$Cl | C$_{41}$H$_{51}$O$_8$Si$_4$Cl |
| Formula weight, g/mol | 911.08 | 864.09 | 819.63 | 819.63 |
| Growth Solvent | CHCl$_3$ | CHCl$_3$ | CHCl$_3$ | EtOAc |
| Crystal system | Monoclinic | Monoclinic | Monoclinic | Monoclinic |
| Space group | C2/c | C2/c | C2/c | C2/c |
| Z | 8 | 8 | 8 | 8 |
| a, Å | 23.7418 (15) | 23.7815 (29) | 23.8190 (24) | 23.7820 (26) |
| b, Å | 8.3761 (5) | 8.3577 (10) | 8.3375 (9) | 8.3354 (9) |
| c, Å | 42.6673 (28) | 42.3173 (52) | 42.2158 (43) | 42.2278 (46) |
| α, deg | 90 | 90 | 90 | 90 |
| β, deg | 99.403 (1) | 98.998 (2) | 99.032 (1) | 98.903 (1) |
| γ, deg | 90 | 90 | 90 | 90 |
| V, Å$^3$ | 8371.0 (9) | 8307.4 (17) | 8279.7 (15) | 8270.1 (16) |
| ρ$_{calc}$, g/cm$^3$ | 1.47 | 1.38 | 1.32 | 1.32 |
| crystal dimensions, mm | 0.60 × 0.42 × 0.27 | 0.23 × 0.17 × 0.13 | 1.0 × 0.70 × 0.70 | 0.53 × 0.20 × 0.20 |
| T, K | 100 (2) | 100 (2) | 100 (2) | 100 (2) |
| 2Θ max for refinement, deg | 56.0 | 56.0 | 56.0 | 56.0 |
| total reflections | 31937 | 94190 | 35918 | 31511 |
| independent reflections | 9883 | 10023 | 9807 | 9757 |
| no. of observed data | 7621 | 8773 | 7609 | 6733 |
| no. of parameters | 501 | 501 | 501 | 501 |
| R$_{int}$ | 0.0464 | 0.0538 | 0.0517 | 0.0658 |
| μ, mm$^{-1}$ | 0.93 | 1.156 | 0.259 | 0.259 |
| R$_1$(F), wR$_2$(F$^2$), (I > 2σ(I)) | 0.0515, 0.1231 | 0.0537, 0.1286 | 0.0521, 0.1351 | 0.0481, 0.1045 |
| Goodness-of-fit on F$^2$ | 1.176 | 1.351 | 1.06 | 1.05 |
| CCDC Depository Number | 895249 | 895250 | 895251 | 895252 |

TABLE S4

Crystallographic data for x(guest)@formula (Ib)

| Crystal Parameters | 0.80(CH$_3$F)@formula (Ib) | 0.43(CH$_3$F)@formula (Ib)$^a$ | EtCl@formula (Ib) | 0.74(BrCH$_2$Cl)@formula (Ib) |
|---|---|---|---|---|
| Chemical formula | C$_{40.8}$H$_{50.4}$O$_8$Si$_4$F$_{0.80}$ | C$_{40.43}$H$_{49.29}$O$_8$Si$_4$F$_{0.43}$ | C$_{42}$H$_{55}$O$_8$Si$_4$Cl | C$_{40.74}$H$_{59.48}$O$_8$Si$_4$Cl$_{0.74}$Br$_{0.74}$ |
| Formula weight, g/mol | 796.37 | 783.78 | 829.80 | 864.90 |
| Growth Solvent | CHCl$_3$ | CHCl$_3$ | CHCl$_3$ | BrCH$_2$Cl |
| Crystal system | Monoclinic | Monoclinic | Monoclinic | Monoclinic |
| Space group | C2/c | C2/c | C2/c | C2/c |
| Z | 8 | 8 | 8 | 8 |
| a, Å | 23.8281 (25) | 23.8507 (27) | 23.5981 (20) | 23.7650 (20) |
| b, Å | 8.3065 (9) | 8.3122 (9) | 8.4762 (7) | 8.4219 (7) |
| c, Å | 42.1464 (44) | 42.1008 (47) | 42.8436 (35) | 42.7905 (36) |
| α, deg | 90 | 90 | 90 | 90 |
| β, deg | 99.653 (1) | 100.069 (1) | 99.750 (1) | 101.108 (1) |
| γ, deg | 90 | 90 | 90 | 90 |
| V, Å$^3$ | 8223.8 (15) | 8218.0 (16) | 8445.9 (12) | 8403.9 (12) |
| ρ$_{calc}$, g/cm$^3$ | 1.29 | 1.27 | 1.31 | 1.37 |
| crystal dimensions, mm | 1.49 × 0.38 × 0.26 | 0.86 × 0.67 × 0.29 | 0.76 × 0.33 × 0.32 | 0.82 × 0.43 × 0.21 |
| T, K | 100 (2) | 100 (2) | 100 (2) | 100 (2) |
| 2Θ max for refinement, deg | 56.0 | 56.0 | 56.0 | 56.0 |
| total reflections | 31049 | 31231 | 36561 | 35425 |
| independent reflections | 9667 | 9656 | 10002 | 9891 |
| no. of observed data | 7338 | 6756 | 8408 | 7435 |
| no. of parameters | 501 | 501 | 510 | 541 |

TABLE S4-continued

Crystallographic data for x(guest)@formula (Ib)

| Crystal Parameters | 0.80(CH$_3$F)@formula (Ib) | 0.43(CH$_3$F)@formula (Ib)[a] | EtCl@formula (Ib) | 0.74(BrCH$_2$Cl)@formula (Ib) |
|---|---|---|---|---|
| R$_{int}$ | 0.0506 | 0.0567 | 0.0311 | 0.0427 |
| μ, mm$^{-1}$ | 0.199 | 0.196 | 0.251 | 0.943 |
| R$_1$(F), wR$_2$(F$^2$), (I > 2σ(I)) | 0.0540, 0.1103 | 0.0503, 0.1148 | 0.0411, 0.0953 | 0.0555, 0.1208 |
| Goodness-of-fit on F$^2$ | 1.048 | 1.064 | 1.019 | 1.044 |
| CCDC Depository Number | 895253 | 895254 | 895255 | 895256 |

[a]Different crystal, from the same batch as 0.80(CH$_3$F)@formula (Ib) but after 4 months at ambient conditions.

TABLE S5

Crystallographic data for x(guest)@formula (Ib)

| Crystal Parameters | 0.85(CH$_2$Cl$_2$)@formula (Ib) | 0.82(CH$_3$OCH$_3$)@formula (Ib) | 0.83(CH$_3$SH)@formula (Ib) | 0.06(I$_2$)@formula (Ib) |
|---|---|---|---|---|
| Chemical formula | C$_{40.85}$H$_{49.7}$O$_8$Si$_4$Cl$_{1.7}$ | C$_{41.64}$H$_{52.92}$O$_{8.82}$Si$_4$ | C$_{40.83}$H$_{51.32}$O$_8$Si$_4$S$_{0.83}$ | C$_{40}$H$_{48}$O$_8$Si$_4$I$_{0.12}$ |
| Formula weight, g/mol | 841.35 | 806.94 | 809.09 | 784.37 |
| Growth Solvent | CH$_2$Cl$_2$ | CHCl$_3$ | CHCl$_3$ | CHCl$_3$ |
| Crystal system | Monoclinic | Monoclinic | Monoclinic | Monoclinic |
| Space group | C2/c | C2/c | C2/c | C2/c |
| Z | 8 | 8 | 8 | 8 |
| a, Å | 23.8439 (22) | 23.8115 (22) | 23.8489 (14) | 23.8600 (12) |
| b, Å | 8.3749 (8) | 8.3707 (8) | 8.3186 (5) | 8.3389 (4) |
| c, Å | 42.7877 (39) | 42.6458 (40) | 42.2892 (26) | 42.1352 (22) |
| α, deg | 90 | 90 | 90 | 90 |
| β, deg | 101.337 (1) | 100.829 (1) | 99.377 (1) | 100.525 (1) |
| γ, deg | 90 | 90 | 90 | 90 |
| V, Å$^3$ | 8377.6 (13) | 8348.7 (14) | 8277.6 (9) | 8242.4 (7) |
| ρ$_{calc}$, g/cm$^3$ | 1.33 | 1.28 | 1.30 | 1.26 |
| crystal dimensions, mm | 0.36 × 0.26 × 0.26 | 0.87 × 0.72 × 0.11 | 0.47 × 0.15 × 0.11 | 0.47 × 0.38 × 0.07 |
| T, K | 100 (2) | 100 (2) | 100 (2) | 100 (2) |
| 2Θ max for refinement, deg | 56.0 | 56.0 | 56.0 | 56.0 |
| total reflections | 36480 | 31519 | 109616 | 35677 |
| independent reflections | 9939 | 9787 | 9981 | 9737 |
| no. of observed data | 7379 | 7632 | 9164 | 7451 |
| no. of parameters | 508 | 511 | 501 | 508 |
| R$_{int}$ | 0.0467 | 0.0459 | 0.0411 | 0.042 |
| μ, mm$^{-1}$ | 0.301 | 0.195 | 0.236 | 0.283 |
| R$_1$(F), wR$_2$(F$^2$), (I > 2σ(I)) | 0.0461, 0.1059 | 0.0522, 0.1195 | 0.0501, 0.1182 | 0.0556, 0.1270 |
| Goodness-of-fit on F$^2$ | 1.051 | 1.031 | 1.131 | 1.056 |
| CCDC Depository No. | 895257 | 895258 | 895259 | 895271 |

TABLE S6

Crystallographic data for x(guest)@formula (Ib)

| Crystal Parameters | 0.72(C$_2$H$_6$)@formula (Ib)[a] | 0.75(C$_2$H$_6$)@formula (Ib)[a] | 0.77(Xe)@formula (Ib) | 0.79(Xe)@formula (Ib)[b] |
|---|---|---|---|---|
| Chemical formula | C$_{41.44}$H$_{52.32}$O$_8$Si$_4$ | C$_{41.50}$H$_{52.50}$O$_8$Si$_4$ | C$_{40}$H$_{48}$O$_8$Si$_4$Xe$_{0.77}$ | C$_{40}$H$_{48}$O$_8$Si$_4$Xe$_{0.79}$ |
| Formula weight, g/mol | 790.79 | 791.71 | 870.24 | 872.88 |
| Growth Solvent | CHCl$_3$ | CHCl$_3$ | CHCl$_3$ | CHCl$_3$ |
| Crystal system | Monoclinic | Monoclinic | Monoclinic | Monoclinic |
| Space group | C2/c | C2/c | C2/c | C2/c |
| Z | 8 | 8 | 8 | 8 |

TABLE S6-continued

Crystallographic data for x(guest)@formula (Ib)

| Crystal Parameters | 0.72($C_2H_6$)@formula (Ib)[a] | 0.75($C_2H_6$)@formula (Ib)[a] | 0.77(Xe)@formula (Ib) | 0.79(Xe)@formula (Ib)[b] |
|---|---|---|---|---|
| a, Å | 23.7918 (15) | 23.8033 (13) | 23.7847 (20) | 23.7967 (66) |
| b, Å | 8.3456 (5) | 8.3453 (4) | 8.3252 (7) | 8.3333 (23) |
| c, Å | 42.2677 (26) | 42.2733 (23) | 42.2368 (35) | 42.2748 (117) |
| α, deg | 90 | 90 | 90 | 90 |
| β, deg | 99.785 (1) | 99.789 (1) | 99.359 (1) | 99.380 (4) |
| γ, deg | 90 | 90 | 90 | 90 |
| V, Å$^3$ | 8270.5 (10) | 8275.1 (8) | 8252.1 (12) | 8271 (4) |
| $\rho_{calc}$, g/cm$^3$ | 1.27 | 1.27 | 1.40 | 1.40 |
| crystal dimensions, mm | 0.60 × 0.36 × 0.35 | 0.60 × 0.36 × 0.35 | 0.40 × 0.20 × 0.12 | 0.45 × 0.11 × 0.10 |
| T, K | 100 (2) | 100 (2) | 100 (2) | 100 (2) |
| 2Θ max for refinement, deg | 56.0 | 56.0 | 56.0 | 56.0 |
| total reflections | 31373 | 35753 | 30957 | 34741 |
| independent reflections | 9719 | 9738 | 9679 | 9737 |
| no. of observed data | 7880 | 8704 | 7851 | 6909 |
| no. of parameters | 501 | 503 | 490 | 491 |
| $R_{int}$ | 0.0383 | 0.0248 | 0.0458 | 0.069 |
| μ, mm$^{-1}$ | 0.194 | 0.194 | 0.815 | 0.83 |
| $R_1(F)$, $wR_2(F^2)$, (I > 2σ(I)) | 0.0500, 0.1101 | 0.0515, 0.1155 | 0.0559, 0.1061 | 0.0564, 0.1238 |
| Goodness-of-fit on $F^2$ | 1.062 | 1.140 | 1.161 | 1.085 |
| CCDC Depository Number | 895260 | 895261 | 895262 | 895263 |

[a] Same crystal, the 2$^{nd}$ data collection occurring after 10 days at ambient conditions.
[b] Different crystal from the same batch as 0.77(Xe)@formula (Ib) but after 129 days at ambient conditions.

TABLE S7

Crystallographic data for x(guest)@formula (Ib)

| Crystal Parameters | 0.41($C_2H_4$)@formula (Ib)[a] | 0.43($C_2H_4$), 0.22($H_2O$)@formula (Ib)[a] | 0.54(Kr)@formula (Ib) | 0.07(Kr)@formula (Ib)[b] |
|---|---|---|---|---|
| Chemical formula | $C_{40.82}H_{49.64}O_8Si_4$ | $C_{40.86}H_{50.16}O_{8.22}Si_4$ | $C_{40}H_{48}O_8Si_4Kr_{0.54}$ | $C_{40}H_{48}O_8Si_4Kr_{0.07}$ |
| Formula weight, g/mol | 780.65 | 785.19 | 814.4 | 775.03 |
| Growth Solvent | CHCl$_3$ | CHCl$_3$ | CHCl$_3$ | CHCl$_3$ |
| Crystal system | Monoclinic | Monoclinic | Monoclinic | Monoclinic |
| Space group | C2/c | C2/c | C2/c | C2/c |
| Z | 8 | 8 | 8 | 8 |
| a, Å | 23.8487 (12) | 23.8543 (13) | 23.8156 (27) | 23.8513 (17) |
| b, Å | 8.3237 (4) | 8.3318 (4) | 8.3314 (10) | 8.3338 (6) |
| c, Å | 42.0407 (21) | 42.0514 (22) | 42.0998 (48) | 42.0596 (30) |
| α, deg | 90 | 90 | 90 | 90 |
| β, deg | 99.880 (1) | 99.836 (1) | 99.948 (1) | 100.528 (1) |
| γ, deg | 90 | 90 | 90 | 90 |
| V, Å$^3$ | 8226.6 (7) | 8234.8 (7) | 8227.7 (17) | 8219.5 (10) |
| $\rho_{calc}$, g/cm$^3$ | 1.26 | 1.27 | 1.32 | 1.25 |
| crystal dimensions, mm | 0.58 × 0.31 × 0.19 | 0.58 × 0.31 × 0.19 | 0.50 × 0.34 × 0.22 | 0.49 × 0.14 × 0.11 |
| T, K | 100 (2) | 100 (2) | 100 (2) | 100 (2) |
| 2Θ max for refinement, deg | 56.0 | 56.0 | 56.0 | 56.0 |
| total reflections | 34703 | 31321 | 34877 | 34617 |
| independent reflections | 9663 | 9729 | 9740 | 9686 |
| no. of observed data | 7762 | 7763 | 6170 | 6518 |
| no. of parameters | 499 | 504 | 491 | 491 |
| $R_{int}$ | 0.0332 | 0.195 | 0.771 | 0.0691 |
| μ, mm$^{-1}$ | 0.195 | 0.0363 | 0.0814 | 0.269 |
| $R_1(F)$, $wR_2(F^2)$, (I > 2σ(I)) | 0.0428, 0.1038 | 0.0441, 0.1065 | 0.0411, 0.0877 | 0.0540, 0.1118 |
| Goodness-of-fit on $F^2$ | 1.039 | 1.041 | 0.812 | 1.026 |

TABLE S7-continued

Crystallographic data for x(guest)@formula (Ib)

| Crystal Parameters | 0.41($C_2H_4$)@formula (Ib)[a] | 0.43($C_2H_4$), 0.22($H_2O$)@formula (Ib)[a] | 0.54(Kr)@formula (Ib) | 0.07(Kr)@formula (Ib)[b] |
|---|---|---|---|---|
| CCDC Depository No. | 895264 | 895265 | 895266 | 895267 |

TABLE S8

Crystallographic data for x(guest)@formula (Ib)

| Crystal Parameters | 0.29(Ar)@formula (Ib)[a] | 0.25(Ar)@formula (Ib)[a] | 0.46($CO_2$)@formula (Ib)[b] | 0.36($CO_2$)@formula (Ib)[b] |
|---|---|---|---|---|
| Chemical formula | $C_{40}H_{48}O_8Si_4Ar_{0.29}$ | $C_{40}H_{48}O_8Si_4Ar_{0.25}$ | $C_{40.46}H_{48}O_{8.92}Si_4$ | $C_{40.36}H_{48}O_{8.72}Si_4$ |
| Formula weight, g/mol | 780.73 | 779.15 | 789.4 | 789.4 |
| Growth Solvent | $CHCl_3$ | $CHCl_3$ | $CHCl_3$ | $CHCl_3$ |
| Crystal system | Monoclinic | Monoclinic | Monoclinic | Monoclinic |
| Space group | C2/c | C2/c | C2/c | C2/c |
| Z | 8 | 8 | 8 | 8 |
| a, Å | 23.8429 (12) | 23.8592 (17) | 23.9014 (24) | 23.9014 (24) |
| b, Å | 8.3337 (4) | 8.3364 (6) | 8.3164 (8) | 8.3164 (8) |
| c, Å | 42.0738 (22) | 42.0622 (31) | 41.9864 (43) | 41.9864 (43) |
| α, deg | 90 | 90 | 90 | 90 |
| β, deg | 100.309 (1) | 100.351 (1) | 100.205 (1) | 100.205 (1) |
| γ, deg | 90 | 90 | 90 | 90 |
| V, Å$^3$ | 8225.1 (7) | 8230.0 (10) | 8213.8 (14) | 8213.8 (14) |
| $\rho_{calc}$, g/cm$^3$ | 1.26 | 1.26 | 1.28 | 1.28 |
| crystal dimensions, mm | 0.56 × 0.24 × 0.17 | 0.56 × 0.24 × 0.17 | 0.64 × 0.51 × 0.20 | 0.64 × 0.51 × 0.20 |
| T, K | 100 (2) | 100 (2) | 100 (2) | 100 (2) |
| 2Θ max for refinement, deg | 56.0 | 56.0 | 56.0 | 56.0 |
| total reflections | 35014 | 31362 | 34738 | 34738 |
| independent reflections | 9758 | 9724 | 9668 | 9668 |
| no. of observed data | 7865 | 6753 | 6969 | 6969 |
| no. of parameters | 490 | 490 | 509 | 509 |
| $R_{int}$ | 0.0342 | 0.0633 | 0.0519 | 0.0519 |
| μ, mm$^{-1}$ | 0.218 | 0.214 | 0.197 | 0.197 |
| $R_1(F)$, $wR_2(F^2)$, (I > 2σ(I)) | 0.0468, 0.1115 | 0.0522, 0.1062 | 0.0475, 0.1145 | 0.0475, 0.1145 |
| Goodness-of-fit on $F^2$ | 1.048 | 1.032 | 1.114 | 1.114 |
| CCDC Depository Number | 895268 | 895269 | 895270 | 895460 |

TABLE S9

Crystallographic data for x(guest)@formula (Ib)

| Crystal Parameters | 0.26($CH_4$)@formula (Ib)[a] | $CH_3CN$@formula (Ib) | $NO_2CH_3$@formula (Ib) | 0.67($CH_3OH$)@formula (Ib) |
|---|---|---|---|---|
| Chemical formula | $C_{40.26}H_{49.04}O_8Si_4$ | $C_{42}H_{51}O_8Si_4N$ | $C_{41}H_{51}O_{10}Si_4N$ | $C_{40.67}H_{50.68}O_{8.67}Si_4$ |
| Formula weight, g/mol | 773.31 | 810.2 | 830.19 | 790.61 |
| Growth Solvent | $CHCl_3$ | $CH_3CN$ | $NO_2CH_3$ | $CHCl_3$/MeOH |
| Crystal system | Monoclinic | Monoclinic | Monoclinic | Monoclinic |
| Space group | C2/c | C2/c | C2/c | C2/c |
| Z | 8 | 8 | 8 | 8 |
| a, Å | 23.9345 (127) | 23.8211 (29) | 23.9220 (31) | 23.9064 (22) |
| b, Å | 8.3621 (45) | 8.3280 (12) | 8.2830 (11) | 8.3015 (8) |
| c, Å | 42.1566 (223) | 42.0611 (62) | 42.4669 (54) | 42.1497 (39) |
| α, deg | 90 | 90 | 90 | 90 |
| β, deg | 100.501 (6) | 98.894 (2) | 100.387 (1) | 100.301 (1) |
| γ, deg | 90 | 90 | 90 | 90 |
| V, Å$^3$ | 8296 (8) | 8244 (2) | 8276.7 (19) | 8230.2 (13) |

TABLE S9-continued

Crystallographic data for x(guest)@formula (Ib)

| Crystal Parameters | 0.26(CH$_4$)@formula (Ib)$^a$ | CH$_3$CN@formula (Ib) | NO$_2$CH$_3$@formula (Ib) | 0.67(CH$_3$OH)@formula (Ib) |
|---|---|---|---|---|
| $\rho_{calc}$, g/cm$^3$ | 1.24 | 1.31 | 1.33 | 1.28 |
| crystal dimensions, mm | 0.63 × 0.30 × 0.20 | 0.41 × 0.13 × 0.13 | 0.45 × 0.42 × 0.41 | 0.45 × 0.42 × 0.41 |
| T, K | 100 (2) | 100 (2) | 100 (2) | 100 (2) |
| 2Θ max for refinement, deg | 56.0 | 56.0 | 56.0 | 56.0 |
| total reflections | 34542 | 35118 | 35023 | 34888 |
| independent reflections | 9684 | 9621 | 9736 | 9732 |
| no. of observed data | 7111 | 6337 | 8235 | 6603 |
| no. of parameters | 486 | 510 | 519 | 502 |
| $R_{int}$ | 0.0516 | 0.0728 | 0.0298 | 0.0636 |
| μ, mm$^{-1}$ | 0.192 | 0.197 | 0.202 | 0.196 |
| $R_1$(F), $wR_2$(F$^2$), (I > 2σ(I)) | 0.0478, 0.1109 | 0.0554, 0.1226 | 0.0412, 0.1038 | 0.0522, 0.1151 |
| Goodness-of-fit on F$^2$ | 1.042 | 1.044 | 1.045 | 1.079 |
| CCDC Depository Number | 895459 | 895272 | 895273 | 895274 |

Example 10

Gas Clathrate Synthetic Growth Method

Ambient conditions: the gas of interest was bubbled into a saturated CHCl$_3$ solution of formula (Ib) (1-2 mL) in a borosilicate glass vial until a precipitate started to form. The vial was then capped and reheated to redissolve the precipitate and set aside until crystals formed, usually on the order of hours/days.

Elevated pressures: CAUTION! This method uses liquefied gases under pressures in a closed system. A proper amount of liquid gas was determined by using the van der Waals equation of state so as to not exceed ~80 atm (Teflon bombs rated up to ~120 atm) in about 20 mL of empty volume. From this calculation, an estimated maximum pressure can be determined ($P_{est}$), since solubility of the gas in chloroform is not accounted for and would thus decrease the total pressure in the vessel. The teflon bomb was cooled in liquid nitrogen and then placed into a metal jacket (cooling of the bomb was done with the teflon cap on so as to minimize condensation of water inside). Added to it was the predetermined amount of liquefied gas (or solid in the case of CO2) and a 1 mL saturated solution of formula (Ib) in CHCl$_3$ with activated 3 Å molecular sieves in an uncapped GC-MS vial (1.5 mL capacity) and the bomb was quickly sealed in a metal jacket, allowed to warm to room temperature and set aside for 1-2 weeks. The bomb was re-opened and the crystals of x(gas)@formula (Ib) were filtered off.

0.26(CH$_4$)@Formula (Ib)

Single crystals of a methane clathrate were prepared by the elevated pressure method defined above using 3 mL of CH$_4$ ($P_{est}$≤70 atm). This gave single crystals that were analyzed by SCXRD, TGA and $^1$H NMR spectroscopy. Refinement of the SCXRD data revealed a peak of 1.3 e$^-$/Å$^3$ confined in the cavity. The peak was modeled as a carbon atom with a refined occupancy of 0.26 (Table S9). SQUEEZE analysis of this structure gave 2.13 e$^-$ per cavitand cavity (0.21 eq.). We note that by SCXRD, the purported partial occupancy methane molecule is indistinguishable from a partially occupied water molecule and the structure could as easily be refined as a partial hydrate. $^1$H NMR analysis of the crystals, however, shows at least 0.04 eq. of methane per cavitand. The differences in occupancies between SCXRD and $^1$H NMR may be due to escaping gas upon dissolution of the cavitand inclusion complex. TGA data shows 0.5 weight loss percent to 240° C., however it is not conclusive that methane is the guest in the cavity x(Kr)@Formula (Ib)

Single crystals of a krypton clathrate were prepared by the elevated pressure method defined above using 3 mL of Kr ($P_{est}$≤70 atm). This gave single crystals of 0.54(Ar)@formula (Ib) that were analyzed by SCXRD upon isolation (Table S7). Another crystal that was analyzed from the same batch contained 0.50 eq. of krypton per cavitand (not reported). This single crystal was then heated at 100° C. for two weeks and was shown to possess only 0.07 eq. of krypton by SCXRD (Table S7). TGA studies show 14% guest loss over a 7 day span (0.96 eq. to 0.82 eq. Kr). The sample at day 7 was analyzed by TGA-MS and showed clearly the release of Kr (m/z=84 amu) concomitant with mass loss. $^1$H NMR at day 0 shows no impurities that would be responsible for the mass loss.

x(Xe)@Formula (Ib)

Single crystals of a xenon clathrate were prepared by the elevated pressure method defined above using 3 mL of Xe ($P_{est}$≤50 atm). This gave single crystals of 0.77(Xe)@formula (Ib) that were analyzed by SCXRD upon isolation (Table S6). Another crystal that was analyzed from the same batch after 129 days and gave the same occupancy within error (0.79 eq. Xe/cavitand) (Table S6). TGA studies on the bulk microcrystalline material shows 19% guest loss over a 7 day span (0.93 eq. to 0.73 eq. Xe) The sample at day 7 was analyzed by TGA-MS and showed clearly the release of Xe (m/z=131 amu) concomitant with mass loss. $^1$H NMR at day 0 shows no impurities that would be responsible for the mass loss.

x(C$_2$H$_4$)@Formula (Ib)

Ethylene gas was bubbled into a saturated solution of formula (Ib) in CHCl$_3$ (1 mL) until dryness. The powder was placed in a stream of nitrogen for 1 min. and analyzed by $^1$H NMR after nitrogen purge and 7 days later. Single crystals of an ethylene clathrate were prepared by the elevated pressure method defined above using 3 mL of C$_2$H$_4$ ($P_{est}$≤45 atm). This gave single crystals of 0.41($C_2H_4$)@formula (Ib) that were analyzed by SCXRD upon isolation (Table S7). The same crystal was analyzed 7 days later by SCXRD and was found to be 0.43($C_2H_4$).0.22($H_2O$)@formula (Ib) (Table S7). Inclusion of water in the day 7 crystal structure can be attributed to the single crystal standing in ambient conditions between day 0 and day 7 SCXRD collections and the uptake of water. TGA studies show corresponding mass loss (0.28 eq. $C_2H_4$) and $^1$H NMR at day 0 and 7 shows 0.06 and 0.04 eq. of ethylene, respectively. The differences in occupancies between SCXRD and $^1$H NMR may be due to escaping gas upon dissolution of the cavitand inclusion complex.

x($C_2H_6$)@Formula (Ib)

Ethane gas was bubbled into a saturated solution of formula (Ib) in $CHCl_3$ (1 mL) until dryness. The powder was placed in a stream of nitrogen for 1 min. and analyzed by $^1$H NMR after nitrogen purge and 7 days later. Single crystals of an ethane clathrate were prepared by the elevated pressure method defined above using 4 mL of $C_2H_6$ ($P_{est}$≤40 atm). This gave single crystals of 0.72($C_2H_6$)@formula (Ib) that were analyzed by SCXRD upon isolation. The same crystal studied 10 days later by SCXRD showed 0.75 eq. $C_2H_6$/cavitand (Table S6). TGA studies consistently showed weight loss % values that were 2-3 times the expected mass loss. We conjecture that a small amount of the cavitand co-sublimes simultaneously with the loss of ethane. Despite these inconsistencies, tandem TGA-MS clearly shows the release of ethane (m/z=32 amu) to be concomitant with the mass loss. Also, by placing the material in a sealed DSC pan (with hole for gas escape) and using the same TGA protocol, the correct weight loss % was determined. $^1$H NMR at day 0 and 16 of batch crystals shows 0.38 and 0.35 eq. of ethane, respectively. The differences in occupancies between SCXRD and $^1$H NMR may be due to escaping gas upon dissolution of the cavitand inclusion complex.

x($C_2H_2$)@Formula (Ib)

Acetylene gas (generated by the addition of water to calcium carbide) was bubbled into a saturated solution of formula (Ib) in $CHCl_3$ (1 mL) until dryness. The powder was placed in a stream of nitrogen for 1 minute and analyzed by $^1$H NMR after treatment with nitrogen and 7 days later.

x($CH_3F$)@Formula (Ib)

Fluoromethane was also bubbled into a saturated solution of formula (Ib) in $CHCl_3$ (1 mL) until dryness. The powder was placed in a stream of nitrogen for 1 min. and analyzed by $^1$H NMR after nitrogen purge and 7 days later. These show occupancies of 0.56 and 0.28 eq. of fluoromethane, respectively. Fluoromethane clathrates were grown under the ambient conditions method outlined above. Single crystals that formed over the course of 1-2 weeks to were analyzed by SCXRD and refined to 0.80($CH_3F$)@formula (Ib). A single crystal studied by SCXRD from the same batch after 4 months later gave an occupancy of 0.43 eq. $CH_3F$/cavitand (Table S4). TGA studies show corresponding mass loss at day 0. The differences in occupancies between SCXRD and $^1$H NMR may be due to escaping gas upon dissolution of the cavitand inclusion complex.

x($CO_2$)@Formula (Ib)

Single crystals of a carbon dioxide clathrate were prepared by the elevated pressure method defined above using 5 g of $CO_2$ ($P_{est}$≤60 atm). This gave single crystals of 0.46($CO_2$)@formula (Ib) that were analyzed by SCXRD upon isolation. The same crystal 7 days later was found to contain 0.36 eq. of $CO_2$ (Table S8). TGA studies show 9% guest loss over a 7 day span (0.40 eq. to 0.35 eq. $CO_2$/cavitand). Tandem TGA-MS measurements were made on a 2$^{nd}$ batch of x($CO_2$) @formula (Ib) that clearly shows the release of $CO_2$ (m/z=44 amu) to be concomitant with the mass loss $CH_3Cl$@Formula (Ib)

Chloromethane was bubbled into a saturated solution of formula (Ib) in $CHCl_3$ (1 mL) until dryness. The powder was placed in a stream of nitrogen for 1 min. and analyzed by $^1$H NMR after nitrogen purge and 7 days later. These show occupancies of 1.0 and 0.84 eq. of chloromethane, respectively. Chloromethane clathrates were grown under the ambient conditions method outlined above. Single crystals that formed over the course of 1-2 weeks were analyzed by SCXRD were refined to $CH_3Cl$@formula (Ib) (Table S3). Single crystals of chloromethane under the ambient conditions method were also grown out of ethyl acetate and were shown to be also be fully occupied by chloromethane (Table S3). TGA studies show a mass loss corresponding to 1.04 eq. $CH_3Cl$ (grown from chloroform solution).

0.82($CH_3OCH_3$)@Formula (Ib)

Dimethylether (DME) was bubbled into a saturated solution of formula (Ib) in $CHCl_3$ (1 mL) until dryness. The powder was placed in a stream of nitrogen for 1 min. and later by $^1$H NMR after nitrogen purge (0.36 eq.) and after 7 days (0.34 eq.). Single crystals of a DME clathrate were prepared by the elevated pressure method defined above using 3 mL of $CH_3OCH_3$ ($P_{est}$≤6 atm). This gave single crystals of 0.82($CH_3OCH_3$)@formula (Ib) that were analyzed by SCXRD upon isolation (Table S5). Different occupancies between SCXRD and $^1$H NMR may be due to escaping gas upon dissolution of the complex.

$CH_3CCH$@Formula (Ib).2$CHCl_3$

Propyne was bubbled into a saturated solution of formula (Ib) in $CHCl_3$ (1 mL) until dryness. The powder was placed in a stream of nitrogen for 1 min. and later by $^1$H NMR after nitrogen purge and after 7 days. Propyne clathrates were grown under the ambient conditions method outlined above. Single crystals of the complex were studied by SCXRD and determined to be $CH_3CCH$@formula (Ib).2$CHCl_3$ (Table S10). TGA data could not be obtained due to the rapid loss of propyne and chloroform while grinding during sample preparation. $^1$H NMR analysis at day 0 and day 7 shows 1 eq. of propyne per cavitand initially, followed by no trace of the gas, respectively.

$CH_3Br$@Formula (Ib)

Bromomethane clathrates were grown under the ambient conditions method outlined above. Single crystals that formed over the course of 1-2 weeks were analyzed by SCXRD and refined to $CH_3Br$@formula (Ib) (Table S3). TGA studies show a mass loss corresponding to 1.08 eq. $CH_3Br$ per cavitand. The percentage was taken at the lowest rate of guest loss before sublimation.

0.83($CH_3SH$)@Formula (Ib)

Methanethiol clathrates were grown under the ambient conditions method outlined above. Single crystals that formed over the course of 1-2 weeks were analyzed by SCXRD and refined to 0.83($CH_3SH$)@formula (Ib) (Table S5). TGA data of inclusion compound was not meaningful.

EtCl@Formula (Ib)

A saturated solution of formula (Ib) in $CHCl_3$ (1 mL) was placed in a glass screw cap vial with 5 mL of $EtCl_{(l)}$ and sealed 2 days (P ~2 atm). Single crystals formed within 1 hour to yield EtCl@formula (Ib) that were analyzed by SCXRD (Table S4). $^1$H NMR shows 0.98 eq. of EtCl per cavitand.

0.85($CH_2Cl_2$)@Formula (Ib)

Formula (Ib) was dissolved in dichloromethane and slow evaporation of the solvent yielded single crystals of (0.85)

$CH_2Cl_2$@formula (Ib) that were analyzed by SCXRD (Table S5) (ORTEP is shown below). TGA data shows a mass loss corresponding to 0.97 eq. $CH_2Cl_2$ per cavitand. $^1$H NMR shows 0.84 eq. of $CH_2Cl_2$ per cavitand.

$CH_3I$@Formula (Ib)

Formula (Ib) was dissolved in iodomethane and slow evaporation of the solvent yielded single crystals of $CH_3I$@formula (Ib) that were analyzed by SCXRD (Table S3). TGA data shows 1.05 eq. of $CH_3I$ per cavitand.

0.67($CH_3OH$)@Formula (Ib)

A saturated solution of formula (Ib) in $CHCl_3$ (1 mL) was placed in a glass screw cap vial with 3 mL of MeOH and heated to re-dissolve any precipitate. Single crystals of 0.67($CH_3OH$)@formula (Ib) grew within 1-2 days and were analyzed by SCXRD (Table S9) (ORTEP shown below). TGA data shows a mass loss corresponding to 0.9 eq. of $CH_3OH$ per cavitand. $^1$H NMR shows 0.56 eq. of $CH_3OH$ per cavitand.

0.74($BrCH_2Cl$)@Formula (Ib)

formula (Ib) was dissolved in bromochloromethane and slow evaporation of the solvent yielded single crystals of 0.74($BrCH_2Cl$)@formula (Ib) that were analyzed by SCXRD (Table S4) (ORTEP shown below). TGA data shows a mass loss corresponding to 0.63 eq. of $BrCH_2Cl$ per cavitand. $^1$H NMR shows 0.62 eq. of $BrCH_2Cl$ per cavitand.

0.13(EtOH)@Formula (Ib)

A saturated solution of formula (Ib) in $CHCl_3$ (1 mL) was placed in a glass screw cap vial with 3 mL of EtOH and heated to re-dissolve any precipitate. Single crystals of 0.13(EtOH)@formula (Ib) grew within 1-2 days and analyzed by SCXRD (Table S10) (ORTEP shown below). TGA data shows a mass loss corresponding to release of EtOH and sublimation simultaneously. $^1$H NMR shows 0.11 eq. of EtOH per cavitand.

$CH_3CN$@Formula (Ib)

Formula (Ib) was dissolved in acetonitrile and slow evaporation of the solvent yielded single crystals of 0.97($CH_3CN$)@formula (Ib) that were analyzed by SCXRD (Table S9) (ORTEP shown below). TGA data shows a mass loss corresponding to release of $CH_3CN$ and sublimation simultaneously. $^1$H NMR shows 0.96 eq. of $CH_3CN$ per cavitand.

0.09($CH_2Br_2$)@Formula (Ib)

Formula (Ib) was dissolved in dibromomethane and slow evaporation of the solvent yielded single crystals of 0.09($CH_2Br_2$)@formula (Ib) that were analyzed by SCXRD. Crystal structure shows residual electron density in the cavitand cavity that was not modeled. The occupancy of dibromomethane was ascertained by SQUEEZE calculation. TGA data shows a mass loss corresponding to 0.10 eq. of $CH_2Br_2$ per cavitand. $^1$H NMR shows 0.08 eq. of $CH_2Br_2$ per cavitand.

$NO_2CH_3$@Formula (Ib)

Formula (Ib) was dissolved in nitromethane and slow evaporation of the solvent yielded single crystals of $NO_2CH_3$@formula (Ib) that were analyzed by SCXRD (Table S9) (ORTEP shown below). TGA data shows a mass loss corresponding to release of $NO_2CH_3$ and sublimation simultaneously. $^1$H NMR shows 0.87 eq. of $NO_2CH_3$ per cavitand.

x($H_2O$)@Formula (Ib)

Single crystals of x($H_2O$)@formula (Ib) were made from bulk formula (Ib) from slow evaporation of ethyl acetate (x), acetone (x=0.38), THF (x=0.24) and chloroform (x=0.21) solutions of formula (Ib). The hydrate grown from chloroform solution is reported in Table S2. This crystal was placed in an oven at 150° C. for at least 2 days and was subsequently placed in a humidity chamber at room temperature for 1 week to give the 0.28 eq. hydrate (Table S2). The TGA data shows typical mass loss for x($H_2O$)@formula (Ib).

0.06($I_2$)@Formula (Ib)

Approximately 10 mg of $I_2$ was added to a saturated solution of formula (Ib) in $CHCl_3$ (1 mL) and slow evaporation of the solvent yielded single crystals of 0.06($I_2$)@formula (Ib) that were analyzed by SCXRD (Table S5) (ORTEP shown below). TGA data shows a mass loss corresponding to 0.06 eq. of $I_2$ per cavitand.

Example 11

Separations Experiments with EtCl, MeCl and DME Using Crystalline Compositions of Formula (Ib)

Bulk x($H_2O$)@formula (Ib) was prepared. The powder can be activated at 150° C. over two days before use in separations experiments. Activated, empty formula (Ib) (approximately 50 mg) was placed in Teflon bomb along with liquefied MeCl and EtCl or MeCl and DME and sealed for 2 days. The gas present in the smallest amount (usually MeCl) was always in much higher excess than cavitand (approximately 10-20×).

The $^1$H NMR of the gas mixture was taken before adding to the Teflon bomb to determine the mole fractions of the gases (XMeCl and XEtCl or DME). After 2 days, the bombs were placed into liquid nitrogen to re-condense the gases inside, opened, and the suspension was filtered off (cooling method). Some of the bombs were opened without cooling and the liquid gases let evaporate to determine if there is a significant difference in selectivity numbers (evaporation method). Other pairwise experiments involved pouring the liquefied gas mixture into a saturated solution of cavitand in chloroform (~0.1 M), which induced precipitation within seconds (precipitation method). These were filtered off after 1 hour and analyzed further.

Preparation of solid solutions involved pouring the liquefied gas mixtures into more dilute solutions of cavitand in chloroform (~17 mM) and waiting for single crystals to form to be analyzed by NMR and SCXRD (solid-solution method). The $^1$H NMR of the solids were then taken to determine the mole fraction of gases that were bound by formula (Ib) ($Y_{MeCl}$ and $Y_{EtCl\ or\ DME}$). Selectivity coefficients were then determined for experiments in which the total amount of bound gases was larger than 0.10 eq. per cavitand. These values were then averaged and the standard deviation determined to give the overall selectivity coefficient over several trials.

TABLE S10

Crystallographic Data x(CH$_3$Cl)•y(Guest)@formula (Ib).

| Crystal Parameters | 0.22(CH$_3$Cl)•0.71(EtCl)@formula (Ib) | 0.63(CH$_3$Cl)•0.25(DME)@formula (Ib) |
|---|---|---|
| Chemical formula | C$_{41.61}$H$_{52.21}$O$_8$Si$_4$Cl$_{0.93}$ | C$_{41.13}$H$_{51.39}$O$_{8.25}$Si$_4$Cl$_{0.63}$ |
| Formula weight, g/mol | 826.07 | 812.48 |
| Solvent | CHCl$_3$/CH$_3$Cl/EtCl | CHCl$_3$/CH$_3$Cl/DME |
| Crystal system | Monoclinic | Monoclinic |
| Space group | C2/c | C2/c |
| Z | 8 | 8 |
| a, Å | 23.6217 (52) | 23.7861 (29) |
| b, Å | 8.4439 (19) | 8.3394 (10) |
| c, Å | 42.6937 (95) | 42.2839 (52) |
| α, deg | 90 | 90 |
| β, deg | 99.612 (3) | 99.334 (2) |
| γ, deg | 90 | 90 |
| V, Å$^3$ | 8396 (3) | 8276.5 (17) |
| ρ$_{calc}$, g/cm$^3$ | 1.31 | 1.31 |
| crystal dimensions, mm | 0.37 × 0.27 × 0.17 | 0.18 × 0.18 × 0.12 |
| T, K | 100 (2) | 100 (2) |
| 2Θ max for refinement, deg | 56 | 56 |
| total reflections | 35664 | 25359 |
| independent reflections | 9903 | 7271 |
| no. of observed data | 6743 | 4887 |
| no. of parameters | 520 | 509 |
| R$_{int}$ | 0.0655 | 0.0889 |
| μ, mm$^{-1}$ | 0.252 | 0.236 |
| R$_1$(F), wR$_2$(F$^2$), (I > 2σ(I)) | 0.0503, 0.1006 | 0.0511, 0.1019 |
| Goodness-of-fit on F$^2$ | 1.018 | 0.995 |

TABLE S11

Crystallographic Data x(Guest)@H, H, SiMe$_2$

| Crystal Parameters | H, H, SiMe$_2$ | 0.91(MeCl)@H, H, SiMe$_2$ |
|---|---|---|
| Chemical formula | C$_{36}$H$_{40}$O$_8$Si$_4$ | C$_{36.91}$H$_{42.73}$O$_8$Si$_4$Cl$_{0.91}$ |
| Formula weight, g/mol | 713.05 | 759 |
| Solvent | none | EtOAc |
| Crystal system | Monoclinic | Monoclinic |
| Space group | P2$_1$/n | P2$_1$/m |
| Z | 4 | 4 |
| a, Å | 15.2400 (19) | 10.8232 (11) |
| b, Å | 11.1290 (14) | 23.1753 (24) |
| c, Å | 22.6153 (28) | 15.2837 (16) |
| α, deg | 90 | 90 |
| β, deg | 107.000 (2) | 90.427 (2) |
| γ, deg | 90 | 90 |
| V, Å$^3$ | 3668.1 (8) | 3833.5 (7) |
| ρ$_{calc}$, g/cm$^3$ | 1.29 | 1.31 |
| crystal dimensions, mm | 0.52 × 0.50 × 0.25 | 0.51 × 0.22 × 0.22 |
| T, K | 100 (2) | 100 (2) |
| 2Θ max for refinement, deg | 56 | 56 |
| total reflections | 31479 | 33693 |
| independent reflections | 8646 | 9268 |
| no. of observed data | 5825 | 5563 |
| no. of parameters | 441 | 481 |
| R$_{int}$ | 0.0586 | 0.0783 |
| μ, mm$^{-1}$ | 0.211 | 0.268 |
| R$_1$(F), wR$_2$(F$^2$), (I > 2σ(I)) | 0.0503, 0.1204 | 0.0526, 0.1211 |
| Goodness-of-fit on F$^2$ | 1.083 | 0.965 |

TABLE S12

Raw data of MeCl vs. EtCl competition experiments. Equivalents were determined by $^1$H NMR unless otherwise specified and K calculated by equation 1. Trial 1-10 were done by the cooling method, trials 11-14 done by the evaporation method, trials 15 and 16 done by the precipitation method, and trial 17 was performed by crystal preparation of a solid-solution, studied further by NMR and SCXRD.

| Trial | Ratio before (X) | Ratio after (Y) | K$_{MeCl:EtCl}$ | Eq. MeCl/cup | Eq. EtCl/cup |
|---|---|---|---|---|---|
| 1 | 1:1.13 | 1:0.06 | 19 | 0.54 | 0.03 |
| 2 | 1:1.34 | 1:0.05 | 27 | 0.67 | 0.03 |
| 3 | 1:2.81 | 1:0.09 | 31 | 0.44 | 0.04 |

TABLE S12-continued

Raw data of MeCl vs. EtCl competition experiments.
Equivalents were determined by $^1$H NMR unless otherwise
specified and K calculated by equation 1. Trial 1-10 were done by
the cooling method, trials 11-14 done by the evaporation method,
trials 15 and 16 done by the precipitation method, and trial 17 was
performed by crystal preparation of a solid-solution, studied
further by NMR and SCXRD.

| Trial | Ratio before (X) | Ratio after (Y) | $K_{MeCl:EtCl}$ | Eq. MeCl/cup | Eq. EtCl/cup |
|---|---|---|---|---|---|
| 4 | 1:141 | 1:7.53 | 19 | 0.1 | 0.78 |
| 5 | 1:259 | 1:11.9 | 22 | 0.07 | 0.82 |
| 6 | 1:237 | 1:10 | 24 | 0.08 | 0.81 |
| 7 | 1:41 | 1:2.47 | 17 | 0.26 | 0.63 |
| 8 | 1:46 | 1:1.92 | 24 | 0.27 | 0.52 |
| 9 | 1:6.18 | 5.5:1 | 34 | 0.44 | 0.08 |
| 10 | 1:6.79 | 4.4:1 | 30 | 0.49 | 0.11 |
| 11 | 1:1117 | 1:37 | 30 | 0.02 | 0.9 |
| 12 | 1:242 | 1:16 | 15 | 0.06 | 0.94 |
| 13 | 1:1900 | 1:83 | 23 | 0.01 | 0.99 |
| 14 | 1:497 | 1:34 | 15 | 0.03 | 0.95 |
| 15 | 1:24 | 1:1.17 | 21 | | |
| 16 | 1:30 | 1:1.49 | 20 | | |
| 17 | 1:78 | 1:4.38 (NMR) | 18 | | |
| | | 1:3.23 (SCXRD) | 24 | | |
| | $K_{MeCl:EtCl}$ (average): | | 23 (6) | | |

TABLE S13

Raw data of MeCl vs. DME competition experiments.
Equivalents were determined by $^1$H NMR unless otherwise
specified and K calculated by equation 1. Trial 1-11 were done by
the cooling method, trials 12-15 done by the evaporation method,
trials 16 and 17 done by the precipitation method, and trial 18 was
performed by crystal preparation of a solid-solution, studied
further by NMR and SCXRD.

| Trial | Ratio before (X) | Ratio after (Y) | $K_{MeCl:DME}$ | Eq. MeCl/cup | Eq. DME/cup |
|---|---|---|---|---|---|
| 1 | 1:1.05 | 1:0.045 | 23 | 0.4 | 0.02 |
| 2 | 1:1.14 | 1:0.06 | 19 | 0.06 | 0.004 |
| 3 | 1:0.99 | 1:0.02 | 50 | 0.33 | 0.005 |
| 4 | 1:1.01 | 1:0.015 | 67 | 0.14 | 0.01 |
| 5 | 1:88 | 1:2.1 | 42 | 0.24 | 0.51 |
| 6 | 1:52 | 1:0.98 | 53 | 0.36 | 0.36 |
| 7 | 1:68 | 1:1.02 | 67 | 0.09 | 0.1 |
| 8 | 1:49 | 1:1.19 | 41 | 0.27 | 0.29 |
| 9 | 1:46 | 1:0.67 | 69 | 0.09 | 0.06 |
| 10 | 1:3.76 | 11.8:1 | 44 | 0.07 | 0.006 |
| 11 | 1:4.09 | 10.42:1 | 43 | 0.33 | 0.03 |
| 12 | 1:56 | 1:1.64 | 34 | 0.3 | 0.49 |
| 13 | 1:177 | 1:7.1 | 25 | 0.07 | 0.53 |
| 14 | 1:129 | 1:3.2 | 40 | 0.12 | 0.38 |
| 15 | 1:451 | 1:8.7 | 52 | 0.06 | 0.52 |
| 16 | 1:21 | 1.63:1 | 34 | | |
| 17 | 1:14 | 1.68:1 | 24 | | |
| 18 | 1:29 | 3.19:1 (NMR) | 93 | | |
| | | 2.52:1 (SCXRD) | 73 | | |
| | $K_{MeCl:DME}$ (average): | | 45 (18) | | |

The invention claimed is:

1. A composition comprising a compound of formula (I):

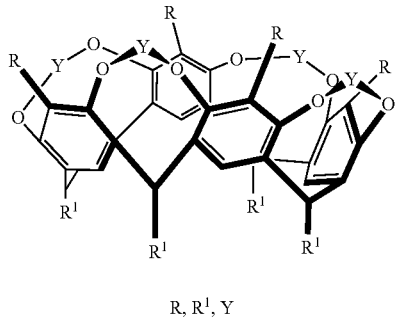

R, R¹, Y and/or a stereoisomer thereof; wherein
R is H, $C_1$-$C_6$ alkyl, halo, or $NO_2$;
R¹ is H, $C_1$-$C_6$ alkyl, Ph, ($C_1$-$C_6$ alkyl)$_x$Ph, (C(halo)$_3$)$_x$Ph, or (halo)$_x$Ph;
Y is —Si($C_1$-$C_6$ alkyl)$_2$-; and
x is an integer from 1-3, and
wherein the composition is in a crystalline form that comprises void spaces of at least 15 Å³; and wherein the void spaces are free of other atoms and molecules.

2. The composition of claim 1; wherein for the compound of formula (I):
R is H, $CH_3$, Br, or $NO_2$;
R¹ is H, $CH_3$, $CH_2CH_3$, i-Bu, Ph, 4-$CH_3$Ph, 4-$CF_3$Ph, 3,5-($CF_3$)$_2$Ph, or 3,5-$F_2$Ph; and
Y is —Si($CH_3$)$_2$—, —Si($CH_3CH_2$)$_2$—, or —Si(i-Pr)$_2$—.

3. The composition of claim 1; wherein for the compound of formula (I):
R is H;
R¹ is H, $CH_3$, i-Bu, Ph, 4-$CF_3$Ph, 3,5-($CF_3$)$_2$Ph, or 3,5-$F_2$Ph; and
Y is —Si($CH_3$)$_2$—, —Si($CH_3CH_2$)$_2$—, or —Si(i-Pr)$_2$—.

4. The composition of claim 1; wherein for the compound of formula (I):
R is H, $CH_3$, or Br;
R¹ is H, $CH_3$, $CH_2CH_3$, Ph, or 4-$CH_3$Ph; and
Y is —Si($CH_3$)$_2$—, or Si($CH_2CH_3$)$_2$.

5. The composition of claim 1; wherein the compound of formula (I) is the rccc or the rctt stereoisomer.

6. A composition comprising a compound of formula (I):

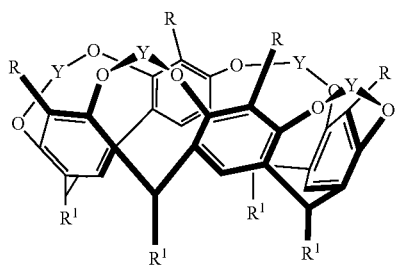

R, R¹, Y and/or a stereoisomer thereof; wherein the compound of formula (I) is selected from the following (R, R¹, Y):

(H, H, Si($CH_3$)$_2$); (H, i-Bu, Si($CH_3$)$_2$); ($CH_3$, $CH_3$, Si($CH_3$)$_2$); ($CH_3$, $CH_3CH_2$, Si($CH_3$)$_2$); ($CH_3$, H, Si($CH_3CH_2$)$_2$); ($CH_3$, $CH_3$, Si($CH_3CH_2$)$_2$); (H, H, Si(i-Pr)$_2$); (H, $CH_3$, Si(i-Pr)$_2$); ($CH_3$, H, Si(i-Pr)$_2$); and ($CH_3$, $CH_3$, Si(i-Pr)$_2$).

7. The composition of claim 1; wherein the compound of formula (I) comprises void spaces of 20 Å³ to 300 Å³.

8. The composition of claim 1; wherein thermogravimetric analysis (TGA) of the composition reveals no more than 1% mass loss up to the temperature of sublimation of the composition.

9. A composition comprising a compound of formula (I)

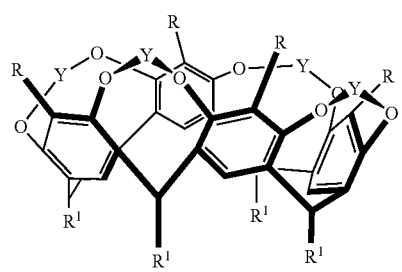

R, R¹, Y and/or a stereoisomer thereof;
wherein the composition is a host-guest complex, where at least some void spaces of the composition comprise one or more guest gas molecules or atoms, and
wherein the compound of formula (I) is selected from the following (R, R¹, Y):
(H, H, Si($CH_3$)$_2$); (H, i-Bu, Si($CH_3$)$_2$); ($CH_3$, $CH_3$, Si($CH_3$)$_2$); ($CH_3$, $CH_3CH_2$, Si($CH_3$)$_2$); ($CH_3$, H, Si($CH_3CH_2$)$_2$); ($CH_3$, $CH_3$, Si($CH_3CH_2$)$_2$); (H, H, Si(i-Pr)$_2$); (H, $CH_3$, Si(i-Pr)$_2$); ($CH_3$, H, Si(i-Pr)$_2$); and ($CH_3$, $CH_3$, Si(i-Pr)$_2$).

10. The composition of claim 9; wherein the guest gas is selected from one or more of acetylene, argon, krypton, xenon, carbon dioxide, methane, ethylene, ethane, propyne, propene, propane, fluoromethane, chloromethane, chloroethane, dimethylether, freons, gaseous fluorocarbons, methanethiol, oxygen, nitrogen, and bromomethane.

11. A chemical compound of formula (IIa);

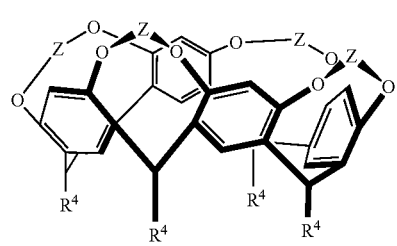

and/or a stereoisomer thereof; wherein
R⁴ is H, $CH_3$, i-Bu, Ph, 4-$CF_3$Ph, 3,5-($CF_3$)$_2$Ph, or 3,5-$F_2$Ph; and
Z is —Si($CH_3$)$_2$—, —Si($CH_3CH_2$)$_2$—, or —Si(i-Pr)$_2$—;
wherein R⁴ is not $CH_3$ when Z is —Si($CH_3$)$_2$—, or Si($CH_3CH_2$)$_2$.

12. The chemical compound of claim 11; wherein the compound of formula (IIa) is selected from the following (R⁴, Z):
(H, Si($CH_3$)$_2$); (i-Bu, Si($CH_3$)$_2$); (H, Si(i-Pr)$_2$); and ($CH_3$, Si(i-Pr)$_2$).

13. The composition of claim 1, wherein (R, $R^1$, Y) is (H, H, $Si(CH_3)_2$).

14. The composition of claim 9, wherein (R, $R^1$, Y) is (H, H, $Si(CH_3)_2$).

15. A composition comprising a compound of formula (I):

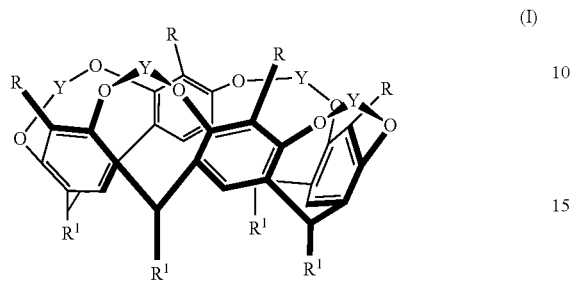

(I)

R, $R^1$, Y and/or a stereoisomer thereof; wherein
R is H, $C_1$-$C_6$ alkyl, halo, or $NO_2$;
$R^1$ is H, $C_1$-$C_6$ alkyl, Ph, ($C_1$-$C_6$ alkyl)$_x$Ph, (C(halo)$_3$)$_x$Ph, or (halo)$_x$Ph;
Y is $Si(C_1$-$C_6$ alkyl)$_2$; and
x is an integer from 1-3, provided that when Y is —Si$(CH_3)_2$— then R is not $CH_3$ and $R^1$ is not H, wherein the composition is in a crystalline form that comprises void spaces of at least 15 Å$^3$; and wherein the void spaces are free of other atoms and molecules.

* * * * *